(12) United States Patent
Capano et al.

(10) Patent No.: US 12,011,451 B2
(45) Date of Patent: Jun. 18, 2024

(54) STABILIZED COMPOSITIONS COMPRISING CANNABIDIOL

(71) Applicants: Ecofibre USA Inc., Georgetown, KY (US); The University of Newcastle, Callaghan (AU)

(72) Inventors: Alexandra M. Capano, Philadelphia, PA (US); Pradeep Singh Tanwar, Fletcher (AU)

(73) Assignees: Ecofibre USA Inc., Georgetown, KY (US); The University of Newcastle, Callaghan (AU)

( * ) Notice: Subject to any disclaimer, the term of this patent is extended or adjusted under 35 U.S.C. 154(b) by 0 days.

(21) Appl. No.: 18/493,997

(22) Filed: Oct. 25, 2023

(65) Prior Publication Data

US 2024/0165136 A1    May 23, 2024

Related U.S. Application Data

(60) Provisional application No. 63/381,038, filed on Oct. 26, 2022.

(51) Int. Cl.
| | | |
|---|---|---|
| *A61K 36/00* | (2006.01) | |
| *A61K 31/00* | (2006.01) | |
| *A61K 31/282* | (2006.01) | |
| *A61K 31/337* | (2006.01) | |
| *A61K 31/353* | (2006.01) | |
| *A61K 31/704* | (2006.01) | |
| *A61K 36/185* | (2006.01) | |
| *A61P 35/00* | (2006.01) | |

(52) U.S. Cl.
CPC .......... *A61K 31/658* (2023.05); *A61K 31/282* (2013.01); *A61K 31/337* (2013.01); *A61K 31/353* (2013.01); *A61K 31/704* (2013.01); *A61K 36/185* (2013.01); *A61P 35/00* (2018.01)

(58) Field of Classification Search
CPC ................................... A61K 31/658
See application file for complete search history.

(56) References Cited

U.S. PATENT DOCUMENTS

| | | |
|---|---|---|
| 10,098,867 B2 | 10/2018 | Javid et al. |
| 11,123,308 B2 | 9/2021 | Yu et al. |
| 2010/0273895 A1 | 10/2010 | Stinchcomb et al. |
| 2011/0086113 A1 | 4/2011 | Velasco Diez et al. |
| 2015/0086653 A1 | 3/2015 | Parolaro et al. |
| 2016/0136128 A1 | 5/2016 | Javid et al. |
| 2019/0282513 A1 | 9/2019 | Yerike |
| 2020/0253919 A1 | 8/2020 | Raz et al. |
| 2020/0408740 A1 | 12/2020 | Ballan et al. |
| 2021/0052512 A1 | 2/2021 | Guy et al. |
| 2021/0068444 A1 | 3/2021 | Alarcon et al. |
| 2021/0069608 A1 | 3/2021 | Galyuk |
| 2021/0085638 A1 | 3/2021 | Hospodor |
| 2021/0128521 A1 | 5/2021 | Palaio |
| 2021/0145764 A1 | 5/2021 | Lephart |
| 2022/0000774 A1 | 1/2022 | Dely |
| 2022/0054429 A1 | 2/2022 | Nathan et al. |
| 2022/0062224 A1 | 3/2022 | Gubler et al. |
| 2022/0202765 A1 | 6/2022 | Altman et al. |
| 2022/0253919 A1 | 8/2022 | Denner |
| 2022/0331287 A1 | 10/2022 | Morgan et al. |
| 2023/0015268 A1 | 1/2023 | Altman et al. |
| 2023/0127098 A1 | 4/2023 | Capano et al. |
| 2023/0132189 A1 | 4/2023 | Capano et al. |
| 2023/0248747 A1 | 8/2023 | Altman et al. |
| 2023/0355645 A1 | 11/2023 | Storch et al. |

FOREIGN PATENT DOCUMENTS

| | | |
|---|---|---|
| CN | 108433880 A | 8/2018 |
| CN | 110063953 A | 7/2019 |
| EP | 3368024 A1 | 9/2018 |
| EP | 3449992 A1 | 3/2019 |
| EP | 3544598 A1 | 10/2019 |
| EP | 3915550 A1 | 12/2021 |
| EP | 3937914 A1 | 1/2022 |
| GB | 2516335 A | 1/2015 |
| RU | 2745687 C1 | 3/2021 |
| WO | WO/2013/165251 A1 | 11/2013 |
| WO | WO/2014/057067 A1 | 4/2014 |
| WO | WO/2016/187679 A1 | 12/2016 |
| WO | WO/2017/072773 A1 | 5/2017 |
| WO | WO/2018/167038 A1 | 9/2018 |
| WO | WO/2019/003163 A2 | 1/2019 |
| WO | WO/2019/034113 A1 | 2/2019 |

(Continued)

OTHER PUBLICATIONS

Tallaride, Quantitative methods for assessing drug synergism, Genes & Cancer 2(11) 1003-1008, 2011 (Year: 2011).*
Raskin et al, Can an apple a day keep the doctor away, Current Pharmaceutical Designs, 2004, 10: 3419-3429 (Year: 2004).*
Tomko et al, Anti-cancer properties of cannflavin A and potential synergistic effects with gemcitabine, cisplatin, and cannabinoids in bladder cancer. Journal of Cannabis Research, (Jul. 22, 2022) vol. 4, No. 1, pp. 1-14. Article No. 41 (Year: 2022).*
Armour, et al., "Self-Management Strategies Amongst Australian Women With Endometriosis: A National Online Survey", BMC Complementary and Alternative Medicine, vol. 19, No. 1, art. 17, Jan. 15, 2019, 1-8.

(Continued)

*Primary Examiner* — Qiuwen Mi
(74) *Attorney, Agent, or Firm* — Vos-IP, LLC

(57) ABSTRACT

Compositions and methods of use of treatment of one or more of ovarian cancer, endometrial cancer, head and neck cancer, noncancerous gynecological disorders, and estrogen sensitive cancers, the composition comprising an effective amount of a cannabinoid and a flavonoid wherein the method comprises administering to a patient in need thereof an effective amount of the composition and optionally administering the composition concomitantly with a chemotherapeutic agent.

10 Claims, 38 Drawing Sheets

(56) References Cited

FOREIGN PATENT DOCUMENTS

| WO | WO/2019/106652 | A1 | 6/2019 | |
|----|----|----|----|----|
| WO | WO/2019/145552 | A1 | 8/2019 | |
| WO | WO/2019/195943 | A1 | 10/2019 | |
| WO | WO/2019/222459 | A1 | 11/2019 | |
| WO | WO/2020/036655 | A9 | 2/2020 | |
| WO | WO/2020/163775 | A1 | 8/2020 | |
| WO | WO/2020/165878 | A1 | 8/2020 | |
| WO | WO/2020/183455 | A1 | 9/2020 | |
| WO | WO/2020/194237 | A1 | 10/2020 | |
| WO | WO/2020/209902 | A1 | 10/2020 | |
| WO | WO/2021/011790 | A1 | 1/2021 | |
| WO | WO/2021/016718 | A1 | 2/2021 | |
| WO | WO/2021/028646 | A1 | 2/2021 | |
| WO | WO/2021/099792 | A1 | 5/2021 | |
| WO | WO/2021/130728 | A1 | 7/2021 | |
| WO | WO/2021/158251 | A1 | 8/2021 | |
| WO | WO/2021/235977 | A1 | 11/2021 | |
| WO | WO/2021/240510 | A1 | 12/2021 | |
| WO | WO/2021/245522 | A1 | 12/2021 | |
| WO | WO/2022/013854 | A1 | 1/2022 | |
| WO | WO/2022/016160 | A1 | 1/2022 | |
| WO | WO/2022/018708 | A1 | 1/2022 | |
| WO | WO-2022011393 | A1 * | 1/2022 | .............. A61K 31/05 |
| WO | WO/2022/105952 | A1 | 5/2022 | |
| WO | WO/2022/118303 | A1 | 6/2022 | |
| WO | WO/2022/144878 | A1 | 7/2022 | |
| WO | WO/2022/165349 | A1 | 8/2022 | |
| WO | WO/2022/165439 | A1 | 8/2022 | |
| WO | WO-2022204422 | A1 * | 9/2022 | ........... A61K 31/015 |
| WO | WO/2022/215071 | A1 | 10/2022 | |
| WO | WO/2022/225658 | A1 | 10/2022 | |
| WO | WO/2023/287742 | A1 | 1/2023 | |
| WO | WO/2023/014818 | A2 | 2/2023 | |
| WO | WO/2023/062634 | A1 | 4/2023 | |

OTHER PUBLICATIONS

Escudero-Lara, et al., "Disease-Modifying Effects of Natural Δ9-Tetrahydrocannabinol in Endometriosis-Associated Pain", eLife, vol. 9, art. e50356, Jan. 14, 2020, https://elifesciences.org/articles/50356.

Fonseca, et al., "Cannabinoid-Induced Cell Death in Endometrial Cancer Cells: Involvement of TRPV1 Receptors in Apoptosis", Journal of Physiology and Biochemistry, vol. 74, No. 2, Feb. 13, 2018, 261-272.

Fraguas-Sánchez, et al., "Enhancing Ovarian Cancer Conventional Chemotherapy Through the Combination With Cannabidiol Loaded Microparticles", European Journal of Pharmaceutics and Biopharmaceutics, vol. 154, Jul. 17, 2020, 246-258.

Go, et al., "Cannabidiol Enhances Cytotoxicity of Anti-Cancer Drugs in Human Head and Neck Squamous Cell Carcinoma", Scientific Reports, vol. 10, No. 1, art. 20622, Nov. 26, 2020, 1-11.

Griffiths, et al., "Cannabidiol Suppresses 3-Dimensional Ovarian Cancer Growth and May Enhance Potency of Classic and Epigenetic Therapies", Gynecologic Oncology, vol. 162, suppl. 1, Abstracts for the 2021 Society of Gynecologic Oncology 52nd Annual Meeting on Women's Cancer, Aug. 18, 2021, S102-S103.

Kenyon, et al., "Report of Objective Clinical Responses of Cancer Patients to Pharmaceutical-Grade Synthetic Cannabidiol", Anticancer Research, vol. 38, No. 10, Oct. 1, 2018, 5831-5835.

Lazarjani, et al., "Processing and Extraction Methods of Medicinal Cannabis: A Narrative Review", Journal of Cannabis Research, vol. 3, art. 32, Jul. 19, 2021, 1-15.

Marinelli, et al., "The Effects of Cannabidiol and Prognostic Role of TRPV2 in Human Endometrial Cancer", International Journal of Molecular Sciences, vol. 21, No. 15, art. 5409, Jul. 29, 2020, 1-22.

Marinotti, et al., "Differentiating Full-Spectrum Hemp Extracts from CBD Isolates: Implications for Policy, Safety and Science", Journal of Dietary Supplements, vol. 17, No. 5, Jun. 16, 2020, 517-526.

Ökten, et al., "Cannabidiol as a Potential Novel Treatment for Endometriosis by Its Anti-Inflammatory and Anti-Oxidative Effects in an Experimental Rat Model", Human Reproduction, vol. 37, issue supp. 1, Jun. 30, 2022, i111.

Rais, et al., "Phytochemicals in the Treatment of Ovarian Cancer", Frontiers in Bioscience-Elite, vol. 9, No. 1, Jan. 1, 2017, 67-75.

Rush, et al., "Cannabidiol: Assessing Activity in Ovarian and Endometrial Carcinoma Cell Lines", Abstracts for the 2021 Society of Gynecologic Oncology 52nd Annual Meeting on Women's Cancer, Featured Posters 188—Poster Session, vol. 162, suppl. 1, Aug. 1, 2021, https://doi.org/10.1016/S0090-8258(21)00839-8.

Sumanasekera, et al., "Hemp Extract With Specific Anti-Cancer Properties Against Ovarian Cancer", The FASEB Journal Special Issue: Experimental Biology 2021 Meeting Abstracts, vol. 35, No. S1, May 14, 2021, https://doi.org/10.1096/fasebj.2021.35.S1.02877.

Van Weelden, et al., "Anti-Estrogen Treatment in Endometrial Cancer: A Systematic Review", Frontiers in Oncology, vol. 9, art. 359, May 7, 2019, 1-12.

International Search Report issued in International Application No. PCT/US2023/077706 dated Feb. 28, 2024.

Hazekamp, et al., "Preparative Isolation of Cannabinoids from Cannabis sativa by Centrifugal Partition Chromatography", Journal of Liquid Chromatography & Related Technologies, vol. 27, No. 15, 2004, 2421-2439.

Jaidee, et al., "Kinetics of CBD, $\Delta^9$-THC Degradation and Cannabinol Formation in Cannabis Resin at Various Temperature and pH Conditions", Cannabis and Cannabinoid Research, vol. 7, No. 4, Aug. 9, 2022, 1-11.

Jin, et al., "Identification of Chemotypic Markers in Three Chemotype Categories of Cannabis Using Secondary Metabolites Profiled in Inflorescences, Leaves, Stem Bark, and Roots", Frontiers in Plant Science, vol. 12, art. 699530, Jul. 1, 2021, 1-16.

Midatech Pharma US Inc., Soltamox® Product Label, Revised Apr. 2019.

Olivas-Aguirre, et al., "Tamoxifen Sensitizes Acute Lymphoblastic Leukemia Cells to Cannabidiol by Targeting Cyclophilin-D and Altering Mitochondrial $Ca^2$ Homeostasis", International Journal of Molecular Sciences, vol. 22, No. 16, Aug. 13, 2021, 1-14.

* cited by examiner

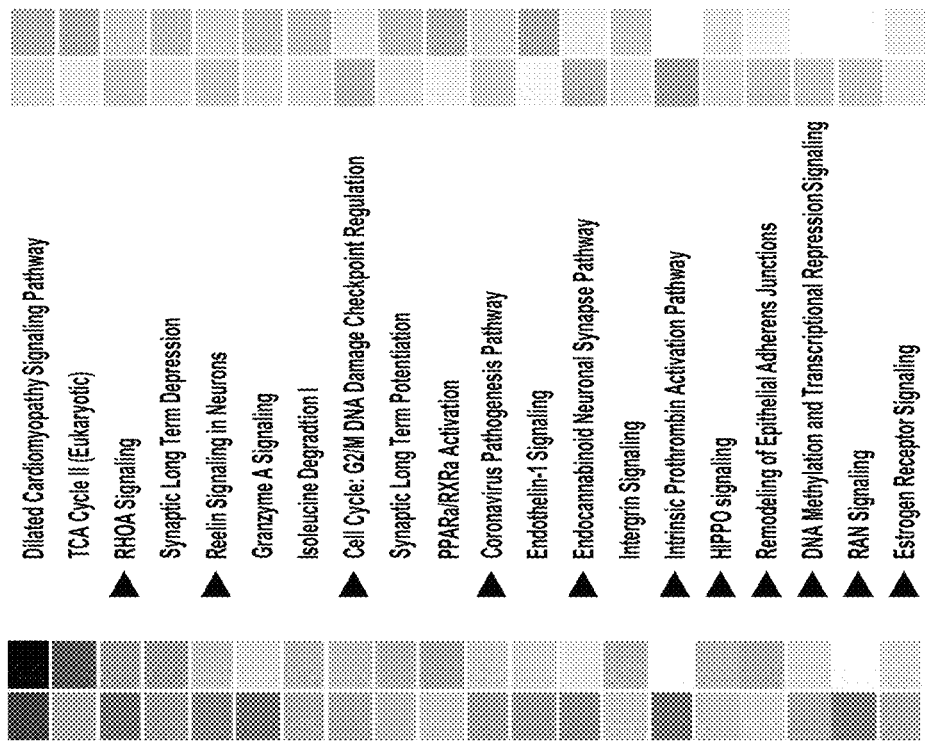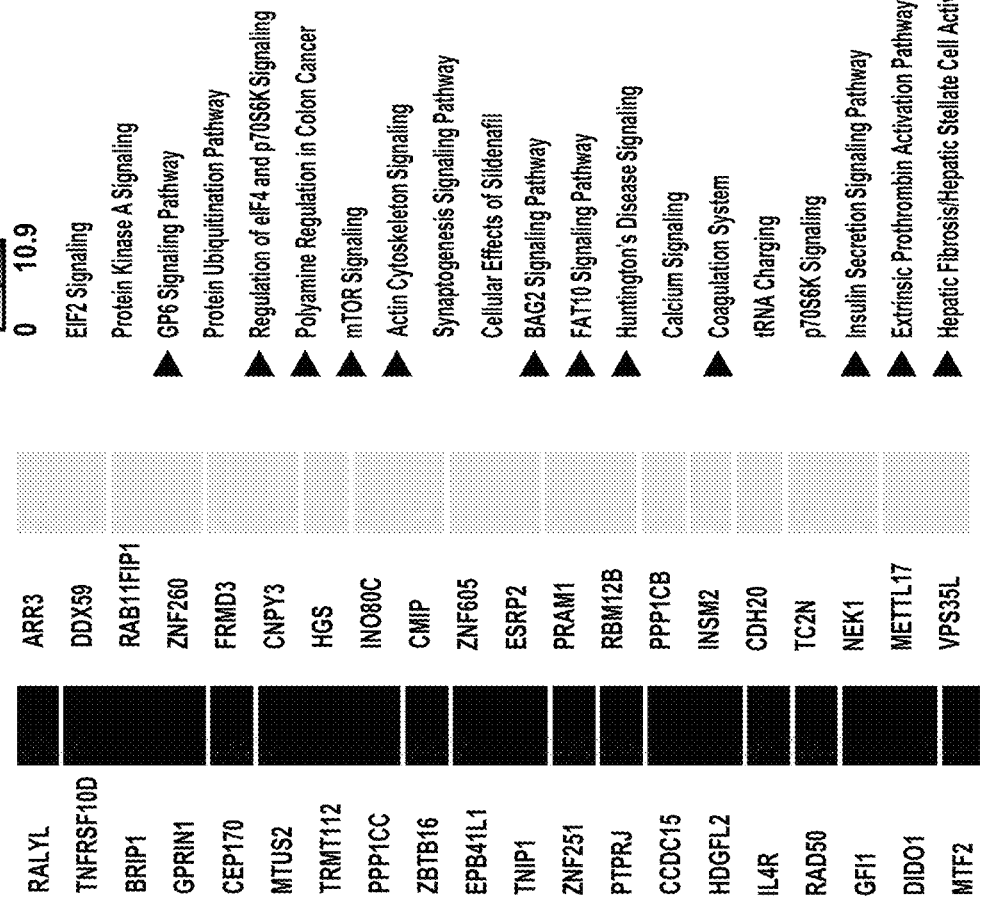
FIGURE 1D
FIGURE 1E

Cannabinoid Receptor 1 Protein Expression in Endometrial Cancer Patient Samples

Endometrial Cancer (Endometrioid Type)

Cannabinoid Receptor 2 Protein Expression in Endometrial Cancer Patient Samples

Endometrial Cancer (Endometrioid Type)

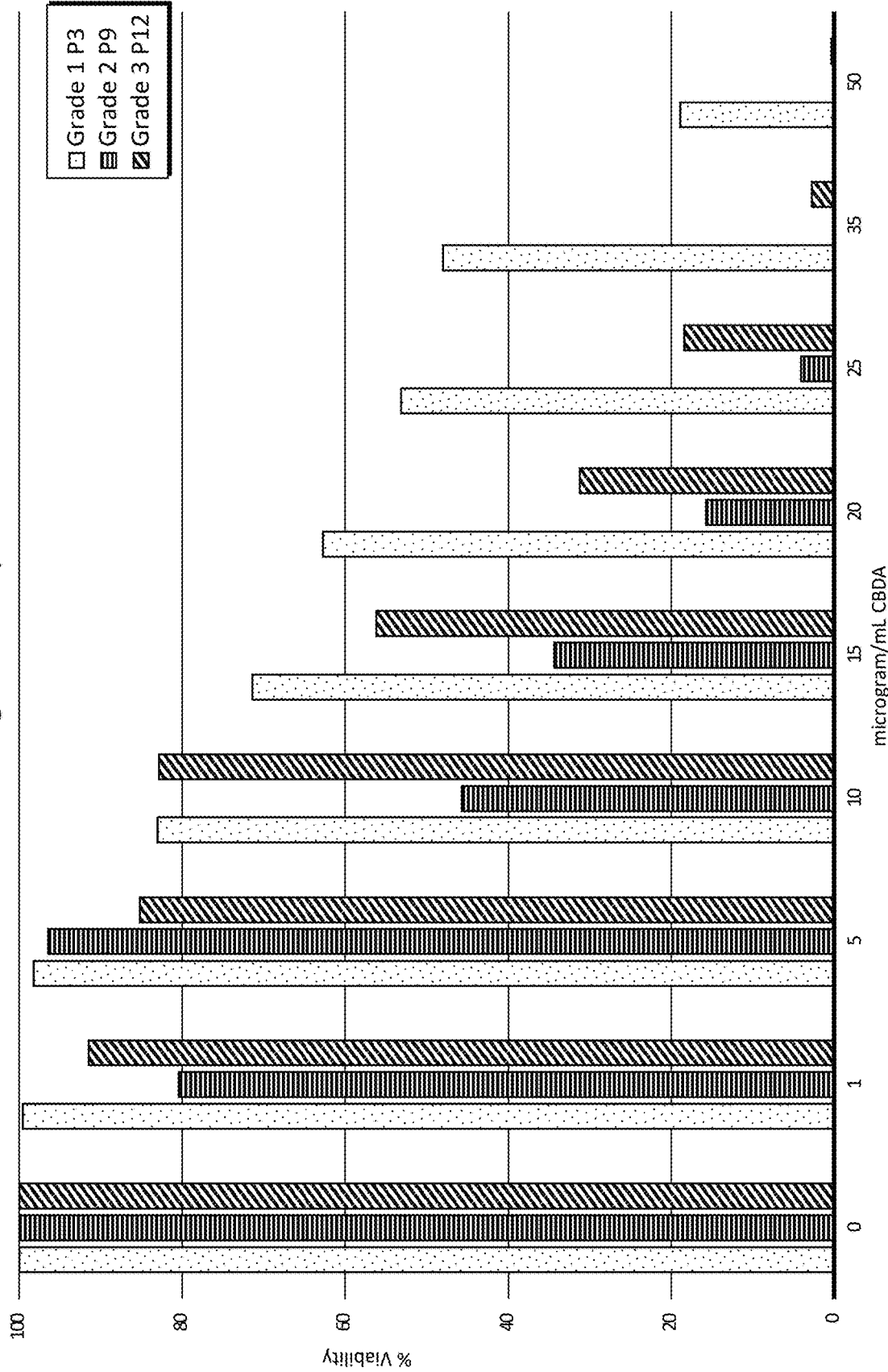

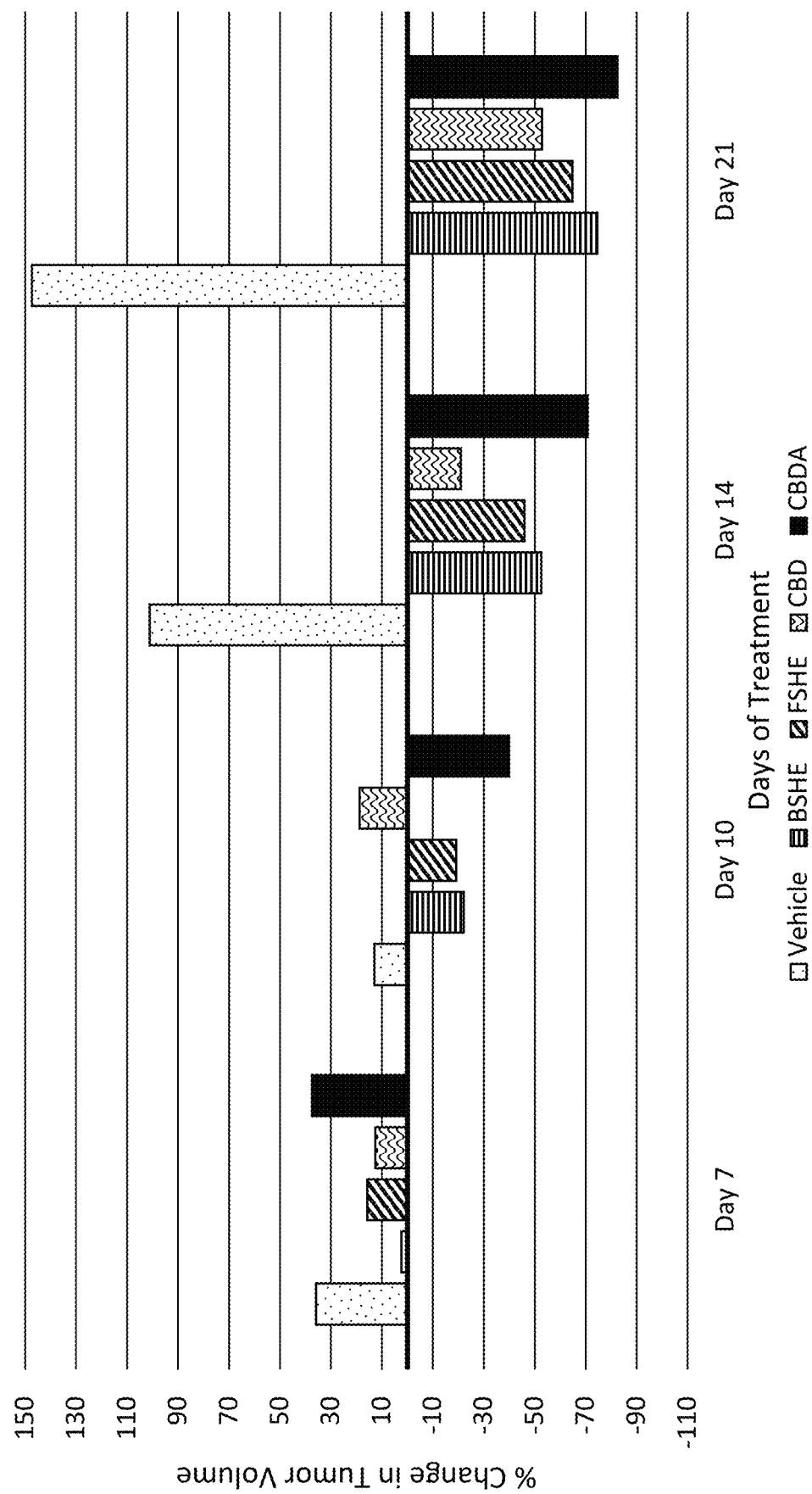

Effects of Paclitaxel and Cannabis Extracts (IC50) + Paclitaxel on Grade 2 Endometrial Cancer Organoids Effects of Paclitaxel and Paclitaxel + Cannabis Extract (IC50) on Grade 3 Endometrial Cancer Tumor Cells

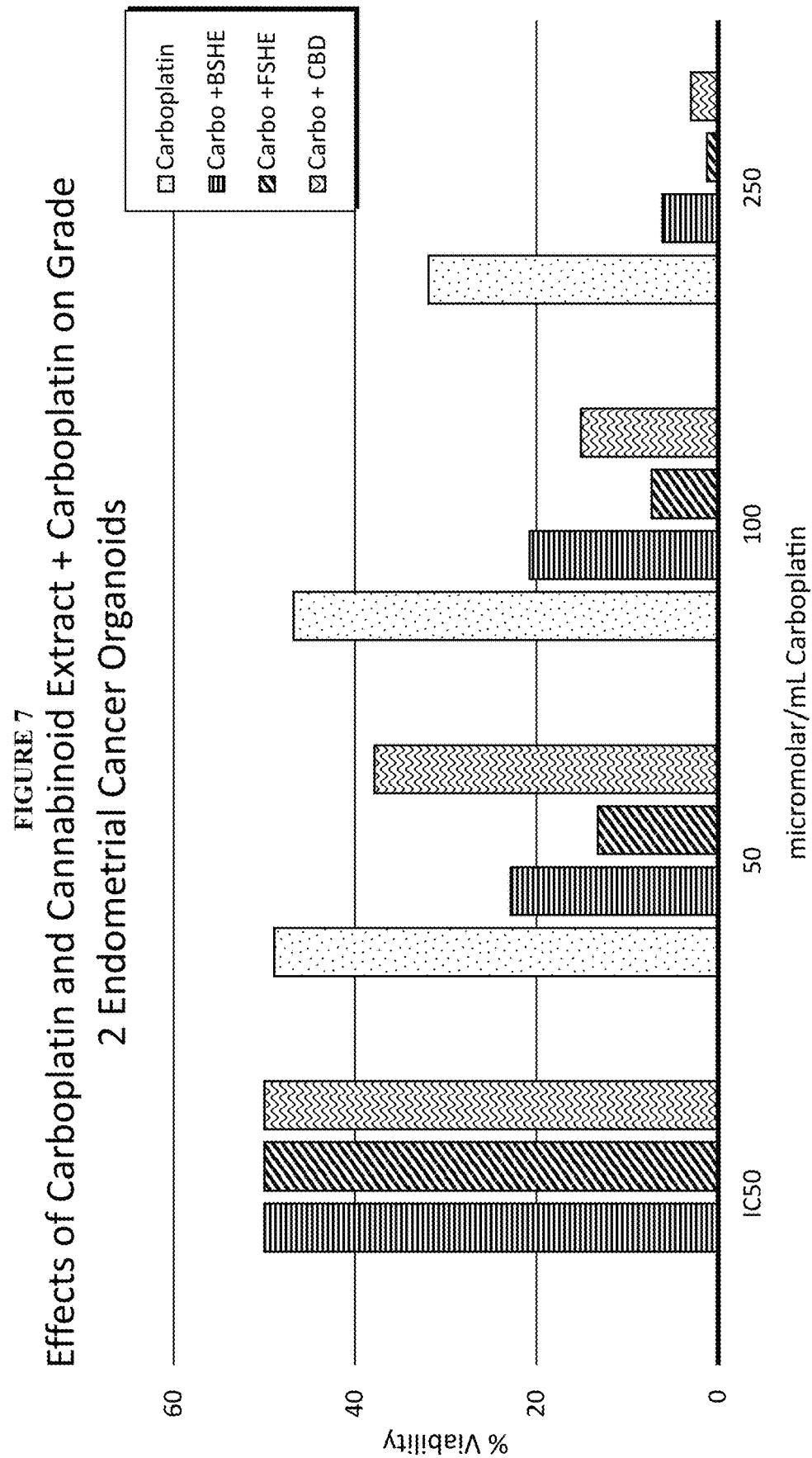

Paclitaxil and Paclitaxil +Cannabinoid Effects on Grade 2 Endometrial Cancer PDX Tumor Volume

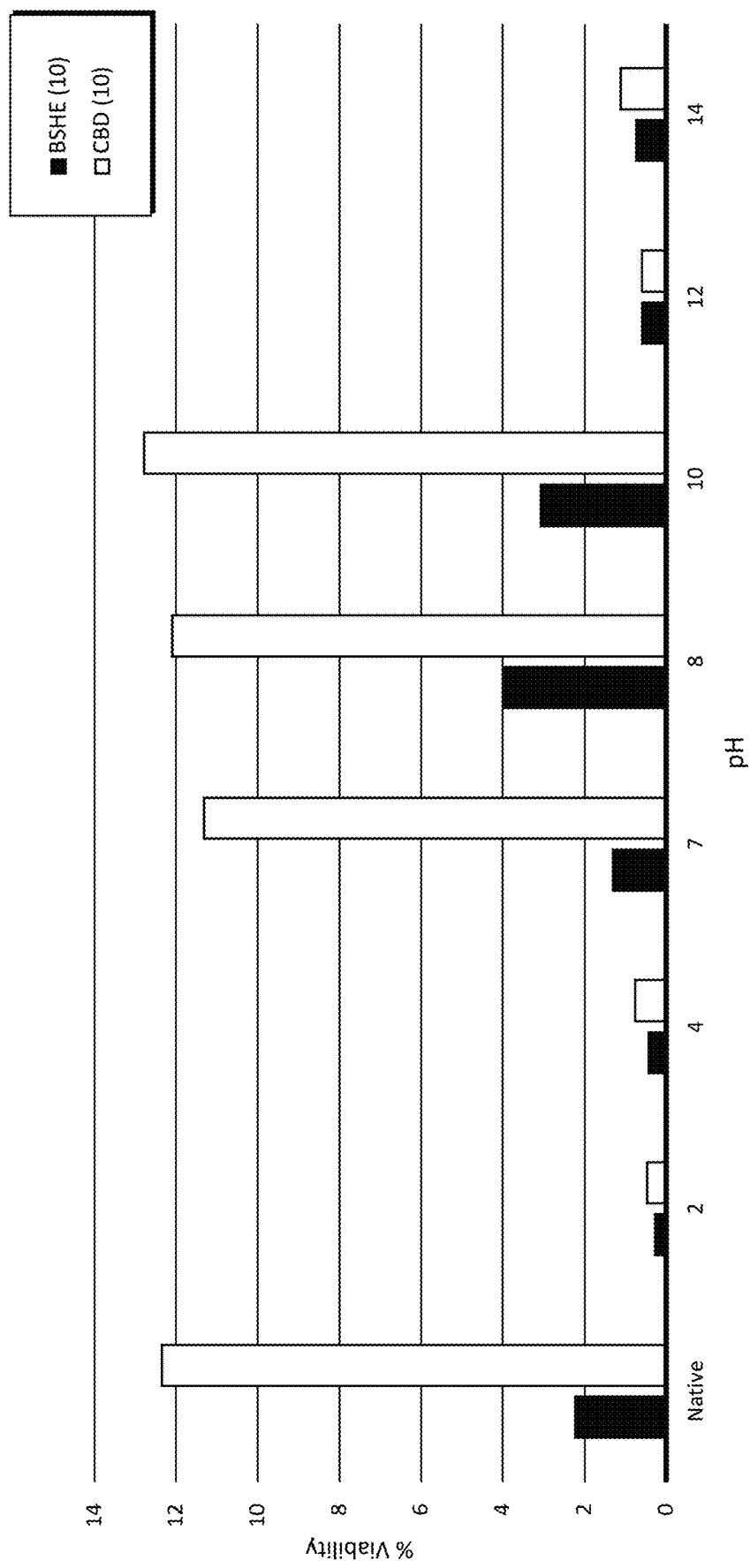

Chemo Sensitive and Chemo Resistant Ovarian Cancer Organoids Response to BSHE

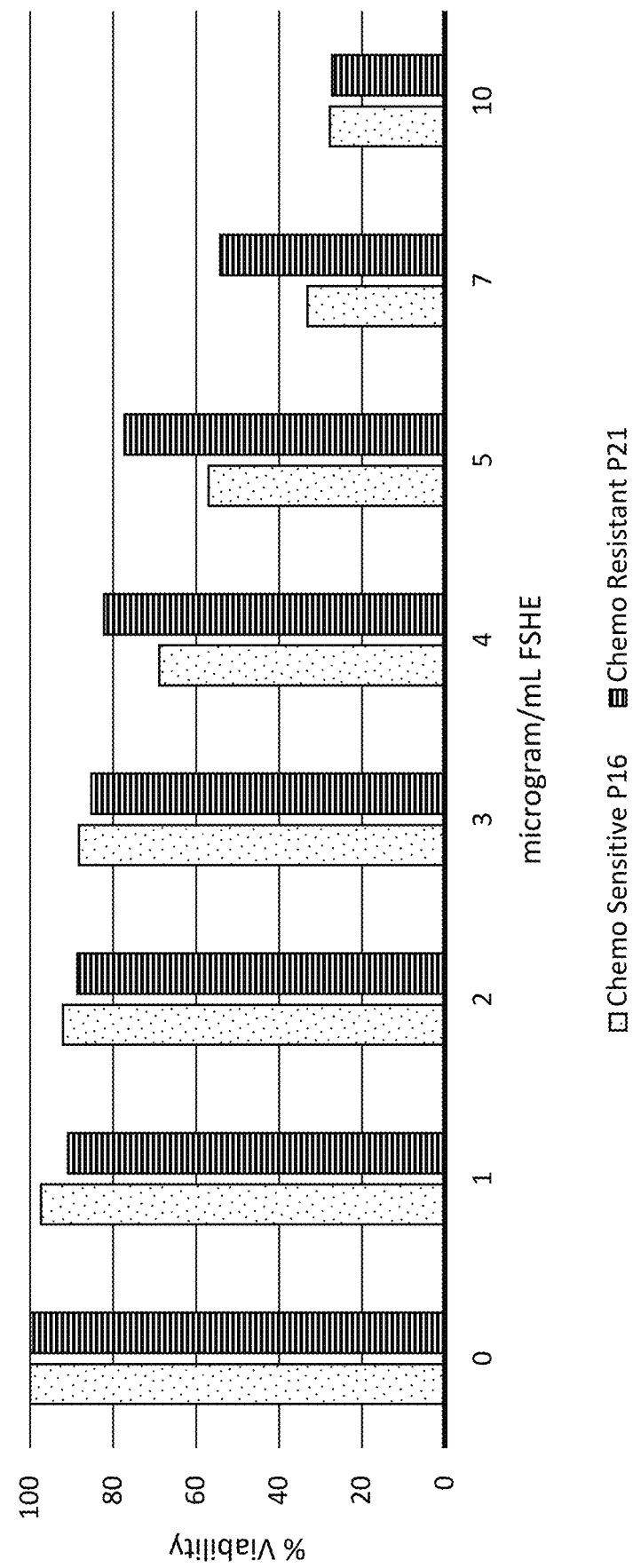

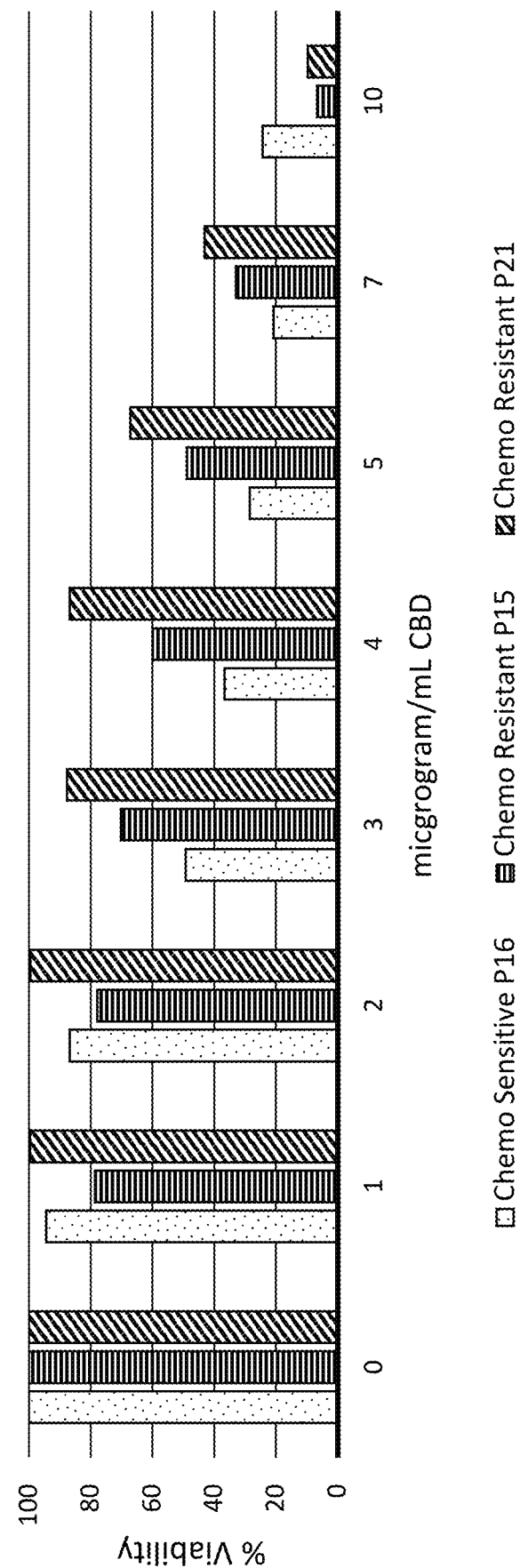

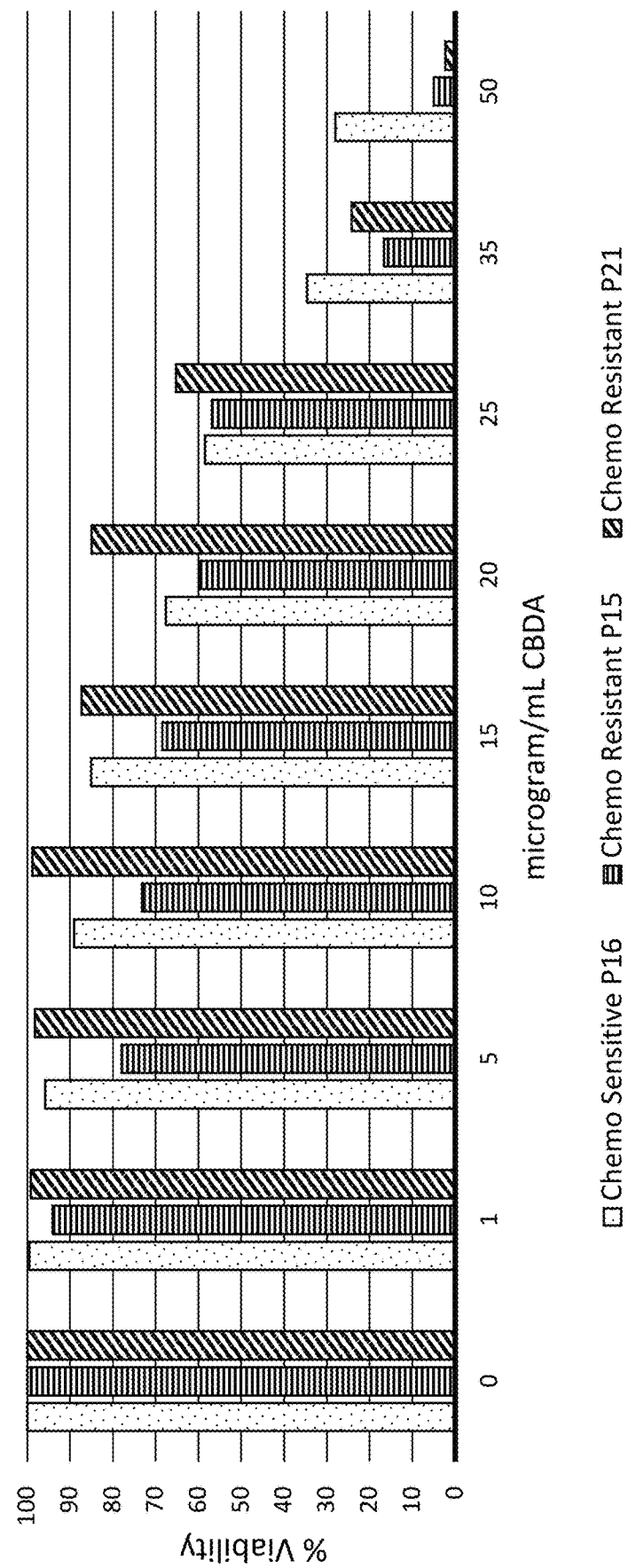

Chemo Sensitve Ovarian Cancer Organoid Response to Paclitaxel and Paclitaxel + Cannabinoid Extract

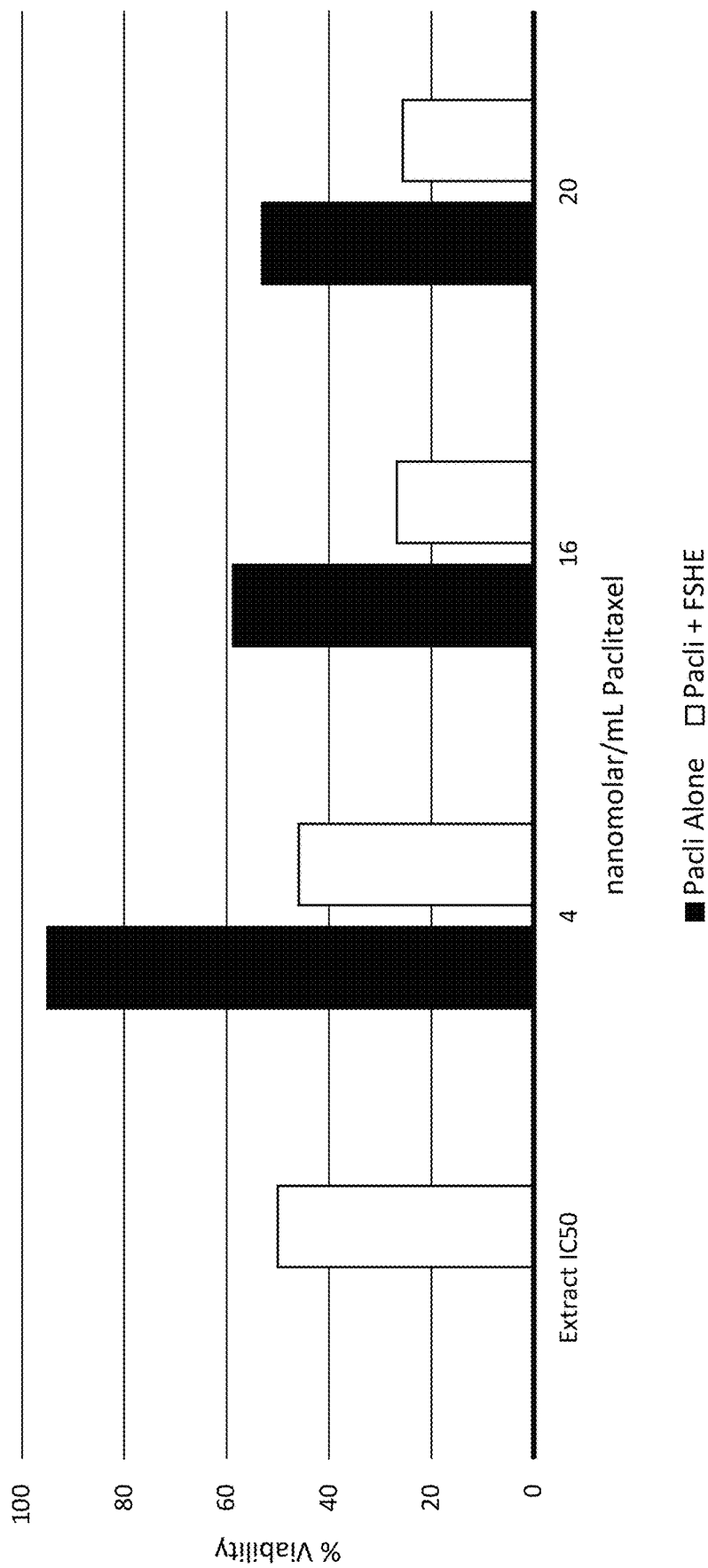

Effect of Antioxidants on Endometrial Cancer Organoid Viability

STABILIZED COMPOSITIONS COMPRISING CANNABIDIOL

CROSS-REFERENCE TO RELATED APPLICATIONS

This application claims the benefit of U.S. Provisional Patent Application No. 63/381,038 filed on Oct. 26, 2022, with the United States Patent and Trademark Office, the contents of which are incorporated herein by reference in their entirety.

FIELD OF THE INVENTION

The inventions disclosed herein are related to delivery methods and compositions for therapeutic compositions and treatments of gynecological disorders and cancers, through administration of an effective amount of *Cannabis* extracts and an antioxidant, alone or in combination with a chemotherapeutic agent. The *Cannabis* extracts comprise one or more cannabinoids, and specifically therapeutic amounts of cannabidiol (CBD) and often include one or more additional cannabinoid, terpene, or other molecules within the *Cannabis* extract, functioning and as the antioxidant.

BACKGROUND OF THE INVENTION

Women face a host of gynecological disorders for which there is currently no adequate method of treatment. These conditions range from non-life-threatening disorders such as polycystic ovarian syndrome and endometriosis to life altering cancers. Cancers may infiltrate any number of cells and organs in the gynecological tract. Unfortunately, many of these cancers are aggressive and have significant risk of metastatic disease.

Cancer represents the phenotypic end-point of multiple genetic lesions that endow cells with a full range of biological properties required for tumorigenesis. Indeed, a hallmark genomic feature of many cancers, including, for example, gynecological cancers such as endometrial cancer, is the presence of numerous complex chromosome structural aberrations, including translocations, intra-chromosomal inversions, point mutations, deletions, gene copy number changes, gene expression level changes, and germline mutations, among others. Whether a cancer will respond to a particular treatment option may depend on the particular genomic features present in the cancer.

Endometrial cancer (EC) is a type of cancer that begins in the uterus, within the layers of cells that form the lining of the uterus. EC is currently the most common cancer of the female genital tract in developed countries. The incidence of EC has continued to increase over more than 50% during the last two decades, with 66,570 new cases and 12,940 deaths recorded in 2021 in the United States alone. Treatment options for EC are currently limited to surgery (hysterectomy and bilaterial salpingo-oophorectomy) followed by adjuvant therapy (chemotherapy or hormonal agents) depending on the clinical and histopathological characteristics of the disease. While primary surgical treatment is beneficial in most patients, about 15-20% of patients develop the recurrent disease even if no symptoms of advanced metastatic disease are present at the time of diagnosis. The chance of recurrence, according to the International Federal of Gynecology and Obstetrics (FIGO), is 10-20% in Stages I-II and 50-70% in stages III-IV.

Ovarian cancer is the second most common gynecologic cancer in the United States and causes more deaths than any other cancer of the female reproductive system. Treatment for ovarian cancer usually involves a combination of surgery and chemotherapy. Unfortunately, as there are no screening options for ovarian cancer, the disease is often detected in later stages of cancer progression and patients are most commonly diagnosed in Stage 3 of ovarian cancer. Stage 3 cancer means that the ovarian cancer cells have spread or grown into nearby organs of the pelvis, and thus the disease is not contained within the ovaries or fallopian tubes. Because of the late stage of diagnosis, and the aggressiveness of ovarian cancer, the five-year survival rate is only approximately 39%. Current treatment options remain inadequate.

In addition to these primary cancers, noncancerous diseases, such as fibroids, dysmenorrhea, endometriosis and others, have significant morbidity, and result in tremendous pain and suffering and accompanying loss of productivity, that primarily impacts pre-menopausal women.

CBD has been suggested as a possible treatment for several different therapeutic treatments. Delivery of CBD to patients typically involves a lipid carrier as CBD is virtually insoluble in water. One of the primary carriers identified in the prior art for CBD is olive oil. Olive oil is readily available and palatable oil, which is compatible with CBD and hemp extracts in general. Olive oil is high in the antioxidant tocopherol which comprises a chromane ring with a hydroxyl group that can donate a hydrogen the atom. For example, WO 2020/0163775 to Alugupalli teaches a nanoemulsion as a carrier with olive oil as a carrier at up to 75% w/v of its nanoemulsion. Alugupalli specifically details the increased efficacy of the olive oil nano emulsion to a control without a carrier.

Another reference, WO 2020/0194237 to Koren teaches the use of cannabinoids, within a carrier or as an excipient that may include cocoa butter, as well as a number of different edible oils such as peanut oil, cottonseed oil, safflower oil, sesame oil, olive oil, corn oil, and soybean oil.

A further reference Ser. No. 17/640,473 to Goldner teaches a cannabinoid-containing additive that uses a carrier oil, and forming an oil and water emulsion to carry the cannabinoid molecules. Again, Goldner teaches that optimal oils are edible oils such as coconut oil, olive oil, soybean oil, grapeseed oil, and avocado oil.

A further reference, entitled Cannabidiol enhances cytotoxicity of anti-cancer drugs in human head and neck squamous cell carcinoma, to Go, doi.org/10/1038/s41598-020-77674-y, suggests cytotoxic effects through administration of CBD. However, Go shows that CBD (dehydrated and re-suspended in ethanol) in treatment is only suitable to reduce the rate of growth, when used alone or in combination with cisplatin or paclitaxel. Go does not teach the actual destruction of cancerous cells.

Thus, the prior art, in just a few of the many examples, chooses to frequently place CBD into an oil win water emulsion, or to simply dissolve cannabinoids into an edible oil for therapeutic use. A hallmark of these edible oils is frequently the presence of vitamin E, or tocopherol. Tocopherol has the following chemical structure:

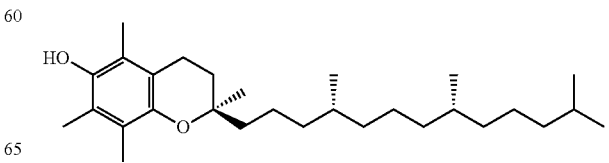

However, few studies, if any, have looked into the possible interaction of these oils, and specifically their components, with cannabinoids and their possible impact on the proliferation of cancerous tissue growth. However, at least one has recently indicated that tocopherol had anti-antiproliferative effects, meaning it rescued cancer cells from apoptosis. www.mdpi.com/1424-8247/15/3/366.

Applicant has surprisingly found that common carries have a deleterious impact on the efficacy of CBD for treatment of cancerous and noncancerous lesions, and that the inclusion, specifically of some of the common excipients and carriers may increase the total growth of and rate of growth of cancerous and noncancerous lesions. By contrast, the unexpected find that specific structures of antioxidants provide for significant increases in efficacy of the CBD. The implications for these exciting discoveries is that the common use of certain materials should be contraindicated when use of CBD is provided for therapeutic use, while inclusion of others generates an unexpected synergy for therapeutic use. Applicant therefore details certain compositions and methods of treatment of noncancerous gynecological disorders as well as gynecological cancers and estrogen sensitive cancers, wherein *Cannabis* extracts are combined with a flavonoid, can be used alone or with concurrent therapeutic molecules, such as a chemotherapeutic agent, to increase effectiveness of the chemotherapeutic agent. These and other embodiments are detailed with more particularity herein.

SUMMARY OF THE INVENTION

In a preferred embodiment, a composition for treatment of noncancerous gynecological disorders or gynecological cancers comprising cannabidiol at between 50 and 99.9% by weight of the composition and a flavonoid at between 0.1 and 50% by weight of the composition.

In a further embodiment, the composition wherein the cannabidiol is provided from a full spectrum hemp extract (FSHE), a broad spectrum hemp extract (BSHE), a CBD isolate, and cannabidiolic acid (CBDA), and combinations thereof.

In a further embodiment, the composition wherein the cannabidiol is provided from a BSHE or FSHE, and which comprise (i) from 50% to 99.9% by weight of CBD and (ii) at least one other cannabinoid selected from Δ-9-tetrahydrocannabinol (Δ9-THC), tetrahydrocannabinolic acid (THCA), tetrahydrocannabivarin (THCV), Δ-8-tetrahydrocannabinol (Δ8-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

In a further embodiment, the composition wherein at least a portion of the CBD is synthetic.

In a further embodiment, the composition wherein the flavonoid is a flavonol, a flavononol, or a flavone.

In a further embodiment, the composition wherein the flavonoid has a concentration of at least 50 μM; and more preferably at least 150 μM.

In a further embodiment, the composition wherein the flavonoid has the following structure:

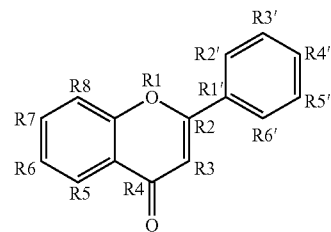

wherein attached at R3 is either a hydrogen or a hydroxyl and attached at least one of R5, R6, R7, R8, R2', R3', R4', R5', and R6' is a hydroxyl.

In a further embodiment, the composition wherein a hydroxyl group is attached at at least two of R5, R6, R7, R8, R2', R3', R4', R5', and R6'.

In a further embodiment, the composition wherein the flavonoid is selected from the group consisting of: myricetin, chrysin, taxifolin, galangin, quercetin, luteolin, 3-hydroxyflavone, and combinations thereof.

In a further embodiment, the composition which is substantially free of tocopherol; and/or contains no measurable tocopherol; and/or preferably is substantially free of beta-caryophyllene.

In a further embodiment, the composition which is suitable for administration orally, rectally, via an oral mucosa, vaginal mucosa, or nasal mucosa, dermally, subcutaneously, intravenously, and/or provided as a first and second dose via the same or different route of administration.

In a further embodiment, the composition where in the ratio of the cannabidiol to the flavonoid is 5 μg/mL: 1 μM to 5 μg/mL:200 μM, and all ratios in between.

In a further embodiment, the composition further comprising a chemotherapeutic agent; preferably, wherein the chemotherapeutic agent is selected from the group consisting of: paclitaxel, carboplatin, doxorubicin, cisplatin, docetaxel, and the combined therapy of carboplatin or cisplatin with paclitaxel, altretamine, capecitabine, cyclosphosphamide, etoposide, gemcitabine, ifosfamide, itinotecan, melphalan, pemetrexed, topotecan, binorelbine, fluorouracil, methotrexate, cetuximab, and combinations thereof.

In a further embodiment, the composition wherein the composition comprises a carrier; and the composition has a pH of between 3.5 to 6.

In a preferred embodiment, use of the composition in treating a noncancerous gynecological disorder selected from the group consisting of an ovarian endometrioma, a deep endometriosis, dysmenorrhea, fibroids, and combinations thereof; and/or use of the composition for treatment of endometrial cancer, ovarian cancer, an estrogen sensitive cancer, an ER(+) cancer, and combinations thereof. In a preferred embodiment, a method of treatment of a gynecological disease or disorder comprising administering to a patient in need thereof, an effective amount of a composition.

In a preferred embodiment, a composition for treatment of a gynecological disease or disorder comprising a *Cannabis* extract and an antioxidant selected from the group consisting of a flavonol, a flavononol, and a flavone, wherein the *Cannabis* extract is selected from the group consisting of: a broad spectrum hemp extract, a full spectrum hemp extract, a CBD isolated, and combinations thereof; wherein each of the *Cannabis* extracts comprises between 50 and 100% by weight of cannabidiol; and wherein the flavonoid has the structure:

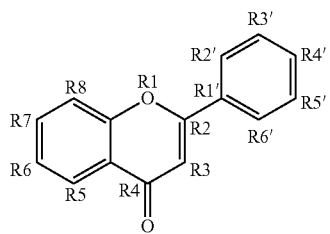

wherein attached at each of R3, R5, R6, R7, R8, R2', R3', R4', R5', and R6' is a hydrogen or a hydroxyl.

In a further embodiment, the composition wherein the flavonoid comprises at least two hydroxyl groups attached at R3, R5, R6, R7, R8, R2', R3', R4', R5', and R6'; and most preferably, wherein attached at R3 is a hydroxyl; and attached at at least two of R5, R6, R7, R8, R2', R3', R4', R5', and R6' are a hydroxyl; and most preferably, wherein attached at at least three of R3, R5, R6, R7, R8, R2', R3', R4', R5', and R6' are a hydroxyl.

In a further embodiment, the composition wherein the ratio of the *Cannabis* extract to the flavonoid is between 5 µg/mL: 1 µM to 5 µg/mL:200 µM, and all ratios in between.

In a further embodiment, the composition further comprising a carrier, wherein the *Cannabis* extract makes up between 50 and 99% by weight of the composition, and the flavonoid makes up between 0.1 and 50% by weight of the composition.

In a further embodiment, the composition wherein the *Cannabis* extract is the carrier.

In a further embodiment, the composition further comprising a chemotherapeutic agent.

In a further embodiment, the composition wherein the *Cannabis* extract comprises at least one other cannabinoid selected from Δ-9-tetrahydrocannabinol (Δ9-THC), tetrahydrocannabinolic acid (THCA), tetrahydrocannabivarin (THCV), Δ-8-tetrahydrocannabinol (Δ8-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

In a preferred embodiment, a method of treatment of endometrial cancer comprising administering to a patient in need thereof, an effective amount of a composition.

In a preferred embodiment, a method of treatment of ovarian cancer comprising administering to a patient in need thereof, an effective amount of a composition.

In a preferred embodiment, a method of treatment of an estrogen sensitive cancer comprising administering to a patient in need thereof, an effective amount of a composition.

In a preferred embodiment, a method of treatment of a noncancerous gynecological disorder selected from the group consisting of: ovarian endometrioma, a deep endometriosis, dysmenorrhea, fibroids, and combinations thereof; the method comprising administering to a patient in need thereof an effective amount of a composition.

In a preferred embodiment, a method of treatment of an estrogen receptor positive disease or disorder comprising administering to a patient in need thereof, an effective amount of a composition.

In a further embodiment, the method wherein the *Cannabis* extract comprises cannabidiol at between 50-99.9% by weight, preferably between 60 and 99.9% by weight, more preferably between 70 and 99.9% by weight, more preferably between 80 and 99.9% by weight, and/or most preferably between 90 and 99.9% by weight. In a further embodiment, the method wherein: (a) the method further comprises administration of the *Cannabis* extract to the patient via an oral dose, oral mucosal dose, intravaginal dose, or combinations thereof; and/or (b) the method further comprises administration of a dose of the *Cannabis* extract to the patient at least once every three days, preferably at least once a day, at least twice a day, or at least three times a day; and/or (c) the method further comprises administration of an amount of the *Cannabis* extract sufficient to generate a concentration of at least 10 µg/mL of the *Cannabis* extract at a target tissue in the patient, preferably wherein the target tissue is a gynecological cancerous tissue; and/or (d) the method further comprises administration of an amount of the *Cannabis* extract sufficient to reach an effective therapeutic level as measured through systemic plasma levels of CBD; and/or (e) the method further comprises administration of between 20 mg and 4,250 mg of cannabidiol to the patient per day; and/or (f) wherein the *Cannabis* extract is formulated within a carrier at an acidic pH, preferably at a pH between 3.5 and 6.

In a further embodiment, the method wherein: (a) the cancer has metastasized; and/or (b) the gynecological cancer is a chemoresistant cancer.

In a further embodiment, the method wherein the method further comprises administering the *Cannabis* extract to the patient via intravaginal administration, preferably wherein: (a) the *Cannabis* extract comprises between 60% and 99.9% CBD; and/or (b) the *Cannabis* extract is selected from a full spectrum hemp extract (FSHE), a broad spectrum hemp extract (BSHE), and a CBD isolate; and/or (c) the *Cannabis* extract comprises CBDA at between 0.1 and 10% by weight.

In a further embodiment, the method wherein the composition comprises (i) a carrier, preferably said carrier comprises an oil or fat and/or (ii) at least one terpene, at least one polyphenol, at least one essential fatty acid, at least one phytonutrient, or a combination thereof, optionally wherein the at least one terpene, at least one polyphenol, at least one essential fatty acid, at least one phytonutrient, or combination thereof make up between 1% and 50% by weight of the total weight of the composition, further optionally wherein: (a) the terpene is selected from β-myrcene, β-caryophyllene, linalool, α-pinene, citral, D-limonene, eucalyptol, and combinations thereof; and/or (b) the essential fatty acid is selected from an omega 3 acid, an omega 6 acid, an omega 9 acid, and combinations thereof; and/or (c) the phytonutrient is selected from a sterol, carotene, an aliphatic alcohol, a mineral, and combinations thereof.

In a further embodiment, the method wherein: (a) the chemotherapeutic agent is selected from paclitaxel, carboplatin, doxorubicin, cisplatin, docetaxel, and the combined therapy of carboplatin or cisplatin with paclitaxel, altretamine, capecitabine, cyclophosphamide, etoposide, gemcitabine, ifosfamide, itinotecan, melphalan, pemetrexed, topotecan, binorelbine, fluorouracil, methotrexate, cetuximab, and combinations thereof; and/or (b) the cancer is a chemoresistant cancer; and/or (c) the method comprises a first step of determining chemoresistance of a cancerous tissue in a patient and a subsequent step of administering to the patient an effective amount of the *Cannabis* extract and an effective amount of the chemotherapeutic agent upon confirmation of chemoresistance; and/or (d) the effective amount of the chemotherapeutic agent is at least 50% less than an indicated dose of the chemotherapeutic agent when administered in the absence of the *Cannabis* extract; and/or (e) the method comprises administering the *Cannabis* extract to the patient in an amount of between 20 mg and 4,250 mg per day.

In a further embodiment, the method wherein the gynecological cancer is a grade 1, grade 2, or grade 3 cancer.

In a further embodiment, the method wherein a chemotherapeutic agent and composition comprising the CE and flavonoid are administered as one composition or as two different compositions.

In a preferred embodiment, a method of treating a gynecological cancer comprising: (a) taking a cancerous cell from a patient and forming an organoid from the cancerous cell; (b) performing a screen on the organoid to determine a chemotherapeutic drug capable of reducing the percent of viable organoids by 50% with an IC50 dose of the chemotherapeutic drug; and (c) administering to the patient the chemotherapeutic drug with an effective amount of a composition comprising a *Cannabis* extract (CE) having between 50% and 99.9% by weight CBD and a flavonoid having a concentration of between 0.1 and 50% by weight.

In a preferred embodiment, a method of treatment of a noncancerous gynecological disorder comprising administering to a patient in need thereof, an effective amount of a *Cannabis* extract and an effective amount of a flavonol, having the structure:

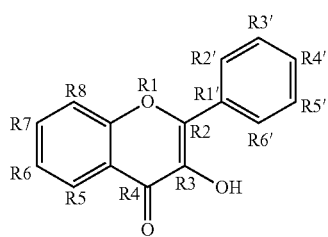

wherein there is at least one hydroxyl group attached at one or more of R5, R6, R7, R8, R2', R3', R4', and R5'.

In a further embodiment, the method wherein a hydroxyl group is positioned at R5 and R7.

In a further embodiment, the method wherein a hydroxyl group is positioned at R5, R7, and at least one of R3', R4', and R5'.

In a further embodiment, the method wherein the *Cannabis* extract is selected from the group consisting of a FSHE, a BSHE, a CBD isolate, or a CBDA isolate.

In a further embodiment, the method wherein the *Cannabis* extract is present at a ratio to the flavonol of between 5 μg/mL:1 μM to 5 μg/mL:200 μM, and all ratios in between.

In a further embodiment, the method wherein the noncancerous gynecological disorder is selected from the group consisting of ovarian endometrioma, a deep endometriosis, dysmenorrhea, fibroids, and combinations thereof.

In a further embodiment, the method wherein the *Cannabis* extract further comprises cannabidiol at between 50 and 99% by weight of the CE, and at least one additional cannabinoid in a concentration of between 0.1 and 10% by weight of the CE, selected from the group consisting of Δ-9-tetrahydrocannabinol (Δ$^9$-THC), tetrahydrocannabinolic acid (THCA), tetrahydrocannabivarin (THCV), Δ-8-tetrahydrocannabinol (Δ$^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

In a preferred embodiment, a method of treatment of a gynecological cancer comprising: administering to a patient in need thereof, a combined therapeutic treatment plan comprising of a chemotherapeutic agent and a composition comprising a *Cannabis* extract and an effective amount of a flavonoid selected from the group consisting of: a flavonol, a flavononol, and a flavone.

In a further embodiment, the method wherein the composition is administered orally, intravaginally, oral mucosally, through the nasal mucosa, dermally, subcutaneously, or through intravenous injection. In a further embodiment, the method wherein the chemotherapeutic agent is administered via the same or a different route of administration to the composition.

In a further embodiment, the method wherein the gynecological cancer is a grade 1, grade 2, or grade 3 cancer.

In a further embodiment, the method wherein the gynecological cancer is a chemoresistant gynecological cancer.

In a further embodiment, the method wherein the gynecological cancer is an endometrial cancer or an ovarian cancer.

In a further embodiment, the method wherein the composition is adjusted to an acidic pH between 3.5 and 6.

BRIEF DESCRIPTION OF THE FIGURES

FIG. 1D depicting the top 20 up and down regulated proteins in ECC treated cells; and FIG. 1E depicting the *Cannabis* extract's effects on signaling and trafficking of various physiological and pathophysiological pathways.

FIGS. 4A, 4B, 4C, and 4D, depict chemosensitive endometrial cancer patient derived organoids, being tested against four different *Cannabis* extracts, namely a broad spectrum hemp extract (BSHE) (FIG. 4A), a full spectrum hemp extract (FSHE) (FIG. 4B), a CBD isolate (FIG. 4C) and CBDA (FIG. 4D).

FIG. 5 depicts a graphical chart of endometrial cancer tumor volumes within mice, wherein the mice were injected with patient derived endometrial cancer cells. The data shows the change in tumor volume from day 7 to day 21 and depicting the therapeutic efficacy of the various *Cannabis* extracts on the tumor volumes.

FIG. 6A is for grade 2 endometrial cancer and FIG. 6B is grade 3 endometrial cancer.

FIG. 7 depicts a combined therapy treatment tested on patient derived endometrial cancer organoids, wherein the chemotherapy agent is carboplatin and is administered with a *Cannabis* extract.

FIG. 9 depicts a chart showing the impacts of pH on therapeutic efficacy of the *Cannabis* extracts.

FIGS. 11A, 11B, 11C, and 11D, depict results from chemosensitive and chemoresistant ovarian cancer patient derived organoids, being tested against four different *Cannabis* extracts, namely a broad spectrum hemp extract (BSHE) (FIG. 11A), a full spectrum hemp extract (FSHE) (FIG. 11B), a CBD isolate (FIG. 11C) and CBDA (FIG. 11D).

FIG. 12A depicts chemosensitive organoids and FIG. 12B depicts chemoresistant organoids.

FIG. 13A details that head and neck cancers showed a viability of about 10% or less at a concentration of 10 µg/mL for two *Cannabis* extracts. Notably, viability at 10% or less is considered at or close to zero, because of the background noise in the assay test. FIG. 13B then shows the use of CBDA, with concentrations at 0, 1, 5, 10, 15, 20, 25, 35, and 50 µg/mL. Again, the results between about 15 and 50 µg/mL are somewhat indistinguishable due to the sensitivity of the counting system at the lowest levels.

FIG. 14 details head and neck cancer organoids response to paclitaxel or a combination of paclitaxel and a *Cannabis* extract, at 4, 16, and 20 nm/ml concentration, with an IC50 dose of the *Cannabis* extract.

FIG. 22B depicts a graphical depiction of response to CBDA for endometrial organoids.

DETAILED DESCRIPTION OF THE INVENTION

Figure 1C:
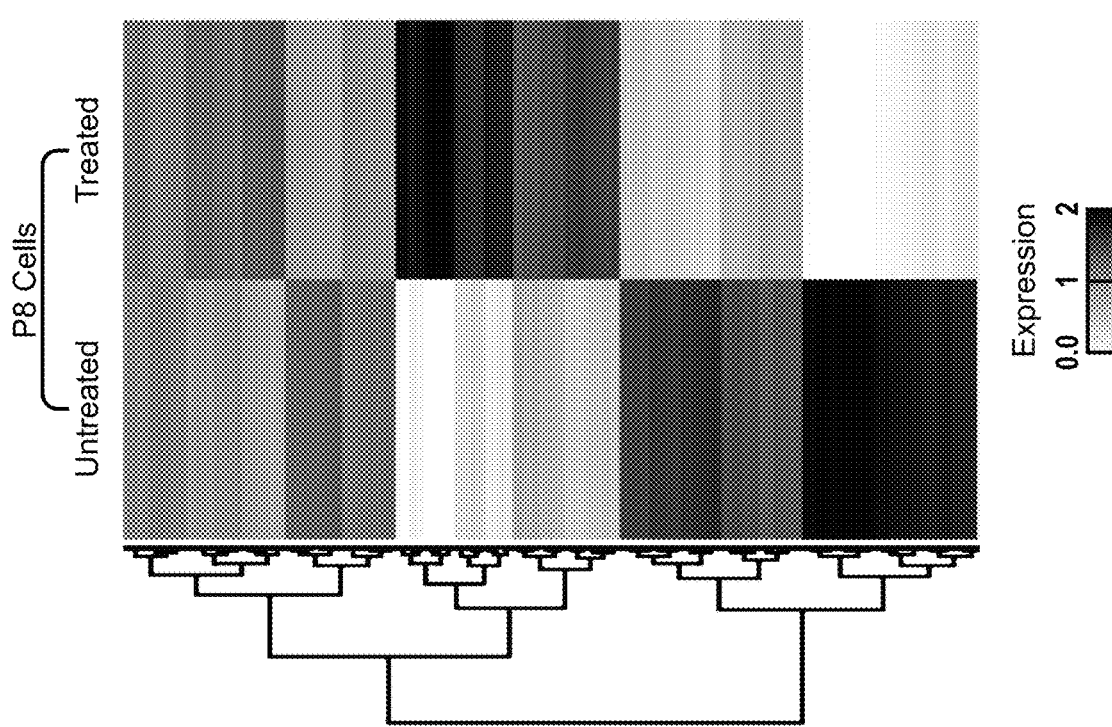
FIG. 1C depicting upregulated and down regulated cells in the vehicle and with a *Cannabis* extract comprising CBD treatment.

As used herein, the term "about" means plus or minus 5% of the numerical value of the number with which it is being used. Therefore, about 50% means in the range of 47.5%-52.5%, or about 100 would mean 95-105.

"Administering" when used in conjunction with a therapeutic means to administer a therapeutic directly to a subject, whereby the agent positively impacts the target. "Administering" the therapeutic drug or compound may be accomplished by, for example, injection, oral administration, topical administration, mucosal administration and/or in combination with other known techniques. The administering techniques may further include heating, radiation, chemotherapy, ultrasound, and the use of delivery agents. Preferably in the present disclosure the administration is through oral, oral mucosal/sublingual, nasal mucosa, intravenous, intramuscular, dermal, intravaginal dosage forms, or other suitable forms of administration. Such intravaginal forms are intended to be inserted into the vagina, typically with a carrier, wherein the active ingredients pass through the vaginal mucosal membrane. The active ingredients may also be provided in an oral form, to be swallowed. Another oral form is an oral mucosal application, which is often provided as a sublingual application, which, while it is ultimately swallowed to enter the stomach, is intended to be held in the mouth, for example under the tongue, and the active ingredients pass through the oral mucosal membrane before being swallowed or passed into the stomach by salivary action or active swallowing of the materials or both, and for nasal mucosa, the material is administered into the nasal passages to allow the therapeutic agents to permeate the nasal mucosa.

By "pharmaceutically acceptable," it is meant that the components including, but not limited to the carrier, diluent, adjuvant, or excipient must be compatible with the other ingredients of the formulation and not deleterious to the recipient thereof.

As used here, the term "composition" is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s) and the inert ingredient(s) that make up the carrier, as well as any product which results, directly or indirectly, from combination, complexation, or aggregation of any two or more of the ingredients or from dissociation of one or more of the ingredients, or from other types of reactions or interactions of one or more of the ingredients. Accordingly, the pharmaceutical compositions of the present invention encompass any composition made by admixing a compound or compounds of the present invention and a pharmaceutically acceptable carrier.

As used herein, the terms "agent," "active agent," "therapeutic agent," or "therapeutic" mean a compound or composition utilized to treat, combat, ameliorate, prevent, or improve an unwanted condition or disease of a patient. Furthermore, the terms "agent," "active agent," "therapeutic agent," or "therapeutic" encompass a *Cannabis* extract and/or additional agents as described in the present disclosure.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue to achieve the therapeutic response. Specifically, the therapeutic shall be effective in treating cancerous or noncancerous growths related to gynecological cancers, estrogen mediated diseases and cancers, and metastatic disease relating thereto.

The terms "treat," "treated," or "treating" as used herein refer to both therapeutic treatment and prophylactic or preventative measures wherein the object is to prevent or slow down (lessen) an undesired physiological condition, disorder, or disease, or to obtain beneficial or desired clinical results. For the purposes of this disclosure, beneficial or desired results include, but are not limited to, alleviation of symptoms; diminishment of the extent of the condition, disorder, or disease such as a reduction in the size of a tumor; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease.

As used here, the term "*Cannabis* extract" (CE) is a composition derived from the *Cannabis* genus of plants (including hemp). A *Cannabis* extract contains cannabinoids with the primary cannabinoid by weight being cannabidiol (CBD). In embodiments a CE may comprise, by weight, between about 1 and 100% CBD (being a refined CBD isolate), preferably between about 20 and 99.9% CBD, more preferably between about 50 and 99.9% CBD, even more preferably between about 70 and 99.9% CBD, and most preferably between about 90 and 99.9% CBD. Synthetically derived CBD may make up all or a part of the percentage of CBD within a *Cannabis* extract. In addition to CBD, embodiments of CE may include at least one additional cannabinoid, typically selected from the group consisting of Δ9-THC, THCA, THCV, Δ8-THC, CBC, CBCA, CBG, CBGA, CBDA, CBDV, CBN, CBL, and combinations thereof. When present in a CE, the at least one additional cannabinoid, or combinations thereof, comprise by weight between about 0.1 and 40% of the CE. Full spectrum hemp extract, broad spectrum hemp extract, CBD isolate, and CBDA isolate are forms of CE utilized herein, as nonlimiting examples of the CE. Throughout the application, the term CBD is often used interchangeably with CE, to mean the CE product containing the particular amount of CBD. In other instances, which are obvious to the reader, the term "CBD" refers to a CBD isolate, which means the CE was processed to separate CBD from virtually all other components of the CE.

As used herein "synthetic cannabinoids" means, those cannabinoid molecules that are synthetically created and not formed from an extraction of a *Cannabis* plant.

As used herein, the term full spectrum hemp extract (FHSE) is a composition derived from the *Cannabis* genus of plants which contains CBD, and quantities of THC ($\Delta^9$-THC, THCA, THCV, $\Delta^8$-THC) above 0, preferably, between 0.01 and 5%, most preferably being between 0.01% and 0.3%. The FSHE may comprise additional cannabinoids, yielding a product that comprises at least 50-99.9% CBD, at least 0.01 to 10% THC ($\Delta^9$-THC, THCA, THCV, $\Delta^8$-THC), and total cannabinoids of between 50% and 99.9% of the weight of the CE.

As used herein, the term broad spectrum hemp extract (BHSE) is a composition derived from the *Cannabis* genus of plants which has undergone at least some purification in order to refine the extract. Typically, a BHSE comprises between 60 and 99.9% CBD and least one additional cannabinoid, selected from the group consisting of A9-THC, THCA, THCV, Δ8-THC, CBC, CBCA, CBG, CBGA, CBDA, CBDV, CBN, CBL, and combinations thereof at between 0.1 and 40%.

As used here, a noncancerous gynecological disorder (NCGD) means a gynecological disorder selected from the group consisting of: endometriosis including ovarian endometrioma or deep endometriosis, dysmenorrhea, fibroids, and combinations thereof.

Cannabidiol has recently begun serious study for potential therapeutic effects. Applicant, however recognized that a disconnect exists in the literature regarding delivery of cannabidiol in an effective manner. Indeed, the prior art generally shows that cannabidiol is ineffective at reducing tumor size, and instead may only be sufficient to delay or reduce the growth rate of tumors or other disease states. Applicant is primarily interested in diseases and disorders related to women's reproductive health, which include NCGD's, gynecological cancers, and estrogen sensitive cancers. A dearth of effective treatments continues confound these diseases and their related co-morbidities.

An association between endometriosis and Endometrial cancer (EC) has been indirectly suggested by epidemiological, biological, and molecular studies, and recent research suggests a genetic basis for overlap. These diseases are often associated with higher levels of estrogen exposure, with a lessened risk related to use of oral contraceptives and progesterone-containing hormonal therapies. Studies have shown endometriosis heritability of approximately 50% and EC heritability of 27%. A review of published SNP's evidence identifies a genetic overlap between endometriosis and endometrial cancer in the genetic correlation analysis, with more SNPs than could expected by chance associated in the same direction of effect. In the cross-disease meta-analysis, after adjustment, 13 SNPs that appeared to be involved in replication. SNP rs2475335, which is located on chromosome 9p23, was most significantly associated with both diseases (P=4.9×10-8). This SNP is housed within the protein tyrosine phosphatase receptor type D (PTPRD) gene. PTPRD deletions and mutations have been found in endometrial tumors. In addition, PTPRD exerts an effect on the STAT3 pathway, which has been identified as relevant to both endometriosis and endometrial cancer.

EC is one of the most frequently diagnosed gynecological cancers worldwide, and its prevalence has increased by more than 50% over the last two decades. Endometrial cancer (also called endometrial carcinoma) starts in the cells of the inner lining of the uterus (the endometrium). This is the most common type of cancer in the uterus. Endometrial carcinomas can be divided into different types based on how the cells look under the microscope. They include: Adenocarcinoma (most endometrial cancers are a type of adenocarcinoma called endometrioid cancer—see below; Uterine carcinosarcoma or CS: Squamous cell carcinoma; Small cell carcinoma; Transitional carcinoma; and Serous carcinoma. Clear-cell carcinoma, mucinous adenocarcinoma, undifferentiated carcinoma, dedifferentiated carcinoma, and serous adenocarcinoma are less common types of endometrial adenocarcinomas. They tend to grow and spread faster than most types of endometrial cancer. They often have spread outside the uterus by the time they're diagnosed.

Most endometrial cancers are adenocarcinomas, and endometrioid cancer is the most common type of adenocarcinoma, by far. Endometrioid cancers start in gland cells and look a lot like the normal uterine lining (endometrium). Some of these cancers have squamous cells (squamous cells are flat, thin cells), as well as glandular cells. There are many variants (or sub-types) of endometrioid cancers including: Adenocarcinoma, (with squamous differentiation); Adenoacanthoma; Adenosquamous (or mixed cell); Secretory carcinoma; Ciliated carcinoma; Villoglandular adenocarcinoma.

Grades 1 and 2 endometrioid cancers are type 1 endometrial cancers. Type 1 cancers are usually not very aggressive and they don't spread to other tissues quickly. Type 1 endometrial cancers are thought to be caused by too much estrogen and sometimes develop from atypical hyperplasia, an abnormal overgrowth of cells in the endometrium. A small number of endometrial cancers are type 2 endometrial cancer. Type 2 cancers are more likely to grow and spread outside the uterus, they have a poorer outlook (than type 1 cancers). Doctors tend to treat these cancers more aggressively. They do not seem to be caused by too much estrogen, i.e., they are not estrogen mediated disease, and thus are often estrogen receptor negative cancers. Type 2 cancers include all endometrial carcinomas that are not type 1, such as papillary serous carcinoma, clear-cell carcinoma, undifferentiated carcinoma, and grade 3 endometrioid carcinoma. These cancers do not look at all like normal endometrium and so are called poorly differentiated or high-grade. Uterine carcinosarcoma (CS) starts in the endometrium and has features of both endometrial carcinoma and sarcoma. (The sarcoma is cancer that starts in muscle cells of the uterus.) In the past, CS was considered a different type of uterine cancer called uterine sarcoma (see below), but doctors now believe that CS is an endometrial carcinoma that's so abnormal it no longer looks much like the cells it came from (it's poorly differentiated). Uterine CS is a type 2 endometrial carcinoma. CS tumors are also known as malignant mixed mesodermal tumors or malignant mixed mullerian tumors (MMMTs). They make up about 3% of uterine cancers.

Despite the understanding of the major signaling pathways driving the growth and metastasis of endometrial cancer, clinical trials targeting these signals have reported poor outcomes. The heterogeneous nature of endometrial cancer is suspected to be one of the key reasons for the failure of targeted therapies. EC is typically understood to be split into four molecular subtypes, including hypermutated cases with POLE mutations and 25-30% harboring a microsatellite instability (MSI) phenotype with mismatch repair deficiency (dMMR). Some of these subtypes are thus treated with PD-1/PD-L1 inhibitors, or with immune checkpoint inhibitors, and other molecules such as pembrolizumab or Lenvatinib. However, these molecules, like first line chemotherapy agents, have high toxicity profiles and thus have significant co-morbidities associated with their use. Furthermore, being targeted, they sometimes miss the heterogeneous nature of the cancer.

For both early stage (Stage I and II EC), and for Stages III and IV EC, first line treatment for EC almost always includes hysterectomy and bilateral salpingo-oophorectomy. In most cases, this is followed by chemotherapy. In view of the significant side effects of chemotherapy, a small portion of stage I and II patients may omit or reduce chemotherapy use as compared to Stages III and IV patients. Chemotherapy is virtually always given to stage III or stage IV EC patients, and often with several rounds of therapy, with the goal of optimizing the risks and the rewards. For Stage III and IV EC, accordingly, organ and tumor removal is typically followed by chemotherapy treatment to capture metastatic disease, as the endometrial cancer cells have often already migrated from the uterus. However, it is well-known that chemotherapy agents are somewhat indiscriminate in their killing, and thus significant secondary impacts occur to the patient leading to impacts on the quality of life. Indeed, even where the chemotherapy is effective in treating the cancer, the toxic effects of the chemotherapy often prove fatal overtime. In virtually all cases, chemotherapy is given in a cycle, meaning a drug or combination of drugs are given for a period of usually 2-6 weeks, and then a rest period, followed by a second or more treatment period. Drugs that are currently utilized for endometrial cancer treatment including but are not limited to paclitaxel, carboplatin, doxorubicin, cisplatin, docetaxel, and the combined therapy of carboplatin or cisplatin with paclitaxel, further agents may also include: altretamine, capecitabine, cyclosphosphamide, ctoposide, gemcitabine, ifosfamide, itinotecan, melphalan, pemetrexed, topotecan, binorelbine, fluorouracil, methotrexate, cetuximab, and combinations thereof.

Chemotherapy drugs typically fall into different classes of drugs, an alkylating agent, an antimetabolite, anti-tumor antibiotics, topoisomerase inhibitors, mitotic inhibitors, DNA repair enzyme inhibitors, plant alkaloids, and antineoplastics. Of the most common chemotherapy drugs for EC, these fall into the following classes: Paclitaxel is an antineoplastic—plant alkaloid; Docetaxel is an antineoplastic—plant alkaloid; Doxorubicin is an antineoplastic—anthracycline antibiotic; Carboplatin is an antineoplastic—alkylating agent and platinum based; and Cisplatin is an antineoplastic—alkylating agent and platinum based. Frequently, paclitaxel is given in combination with one or more of cisplatin or carboplatin. However, while over 60% of EC patients initially respond to platinum-based chemotherapy, the majority relapse, and the term "platinum-resistant" refers to patients with EC who progress within six-months of platinum-based therapy. These patients are at the highest risk for disease related mortality. Even with aggressive treatment and especially when not detected until stage III or IV cancer, EC often metastasizes, leading to low survival rates at 2 and 5 years past initial diagnosis and treatment. Because of the risks associated with chemotherapy, including the toxicity to healthy cells as well as the presence of chemoresistant EC, there is a significant need for new therapeutic treatments including ways to reduce or replace chemotherapy.

Chemoresistance is defined as simply that the cancer cells are resistant to the action of the particular therapeutic agent, such that the disease progresses. Chemoresistant disease may still have some clinical response, but not at sufficient levels to prevent disease progression, or would require such high doses to make the treatment unsuitable. Chemosensitive, therefore being the opposite, wherein the cancer cells in a patient are sensitive to the chemotherapy agent, so that the disease is managed or reduced. However, EC may be, at one point chemosensitive and then later become chemoresistant as treatment progresses through a typical on/off cycle for chemotherapy. This development confounds clinical treatment in many cases highlighting the need for additional and/or new treatments.

Ovarian cancer, while originating from different gynecological cells, has significant overlap with endometrial cancer with regard to treatments. The data herein identifies that CBD, alone, or in combination with a chemotherapeutic agent, is effective for treating both of these disease types. Furthermore, other types of estrogen mediated cancers are also known and many have responses that overlap with both endometrial cancer and ovarian cancer. These include, but are not limited to colorectal cancers, breast cancers, non-cancerous gynecological diseases, such as ovarian endometrioma, a deep endometriosis, dysmenorrhea, and fibroids. These estrogen mediated diseases are frequently treated with an estrogen receptor blocker, or an estrogen blocker (to reduce estrogen production), to reduce the total estrogen as a first line therapy. For cancerous diseases, chemotherapy is typically included within this first line therapeutic protocol. What is clear, is that new methods of treatment and new compositions for treatment are desperately needed.

Cannabidiol has only recently begun detailed study into therapeutic effects for treatment of disease. Typically, cannabidiol is obtained from a *Cannabis* extract, though it may also be manufactured synthetically. Two molecules typically found in *Cannabis* extracts of highest interest are typically cannabidiol (CBD) and Δ-9 tetrahydrocannabidiol (THC). Hemp is defined in the U.S. as a *Cannabis* plant with a Δ-9-THC content of 0.3% or less by dried weight, so it is a political definition and not a scientific definition. The byproducts of hemp plants, including cannabinoids, are federally legal as defined in section 7606 of the 2014 Farm Bill and made permanent in the 2018 Farm Bill.

*Cannabis* extracts can be derived from one or more *Cannabis* plant strains as a source material, or synthetically derived. Leaf and flower from the *Cannabis* plants are extracted to yield the cannabidiol. Notably, while different strains may produce green material with different proportions of desirable compounds, different growing conditions can impact the precise amounts of each compound even for the same strains. *Cannabis* extracts may include isolates of certain compounds, such as isolated CBD, or may include products that contain a wider variety of cannabinoids and other materials, such as those called a full spectrum hemp extract (FSHE) and broad spectrum hemp extract (BSHE), each of which may contain an array of cannabinoids and other phytonutrients such as essential fatty acids, flavonoids, terpenes and essential vitamins and minerals.

Cannabinoids are passed into the body by an advanced physiological system, known as the endocannabinoid system (ECS). This central regulatory system makes cannabinoids inside the body (endocannabinoids) that foster cellular balance throughout nearly every biological system in the body. The ECS is widely distributed throughout the entirety of human physiology and is comprised of three main parts. These are: (i) cannabinoid receptors (CB1 and CB2); (ii) endogenous cannabinoids (endocannabinoids) and most notably anandamide and 2-AG; and (iii) Enzymes that break down endocannabinoids (FAAH and MAGL). Cannabinoid receptors, found on the surface of cells, are widespread throughout the body and listen to the environment around each cell. They transmit information on current conditions to the cell and thereby jump-start the proper cellular response. Properly functioning cannabinoid receptors have the crucial function of creating homeostasis in the body's cells.

CB1 and CB2 receptors are the predominant receptors in the ECS. CB1 receptors are abundant in the brain and central nervous system, whereas CB2 receptors are sparse in the central nervous system but are common throughout the periphery, primarily on immune cells. Cannabinoid receptors are present in almost every organ and organ system throughout the body. They influence activities in the reproductive system, heart, lungs, brain, blood vessels, GI tract, liver, stomach, and more. Cannabinoids, found in hemp (phytocannabinoids), such as CBD, may influence a wide array of bodily functions. These phytocannabinoids interact with the cannabinoid receptors and modulate their activity—while at the same time boosting levels of endocannabinoids. For example, CBD works with the cannabinoid receptors by inhibiting FAAH (Fatty Acid Amide Hydrolase), an enzyme that breaks down the naturally produced endocannabinoid anandamide, thus prolonging its half-life. Anandamide is partially responsible for regulating human reproduction, among its other implications within the body.

A rationale for use of cannabinoids for the treatment of estrogen mediated diseases, gynecological disorders and cancers is that endocannabinoid receptors are abundant in female reproductive organs and the central nervous system. Their signaling and trafficking influence multiple physiological and pathophysiological functions of female reproduction, including folliculogenesis, oocyte maturation, cytoskeleton rearrangement, endometrial cell motility, endometrial migration & proliferation, decidualization, plasticity, and peripheral innervation. Thus, cannabinoids exert antiproliferative effects on deep infiltrating endometriosis, and increased cannabinoid signaling may reduce proliferation of endometriotic lesions, the etiology of which shares some genetic basis and pathophysiological overlap with ovarian and endometrial cancers. Cannabinoid receptors in the pelvis, ovaries, endometrium, vulva and the central and peripheral nervous systems influence inflammation, nociception, and arousal at these therapeutic targets. Cannabinoids trigger localized vasodilation and relaxation of pathological smooth muscle contraction and/or spasticity.

Cannabinoid receptors belong to a superfamily of G protein-coupled receptors. They are single polypeptides with seven transmembrane α-helices, and have an extracellular, glycosylated N-terminus and intracellular C-terminus. Both CB1 and CB2 cannabinoid receptors are linked to GI/O proteins. In addition to these receptors, endogenous ligands for these receptors capable of mimicking the pharmacological actions of THC have also been discovered. Such ligands were designated endocannabinoids and included anandamide and 2-arachidonoyl glycerol (2-AG). Anandamide is produced in the brain and peripheral immune tissues such as the spleen.

Cannabidiol indirectly stimulates endogenous cannabinoid signaling by suppressing the enzyme that breaks down anandamide (fatty acid amide hydroxylase, "FAAH"). CBD also stimulates the release of 2-AG. Therefore, the mechanisms of action for CBD are complex, varied, and still only partially understood. CBD is an antagonist and a partial allosteric modulator of CB1 receptors. There is evidence that CBD stimulates 5HT1A/2A/3A serotonin receptors, TRPV1-2 vanilloid receptors, and glycine channels. CBD does not bind to either CB1 or CB2 receptors and thus most, if not all, of CBDs mechanisms are not directly CB receptor mediated.

Accordingly, CBD may be implicated in multiple signaling pathways in the body. For example, CBD may play a modulatory role with regard to cytokines. Cytokines are signaling proteins synthesized and secreted by immune cells upon stimulation. Accordingly, one of the possible mechanisms of immune control by CBD is by perturbing the balance between cytokines produced by T helper subsets, $T_h1$ and $T_h2$. In certain prior studies, both anti-inflammatory and proinflammatory effects were shown. During chronic inflammation, IL-6 suppression can decrease tissue injury. Cannabinoids, including CBD and THC have been shown to decrease IL-6, TNFα, GM-CSF, and IFNγ. Accordingly, one or more of CBD or THC may be a necessary component in certain applications when a combined effect is necessary to reduce inflammation and decrease pain. Low doses of THC may be suitable to provide these therapeutic effects in combination with CBD.

CBD is also known to stimulate vanilloid pain receptors (TRPV-1 receptor), which are known to mediate pain perception, inflammation, and body temperature. CBD may also impact certain adenosine receptors, which play a significant role in cardiovascular function and broadly impact anti-inflammatory effects throughout the body as well as regulate and decrease anxiety and depression and increase the sense of well-being.

Uptake of phytocannabinoids within the body is confounded by its physical property. Phytocannabinoids are nearly insoluble in water but are soluble in lipids, alcohol, and nonpolar organic solvents, and can also be suspended in emulsions. THC and CBD are both highly lipophilic and have poor oral bioavailability when swallowed, at between 6 to 10 percent, amounts which may be increased through specific preparations. Oral THC formulations exhibit variable absorption and undergo extensive hepatic first-pass metabolism, resulting in lower peak plasma THC concentration relative to inhalation and a longer onset (~120 min) to reach peak concentration. Following oral administration of CBD, a similar plasma concentration-time profile to that of oral THC has been observed. Based on this profile, oral formulations may be useful for patients requiring symptomatic relief over a longer period, though higher concentrations may be necessary, in order to reach therapeutic plasma concentrations, as compared to alternative delivery methods, such as inhalation. Furthermore, certain liver toxicities may exist because of the extensive first pass metabolism when higher dosage amounts are needed for therapeutic levels.

Transdermal administration of cannabinoids, however, avoids first-pass metabolism but the extremely hydrophobic nature and high molecular weights of cannabinoids limits diffusion across the aqueous layer of the dermis. This rate limiting step may only be modified by permeation enhancement, or by enhancement or manipulation of the molecule, such as in delivery tools, or as a pro-drug. Effective dermal transport is typically only obtained by permeation enhancement. However, mucosal transport, either through the oral mucosa, nasal mucosa, vaginal mucosa, or rectal mucosa have different properties as compared to the dermal layer, and thus allow for greater diffusion over these tissues. Even so, in vitro studies with human skin have determined the permeability potential of CBD to be 10-fold higher than that of $Δ^9$-THC and $Δ^8$-THC, consistent with CBD being relatively less lipophilic. This leads to opportunities for CBD for topical administration that are relatively unavailable for $Δ^9$-THC, and which would be further improved for mucosal administration, which does not contain all of the systemic diffusion challenges of overcoming the barrier function of dermal skin layers.

Oral mucosal preparations undergo rapid absorption via the oral mucosa (and hence are useful for symptoms requiring rapid relief), producing plasma drug concentrations higher relative to oral delivery, but reduced relative to inhaled (smoke) consumption of *Cannabis* material. However, even when utilizing oral mucosal preparations, part of the dose will be swallowed and thus ingested via the stomach, thus a portion becoming a standard oral formulation.

Cannabinoids rapidly distribute into well-vascularized organs (e.g., lung, heart, brain, liver), with subsequent equilibration into less vascularized tissue. Distribution may be affected by body size and composition, and disease states influencing the permeability of blood-tissue barriers. Therefore, when targeting less vascularized organs, the distribution and uptake may be reduced, as compared to other organs. This again points to implications for localized administration for EC treatment, instead of simply through the stomach or oral mucosa as with typical applications of therapeutic treatments.

CBD is hepatically metabolized, primarily by isozymes CYP450, CYP2C19 and CYP3A4 and additionally, CYP1A1, CYP1A2, CYP2C9 and CYP2D6. After hydroxylation to 7-hydroxy cannabidiol (7-OH-CBD), there is further hepatic metabolism and subsequent fecal, and, to a lesser extent, urinary, excretion of those metabolites. CBD, like THC, has also been reported to have a long terminal elimination half-life, with the average half-life following intravenous dosing observed to be 24±6 hours and post-inhalation to be 31±4 hours. An investigation of repeated daily oral administration of CBD elicited an elimination half-life ranging from 2 to 5 days. A relatively longer elimination half-life is observed in heavy users, attributable to slow redistribution from deep compartments such as fatty tissues. Indeed, both THC and CBD are known to accumulate in adipose tissues with recurring administration. Consequently, THC and CBD concentrations 1 μg $l^{-1}$ may be measurable in the blood of heavy users more than 24 h following the last *Cannabis* use.

Dose-response and drug-drug interaction information is lacking. Potential exists for pharmacokinetic interactions between both THC and CBD and other drugs, via inhibition or induction of enzymes or transporters and additionally, pharmacodynamic drug-drug interactions. There is a potential for CBD to compete with drugs metabolized through CYP 450 pathways, specifically those that interact with enzymes CYP3A4, CYP2C19, and CYP2D6. Dose adjustments may be necessary with substrates of CYP2C8, CYP2C9, CYP2C19, CYP1A2 and CYP2B6. Notably, the combination composition provided in the embodiments herein are directed towards the inclusion of CBD and a flavonoid (such as a flavonol or a flavone), each of which may be implicated with one or more of the enzymatic materials listed above, and which may, but Applicant does not limit to such, provide the evidence and rational for the unexpected results of the synergistic combination of the CBD and the flavanoid.

*Cannabis* extracts for therapeutic use in the methods herein, are typically generated by an extraction process to remove desired materials from the trichomes and other green material from the hemp plant. Phytocannabinoids are concentrated in a viscous resin that is produced in glandular structures known as trichomes within hemp plants. In addition to cannabinoids, the resin is rich in terpenes, which are largely responsible for the odor of the plants in the *Cannabis* family. These materials are also present in additional tissues of the plant, most notably in the flowers and leaves of the plants. Phytocannabinoids are nearly insoluble in water but are soluble in lipids, alcohol, and nonpolar organic solvents, and can also be suspended in emulsions. For this reason, the prior art often dissolves the cannabinoids into fats and oils, such as vegetable oils. These vegetable oils are highly palpable and can be further flavored to allow for oral administration.

A representative extraction process is enumerated in patent application Ser. No. 18/049,977. The *Cannabis* extracts such as a FSHE or a BSHE further comprise certain amounts of an array of cannabinoids and other phytonutrients such as essential fatty acids, flavonoids, terpenes and essential vitamins and minerals. However, cannabidiol can also be synthetically manufactured.

A representative, nonlimiting sample of the *Cannabis* extract of the present disclosure comprises concentrations of certain compounds within the following ranges:

TABLE 1

CANNABINOID EXTRACT EXAMPLES

| Cannabinoid | BSHE mg/g | BSHE % | FSHE mg/g | FSHE % |
|---|---|---|---|---|
| $\Delta^8$-THC | ND | 0-1 | ND | 0-3.0 |
| $\Delta^9$-THC | ND | 0-0.3 | 25 | 0.01-5.0 |
| $\Delta^9$-THCA | ND | 0-0.3 | ND | 0-1.0 |
| THCV | ND | ND | ND | |
| THCVA | ND | ND | ND | |
| CBD | 900 | 70-99 | 800 | 65-98 |
| CBDA | ND | 0-2.5 | ND | |
| CBC | ND | 0-3.5 | 19 | 0-0.35 |
| CBCA | ND | 0-5.0 | ND | |
| CBDV | ND | 0-2.5 | 8 | 0-2.5 |
| CBG | 15 | 0.1-3.5 | 17 | 0.1-3.5 |
| CBGA | ND | 0-3.5 | ND | |
| CBN | 2.0 | 0.01-0.5 | 1.65 | 0-0.5 |
| Total THC | ND | 0-1.5 | 25 | 0.3-5.0 |
| Total CBD | 900 | 70-99 | 800 | 65-98 |
| Total Cannabinoids | 917 | 71-99 | 870.65 | 65-99.9 |
| Sum of additional Cannabinoids | 0 | 0-10 | 0 | 0-10.0 |

Therapeutic Treatments Comprising CBD and a Flavonoid Antioxidant.

Figure 1A:
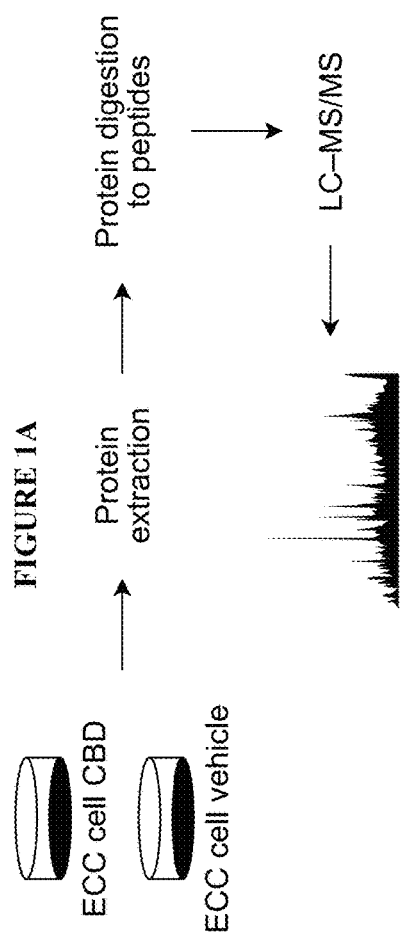
FIGS. 1A, 1B. 1C. 1D, 1E, IF, 1G, 1H, and 1I depict endometrial cancer cells being treated with a *Cannabis* extract comprising CBD, with FIG. 1A showing a diagram of the process of capturing the data regarding protein expression, FIG. 1B depicting protein differentiation numbers.
Figure 1B:
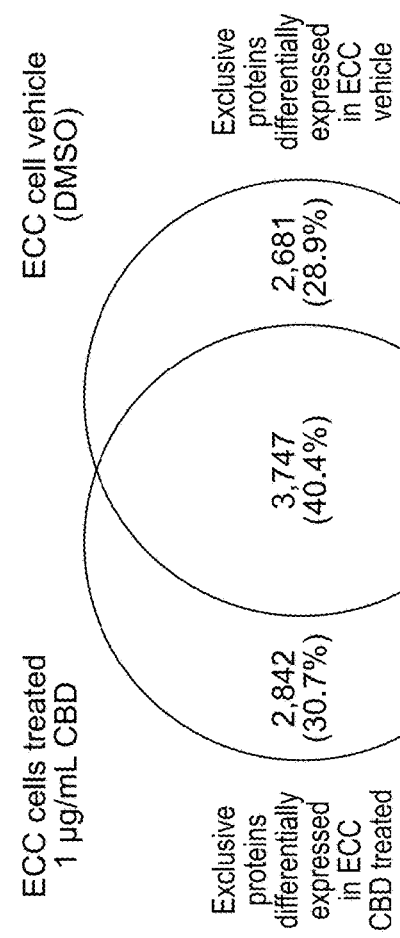

A sample of *Cannabis* extract, using a broad spectrum hemp extract was utilized on endometrial cancer patient derived organoids, to determine efficacy of *Cannabis* extracts on endometrial cancer cells by examining protein expressions. Applicant's prior work detailed a comparison of protein expression in untreated cells as compared to treated cells provides insight as to which proteins change expression in the endometrial cancer cells and which proteins remain the same. With this knowledge, additional, targeted research may ensue. Referring to FIG. 1A, endometrial cancer cells (ECC) were either treated with a CE with CBD (1 μg/mL) or left untreated as a control (vehicle—DMSO). After treatment, proteins were extracted from the test cells and the control cells and digested for analysis by liquid chromatography (LC) tandem mass spectrometry (MS/MS). Referring to FIG. 1B, the Venn diagram shows the results of LC-MS/MS analysis which is that treated cells expressed 2,842 different proteins than untreated cells, untreated cells expressed 2,681 different proteins than treated cells, and treated and untreated both expressed 3,747 common proteins. Clearly, based on protein expression differences, treatment with as little as 1 μg/mL CE with CBD had a clear impact on proteins that were exclusively expressed and proteins that were no longer expressed. FIG. 1C compares the degree to which certain proteins were expressed (or not expressed) in untreated cells and treated cells.

Referring to FIG. 1D, of the thousands of proteins that were differentially expressed with treated and untreated cells, the top 20 upregulated (e.g., in treated cells only) and downregulated (e.g., in untreated cells only), are identified and enumerated. Now referring to FIG. 1E, the effect of treatment with CE with CBD on signaling and trafficking of various physiological and pathophysiological pathways is shown. As one example, proteins associated with Endocannabinoid Neuronal Synapse are shown to be upregulated in untreated cells and downregulated in treated cells.

Figure 1F:
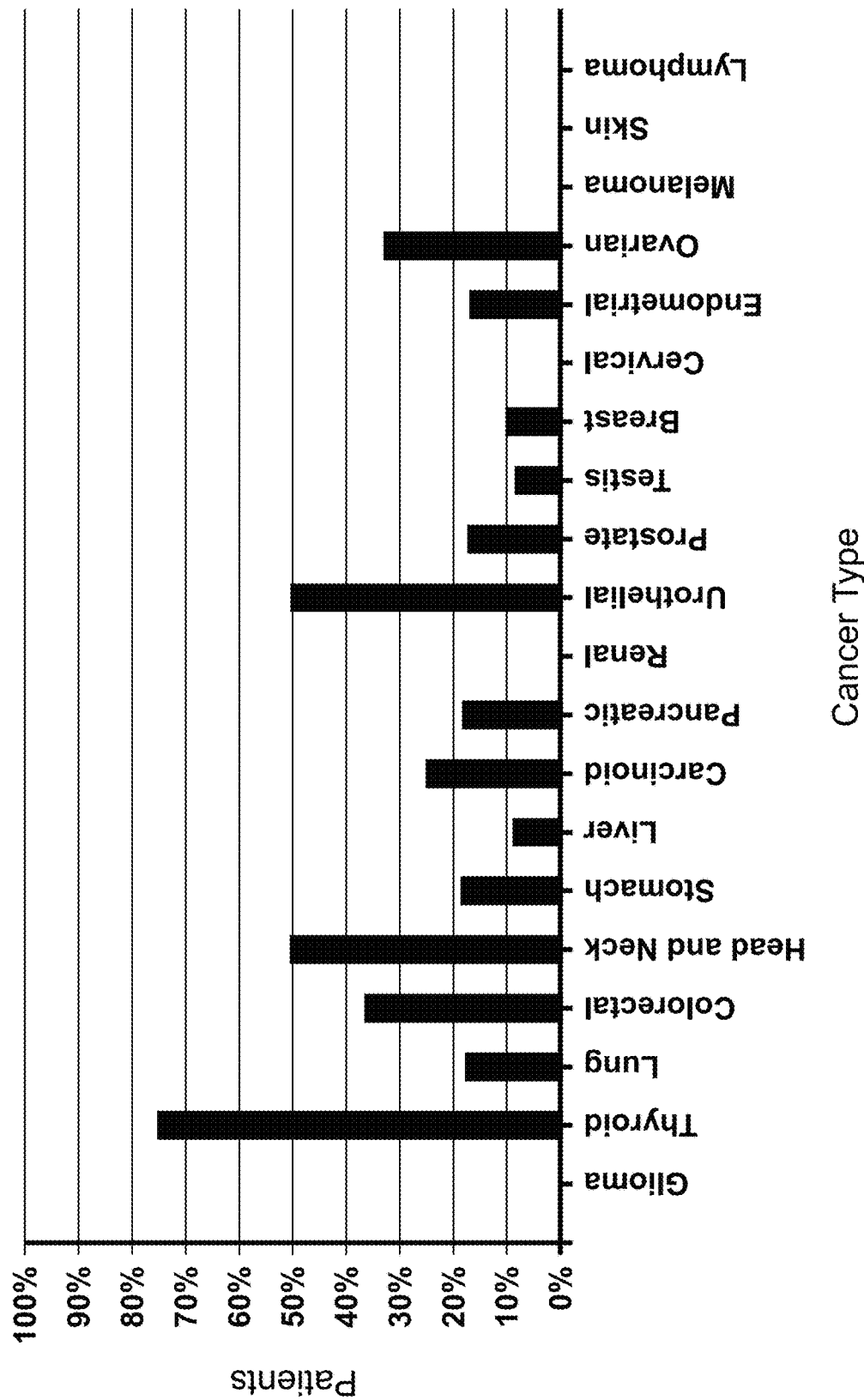
FIG. 1F depicts the percent of patients in which CB1 receptors are implicated in progression or management of the disease.
Figure 1G:
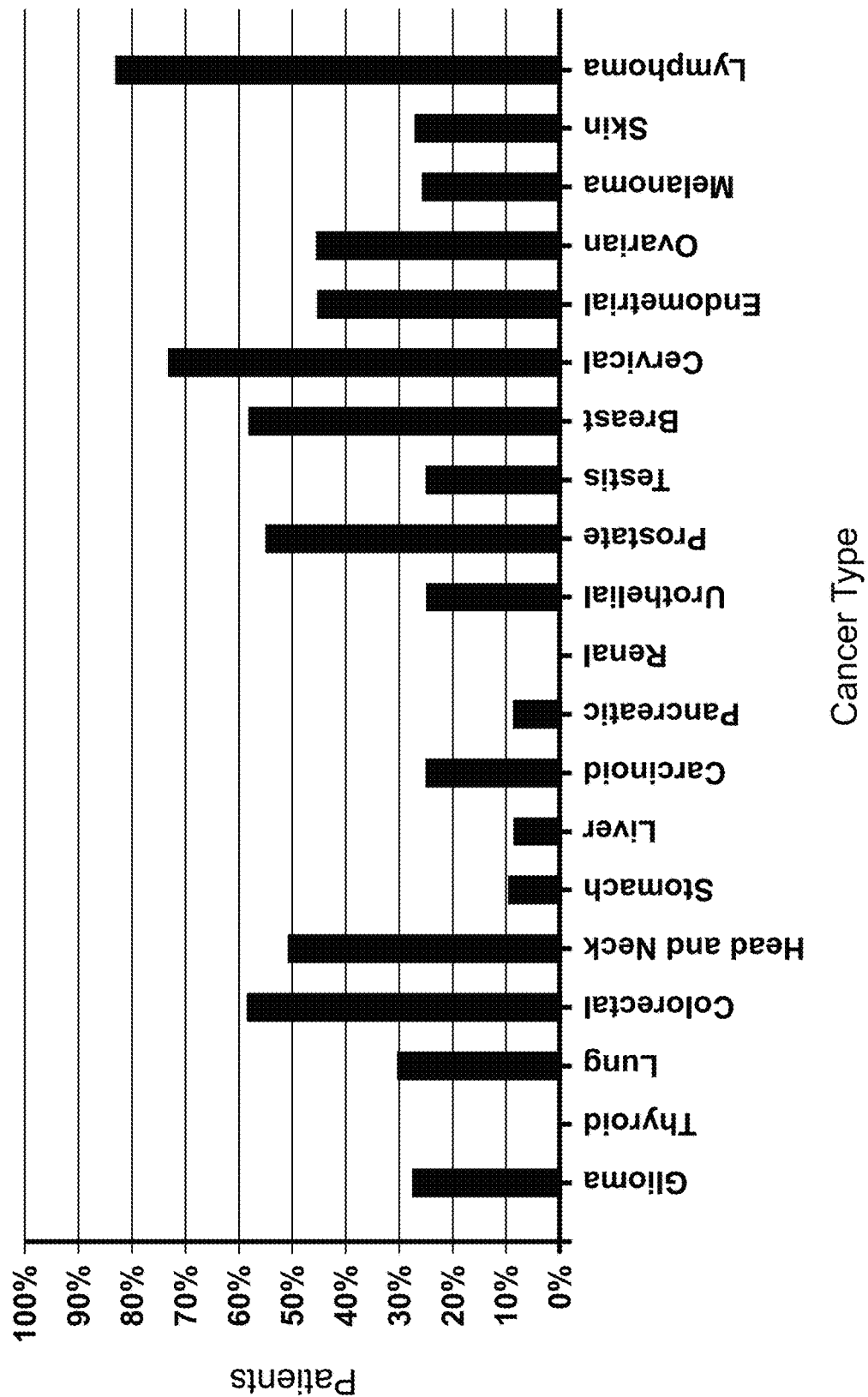
FIG. 1G depicts the percent of patients in which Cannabinoid receptor 2 is implicated in progression or management of disease.

FIGS. 1F and 1G depict that cannabinoid receptors 1 and 2 have significant overlap with regard to the percentage of patients wherein the receptor is implicated in the cancer. Many of these cancers are gynecological, and thus form a significant basis for the determination that use of and treatment of gynecological cancers can be treated with CE comprising CBD.

Figure 1H:
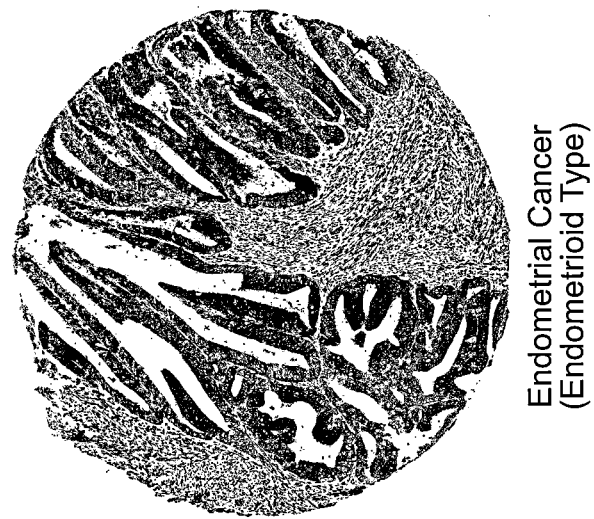
FIG. 1H, depicts cannabinoid receptor 1 protein expression in an endometrial cancer cell.
Figure 1I:
FIG. 1I depicts cannabinoid receptor 2 protein expression in an endometrial cancer cell.

Lastly, referring to FIG. 1H, a tissue sample taken from a patient with endometrial cancer was selectively stained to show CB1 receptor expression. FIG. 1I is a similar tissue sample selectively stained to show CB2 receptor expression.

In view of the strong protein differentiation due to CBD treatment, further testing was warranted to determine efficacy of CBD as a mono therapy or combined therapy towards certain cancerous or estrogen mediated diseased cells. Applicant tested different concentrations of CBD in each of the doses with DMSO as the vehicle for all tests. Each of the tests were run in at least triplicate, including the carrier alone. Initial tests started at 250 μg/mL, which was 100% effective in killing the endometrial cancer organoids. Subsequently, 100 μg/ml was also tested and also was 100% effective in killing the endometrial cancer organoids. Finally, tests of 50, 25, 10, and 1 μg/mL were compared to the control. Notably, both the vehicle/control and the 1 μg/ml concentration were unable to destroy the cancer cells, but at a concentration as low as the 10 μg/ml, and including higher doses at 25 and 50 μg/ml, the BSHE was able to completely kill the organoid based cancer cells. These doses can then be calculated to yield an equivalent CBD dose to a patient of 1 μg/mL is a dose of approximately 20 mg a day of CBD, 10 μg/mL is approximately 200 mg a day, 25 μg/mL is approximately 500 mg a day, and 50 μg/mL is approximately 1000 mg a day, if provided as a human equivalent dose. Currently, for example, the prescribed CBD isolate is given at a dose of between 5 and 50 mg of CBD/kg and in the United States an average weight of between 65 and 85 kg, yields doses of between 325 to 4250 mg a day of CBD. Applicant's actual tests, therefore, range from well below these doses to about ¼ of the acceptable dose. Applicant believes that the higher end of the human dosing range is fully appropriate in this case as well, which would replicate tests at 100 μg/mL or higher, as the alternative to such CBD dose is almost always chemotherapy, which will have a significantly worse side effect profile at virtually any concentration, than the highest doses of CBD.

These results confirm that CBD may have therapeutic use for certain diseases. Applicant repeated testing and used different doses to determine if a lower dose would also continue to be effective for additional samples. Furthermore, different sets of donor cells were utilized for creating patient derived organoids, based upon the grades of EC, because we wanted to identify whether the *Cannabis* extract comprising CBD would remain effective for grades, 1, 2, and 3 EC, among larger patient populations and at potentially lower doses. Notably, grades 1 and 2 EC are ER(+), while grade 3 was ER(−), and whether these different estrogen receptor status would implicate different treatments or different protocols for the greatest efficacy.

Figure 2:
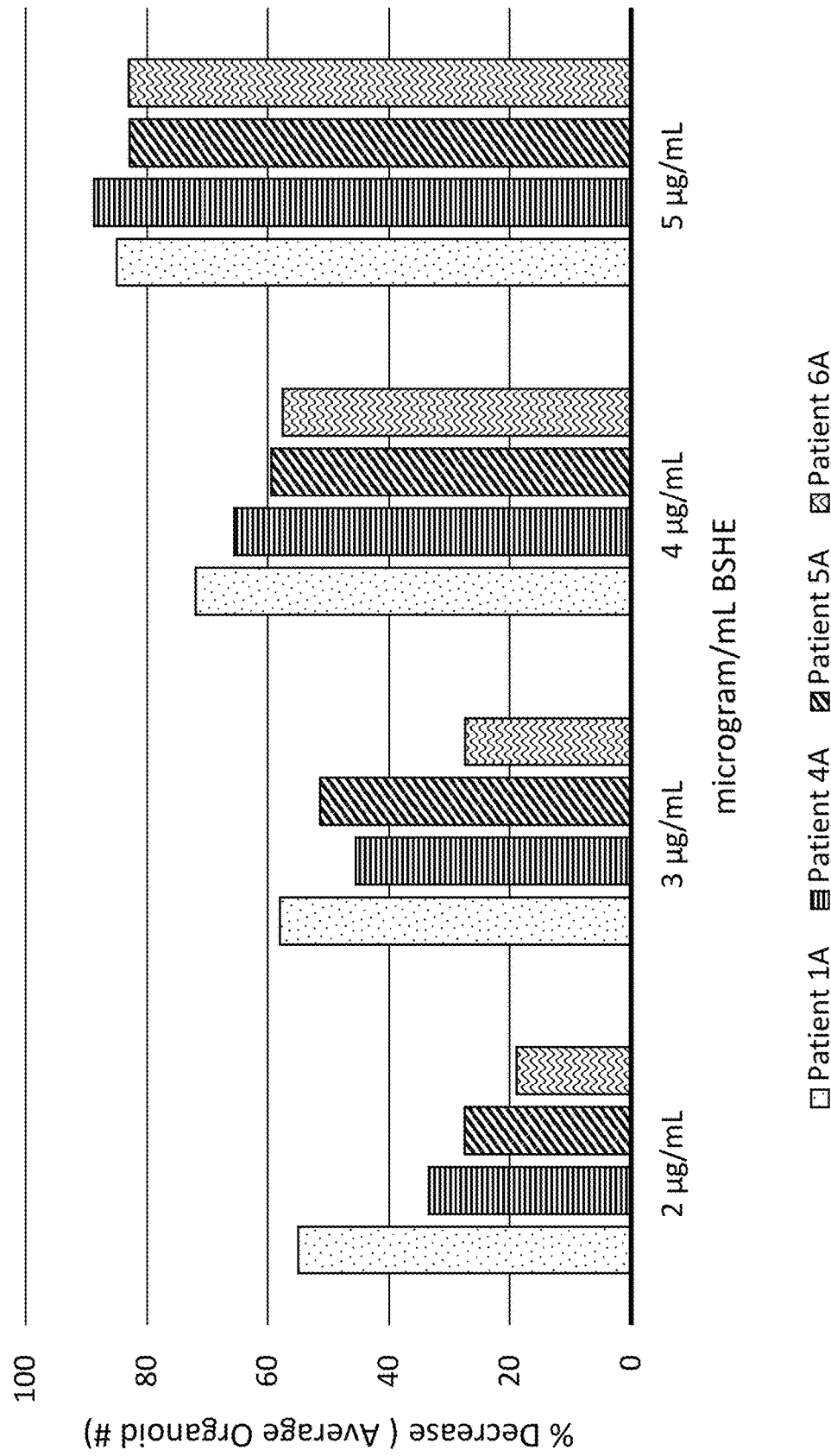
FIG. 2 depicts the decrease in in organoid number compared to the vehicle for endometrial cancer organoids treated with different concentrations of hemp extract including 2, 3, 4, and 5 μg/mL.
Figure 3A:
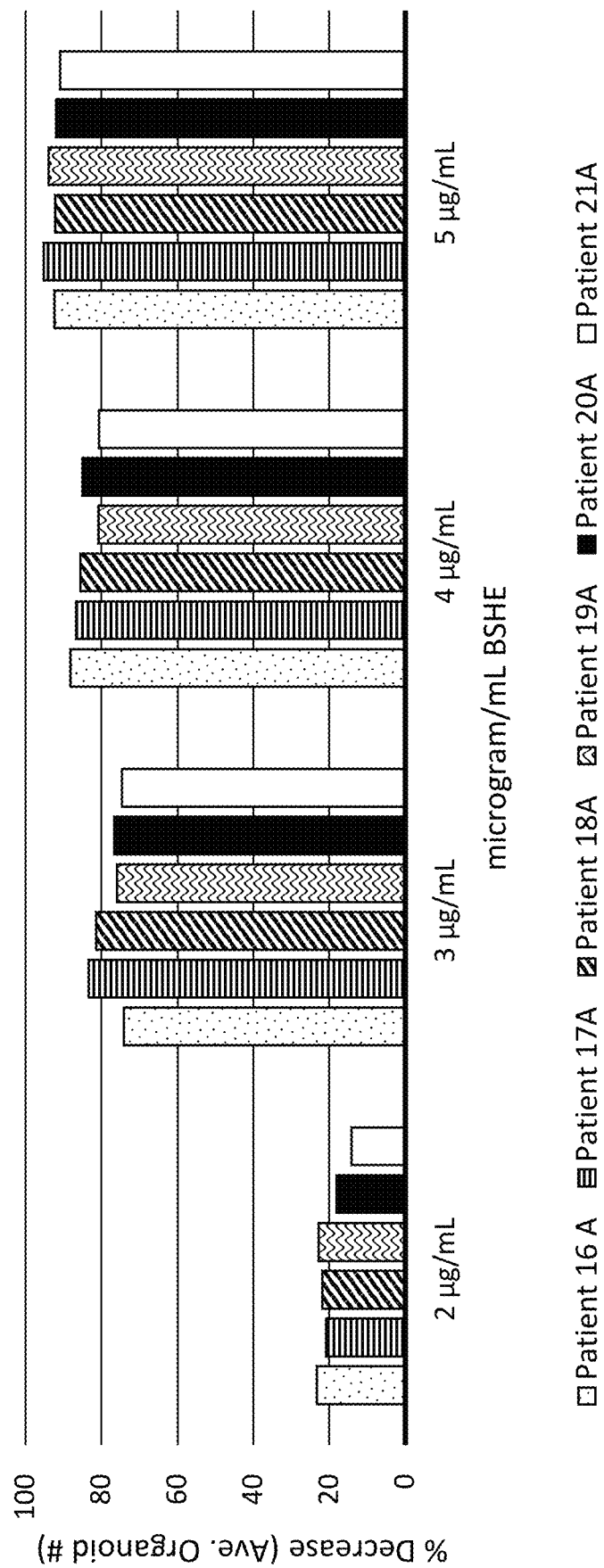
FIGS. 3A and 3B depict a grade 3 endometrial cancer organoid tested in two trials at concentrations of 2, 3, 4, 5, 7, and 10 μg/mL.
Figure 3B:
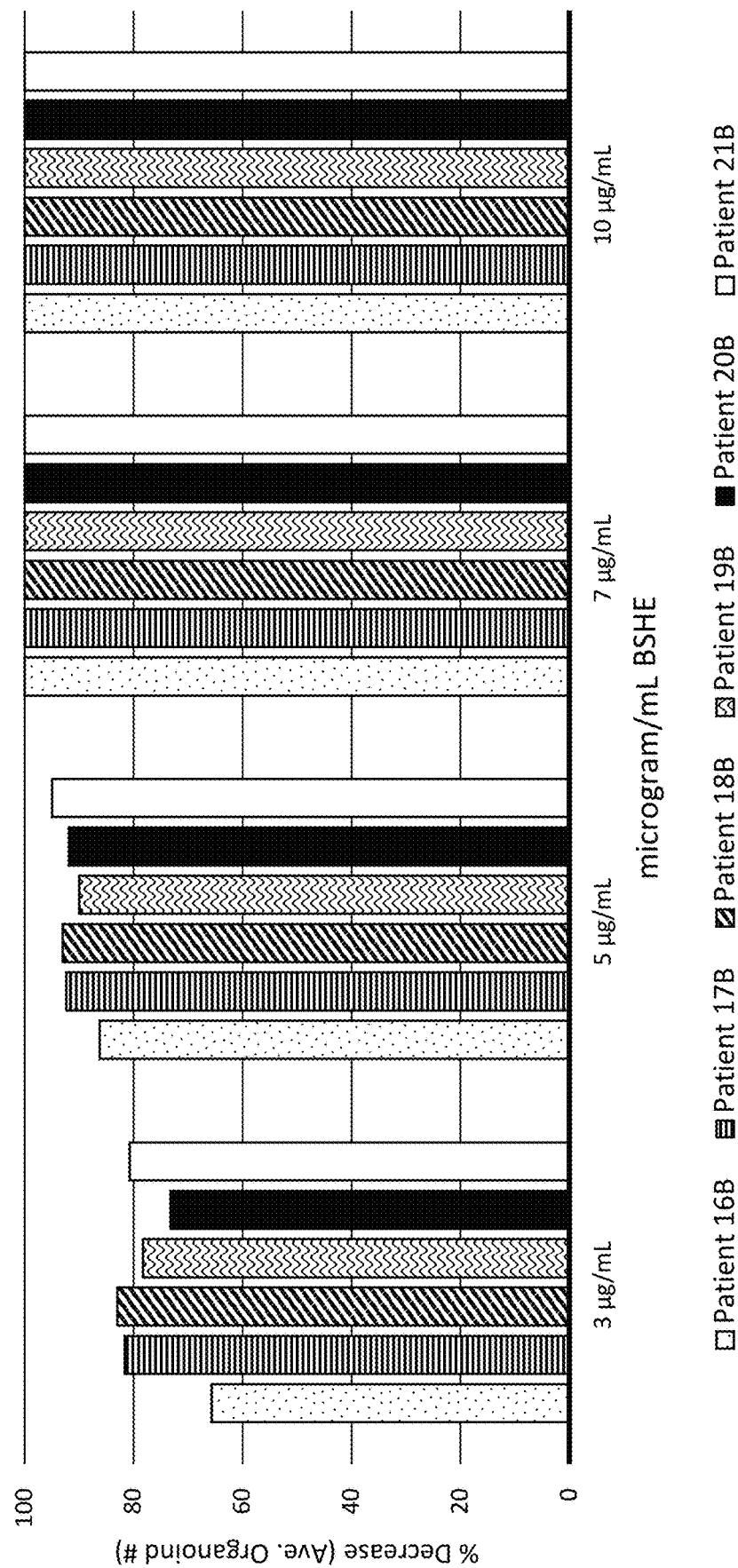

Six different grade 1 patient derived organoid samples were provided, and tested with 2, 3, 4, and 5 µg/mL of a *Cannabis* extract, BSHE. FIG. 2 depicts the results in a graphical form. This was performed for each of grade 1, grade 2 and grade 3 tumors. Grade 1 tumors exhibit<5% solid nonglandular, nonsquamos growth. Grade 2 EC tumors show between 6% and 50% of solid nonglandular, nonsquamous growth, while grade 3 tumors exhibit>50% of solid nonglandular, nonsquamous growth. The specific results in FIG. 3A and FIG. 3B depict the grade 3 EC tests over several different patients and concentrations. Each grade of cancer in the presence of CBD was effectively treated, to reduce or eliminate the cancerous tissues.

A further test was then provided, to test efficacy of variants of other plant derived *Cannabis* extracts, one being a broad spectrum hemp extract (BSHE), which was the basis for all prior studies, then a full spectrum hemp extract (FSHE), which contains trace amounts of THC, an isolated CBD, which is a naturally derived and isolated CBD, and finally an isolated CBDA provided as the acid form of CBD. Each of these were tested at 1, 2, 3, 4, 5, 7, and 10 µg/mL, with CBDA tested at 15, 20, 25, 35, and 50 µg/mL.

Figure 4A:
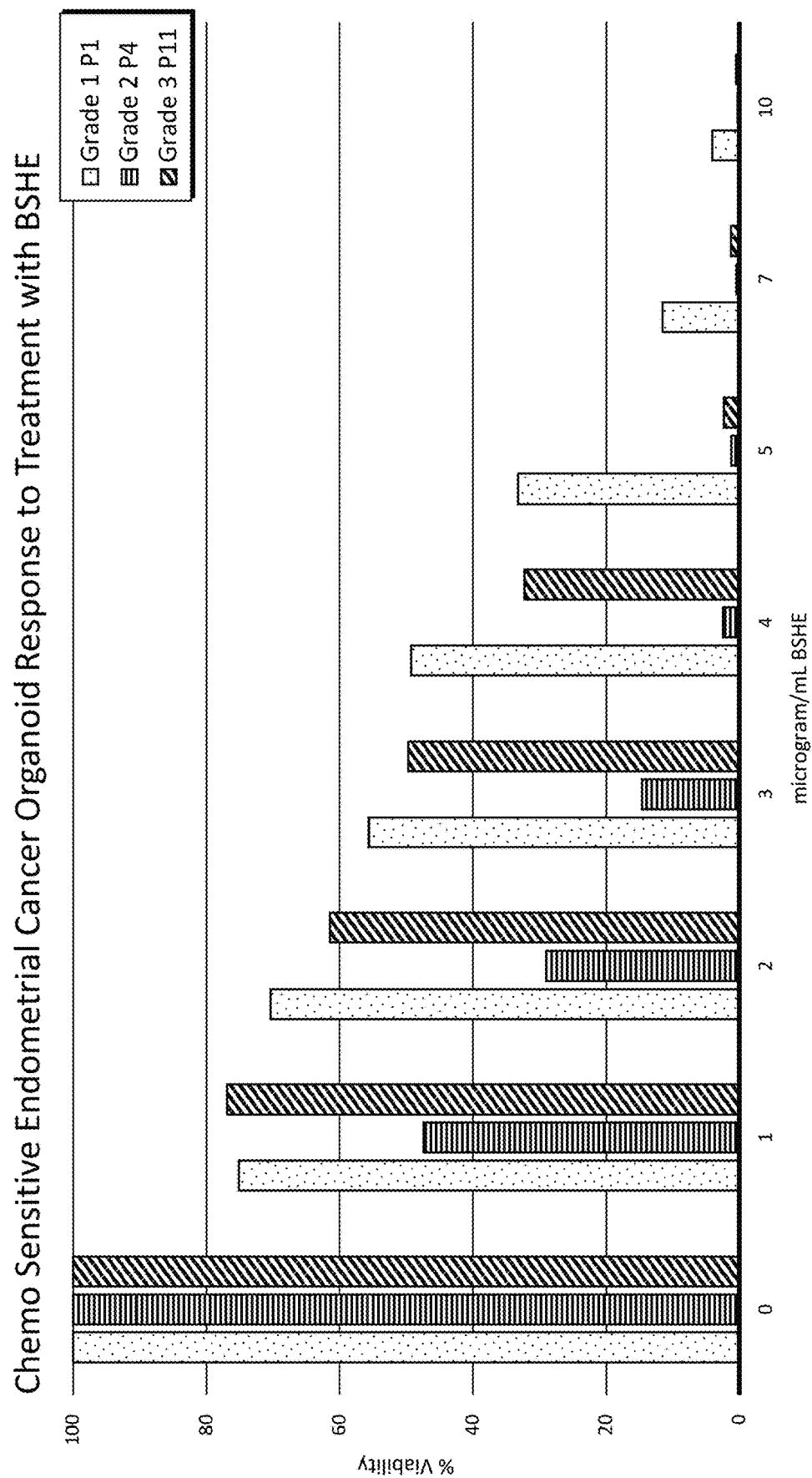
Figure 4B:
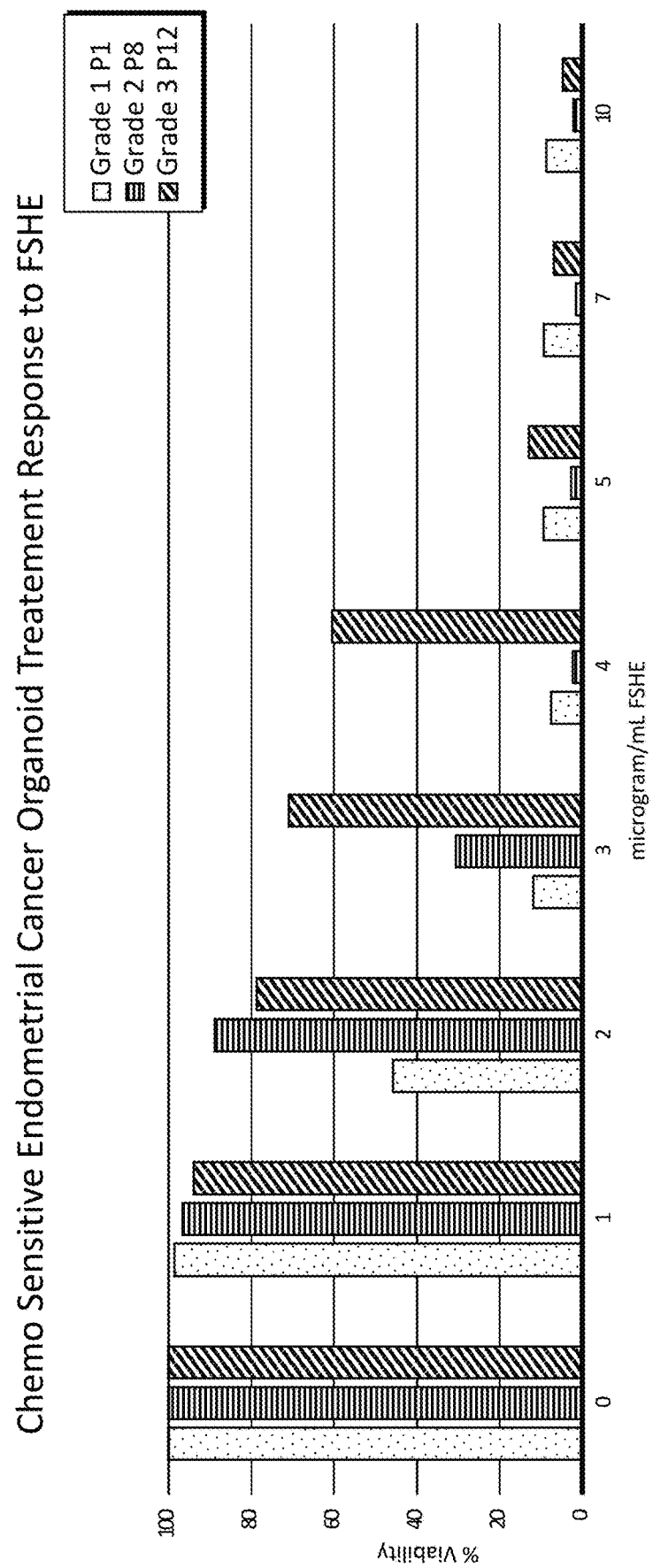
Figure 4C:
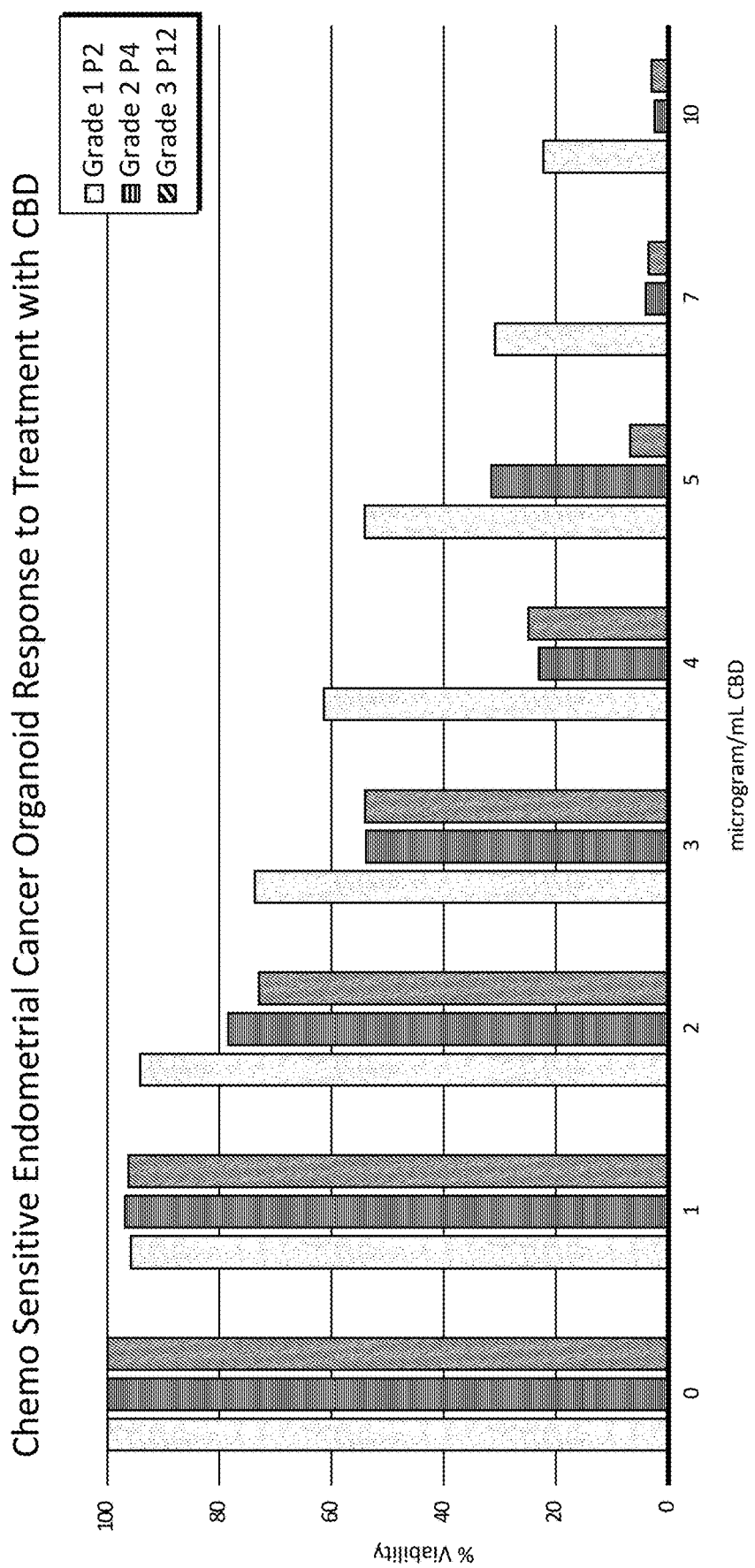

FIGS. 4A, 4B, 4C, and 4D depict graphical views of concentrations of each of the various different *Cannabis* extracts identified above, at the given concentrations, as tested on endometrial cancer organoids. Notably, a new set of patient derived organoids were obtained from additional patients and allowed a continued review of additional patients to confirm efficacy is maintained across larger patient populations. FIG. 4A particularly looks at the BSHE, which replicates prior studies. FIG. 4B uses FSHE as the treatment drug, FIG. 4C uses CBD isolate, and FIG. 4D uses CBDA as the treatment drug. then looked at whether different *Cannabis* extracts would maintain their efficacy on the EC patient derived organoids at concentrations between 1 µg/mL and 50 µg/mL. The data from FIG. 4A confirms all prior tests, and the data from FIGS. 4B and 4C shows that virtually all patients respond at 7 or 10 µg/mL, consistent with the results from FIG. 4A. Interestingly, one patient, who is later identified as a lower responder, does not show complete response at 10 µg/mL. However, organoids for this patient were then run and tested at 15 and 20 µg/mL, which showed a complete response, consistent with the other trials. Finally, with regard to the CBDA, CBDA showed an even stronger patient differentiation, wherein even at doses of 10 and 15 µg/mL, a strong response was not seen in all patient derived organoids. Accordingly, additional dosing up to 50 µg/mL was completed before all patients showed a nearly 100% reduction in organoid formation.

Accordingly, based upon the successful determination that *Cannabis* extracts comprising a therapeutic amount of CBD are effective in treating EC cancer cells, Applicant confirmed the results via mouse models, in patient derived xenograft studies. These xenograft studies confirm that the dosing is consistent between organoids and mouse models, as well as that systemic delivery is successful at treating the endometrial cancer.

FIG. 5 provides for the results of mouse models, which tested the ability of each of the BSHE, FSHE, CBD isolated, and CBDA to inhibit cancerous growth within the mice. The results speak for themselves. Notably, by day 14, and further at day 21, the tumor volumes for each of the mice have actually decreased. This is in stark contrast to both the prior art, which shows only a slowing or reduction in the growth rate of the cancer, and also to the control—which shows unregulated growth. Thus, the various CEs utilized on the mice were each effective at reducing tumor volume when used as a monotherapy, and induce apoptosis of the cancer cells in the mice models.

Despite the success of CBD as a monotherapy in the tests, in the context of cancer treatments, first line therapies for gynecological cancers, such as those of endometrial cancer and ovarian cancer utilize one of several chemotherapeutic agents. It is well known that chemotherapy agents are highly toxic and even under the best circumstances, it is difficult to say that they are well tolerated by patients. Chemotherapy is often given in progressive doses, meaning, it may take more of the chemotherapy drug to obtain the same response, as disease progresses. In many cases, patients progress wherein the endometrial cancer becomes chemoresistant. Applicant tested the combination of chemotherapy drugs with a *Cannabis* extract to determine if the combination could reduce the amount of chemotherapy required to obtain therapeutic responses, namely reducing the growth of endometrial cancer tumors and ultimately eradicating the tumors.

Several chemotherapeutic agents were tested for efficacy against both organoids and then on mice models. Chemotherapy agents and other current anti-cancer molecules have a typical negative profile, that is, they are highly toxic and kill not just cancer cells, but also healthy cells. Accordingly, a key metric and value is the ability to generate an equivalent clinical response to the chemotherapy, while using a lower total amount of the chemotherapeutic agent. A simplified example would be that if a normal dose of chemotherapy agent X was 200 mg, resulting in a reduction of tumor size by 90%, then the ability to use the same chemotherapy agent X at a dose of 100 mg and obtaining the same reduction of tumor size by 90% would provide significant benefits to the patient with regards to less secondary damage to healthy tissue, and other known impacts from the chemotherapeutic agent. Here, that result is not simply a 50% reduction in the amount of chemotherapy to yield an appropriate therapeutic response, but by using an amount six times less than the normal chemotherapy dose, combined with an IC50 dose of a *Cannabis* extract, yielded a therapeutic response that arrested tumor growth and reduced EC organoids, as well as reduced tumor volume in mice models.

Figure 6A:
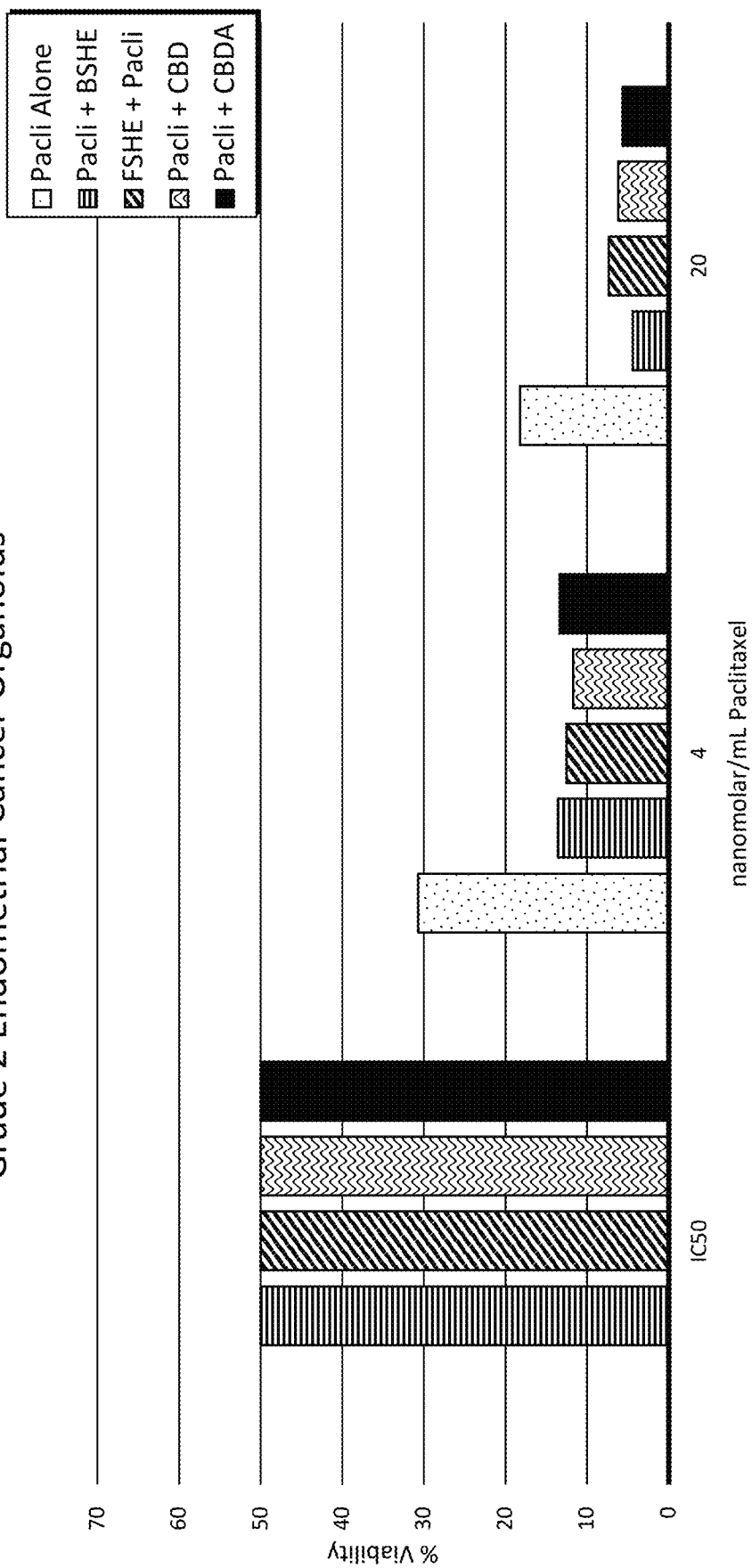
FIGS. 6A and 6B depict a combined therapy treatment tested on patient derived endometrial cancer organoids, wherein the chemotherapy agent is paclitaxel and is administered with a *Cannabis* extract.
Figure 6B:
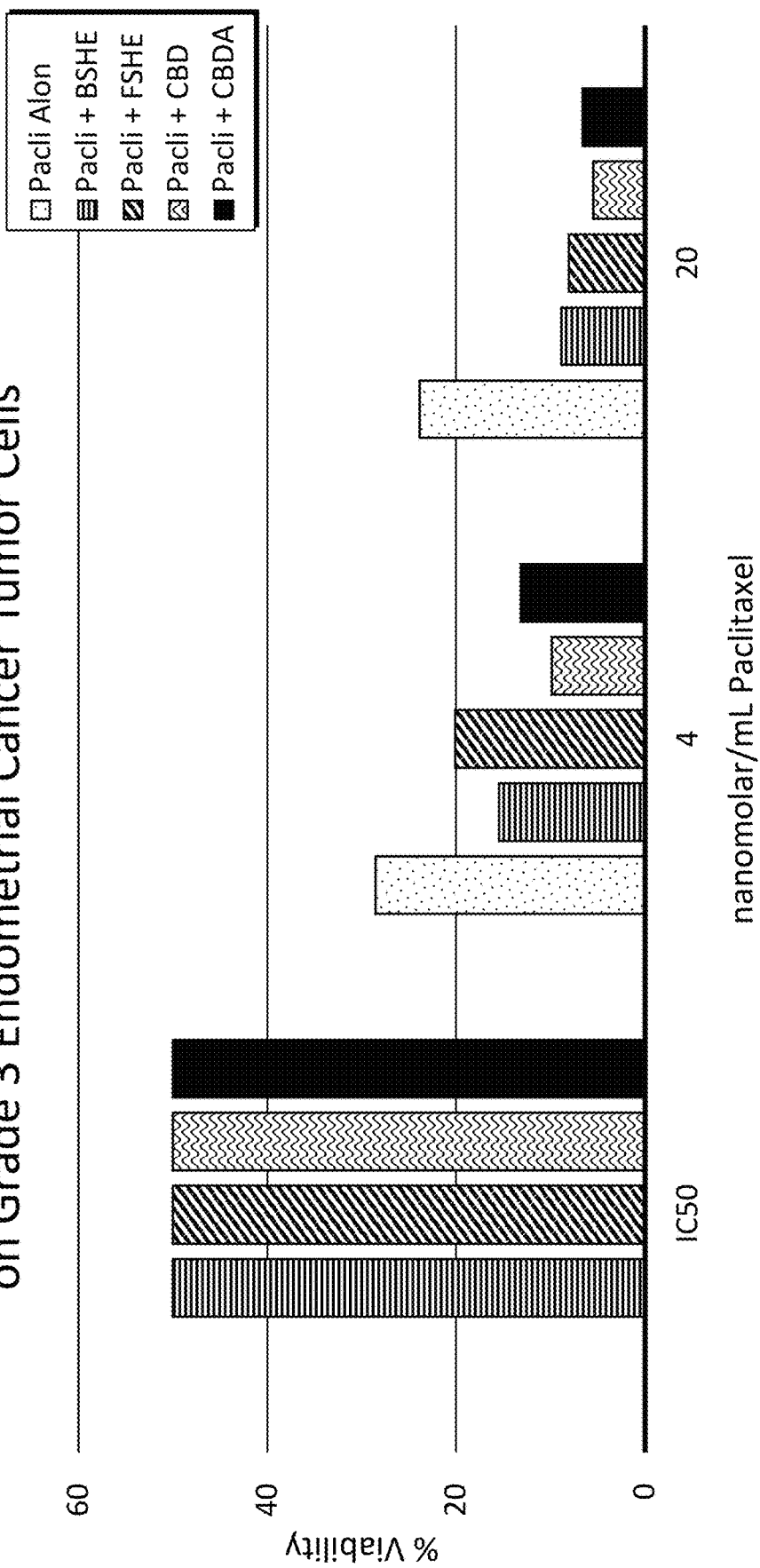

FIG. 6A details the use of paclitaxel in combination with CBD. FIG. 6A shows a 0 dose (control), meaning only the *Cannabis* extract products, given at an IC50 amount. The IC50 amounts are 3 µg/mL for the BSHE, 5 µg/mL for the FSHE and 15 µg/mL for the CBDA. The paclitaxel is administered at 4 nm/ml and also at 20 nm/ml in combination with the IC50 amount of *Cannabis* extracts. Notably, the paclitaxel was also tested at 8, 12, and 16 nm/ml, with only moderate changes in a linear fashion, and are thus not depicted in the drawing. In both FIG. 6A and FIG. 6B, the results for the two different grades of endometrial cancer are generally conserved. However, the grade 3 cancer, which is an ER(−) cancer, while the grade 2 is ER(+), show slight differences in efficacy.

What is striking about the results of FIG. 6, is that taking the first dose of paclitaxel and increasing that dose by 5×, results in a relative reduction in viability of about 12% for the organoids. However, in view of the significant toxicity, such minimal gains and a large multiplier of the dose, shows the weakness of the paclitaxel alone. The gains pale in comparison to what is evident from using the lowest dose of paclitaxel, with an IC50 dose of any of the *Cannabis* extracts, reducing the viability by nearly 20% across all tests. Thus, it would be more advantageous to administer the lowest dose of paclitaxel with a dose of *Cannabis* extract instead of increasing the dose of the paclitaxel. Accordingly, by taking an IC50 dose of any of the *Cannabis* extracts and administering it concurrently with the paclitaxel, a surprising synergy was identified, which could dramatically reduce the amount of paclitaxel needed to achieve low to no viability for the endometrial cancer organoids.

FIG. 7 repeats this test with a second chemotherapy drug, carboplatin. FIG. 7, like FIG. 6A and FIG. 6B before, shows IC50 data for four different *Cannabis* extracts. Here, the IC50 data was 5 μg/mL for the BSHE, 5 μg/mL for the FSHE, 3 μg/mL for the CBD, and 15 μg/mL for the CBDA. Again, each data set has its own IC50, based on how each patient derived organoid responds to a particular agent. However, the results are generally repeated from the paclitaxel data. Indeed, Carboplatin has a viability at 50 μg/mL of only about 50%, virtually equivalent to the IC50 date for all of the CBD. However, by combining the carboplatin with the *Cannabis* extracts, a synergistic effect is seen, where at any dose, the combined effects are superior to either alone. The results for FSHE are particularly noteworthy at the lowest dose, yet each of the BSHE, FSHE, and the CBD isolate show virtually 100% eradication with the higher doses of carboplatin. By comparison, the carboplatin alone diminishes from about 50% viability at the lowest dose to about 32% viability for the highest dose. Again, by increasing the chemotherapeutic drug by 5×, a relative improvement of only about 18% is found. However, by adding the lowest dose of carboplatin with an IC50 of CBD yields the same or better result. Thus, the combined therapeutic is surprisingly much more effective than either alone.

Thus, when looking at organoid examples, the addition of the *Cannabis* extract with a chemotherapy agent provides for a dramatic reduction in the number of organoids when combined with the paclitaxel or the carboplatin. Accordingly, based on this result, a patient could take a greatly reduced amount of either of the chemotherapy drugs, combined with an effective amount of the *Cannabis* extract comprising CBD to obtain a similar destruction of EC cells, and even shows a much greater impact and higher rate of kill than taking the chemotherapy agent alone, even at the highest effective doses. Furthermore, by testing the most common chemotherapy drugs utilized for EC, one being a plant-based alkaloid and the other a platinum-based, we know that the results are translatable across different chemotherapeutic agents that function in different ways from one another.

To confirm the efficacy of this combined therapy model, mice were then grown with EC tumor cells and given a control vehicle, a *Cannabis* extract alone, a chemotherapeutic agent alone, and then a combination of the chemotherapeutic drug (paclitaxel) and the *Cannabis* extract together. For the mice studies, the mice were given paclitaxel at 10 mg/kg body weight. This relates to a clinical dose of only 30 mg/m$^2$, which is dramatically lower than the 175 mg/m$^2$ that is given to human patients. Mice given any of the *Cannabis* extracts were administered as detailed above, with a dose of 30 mg/kg body weight.

Figure 8:
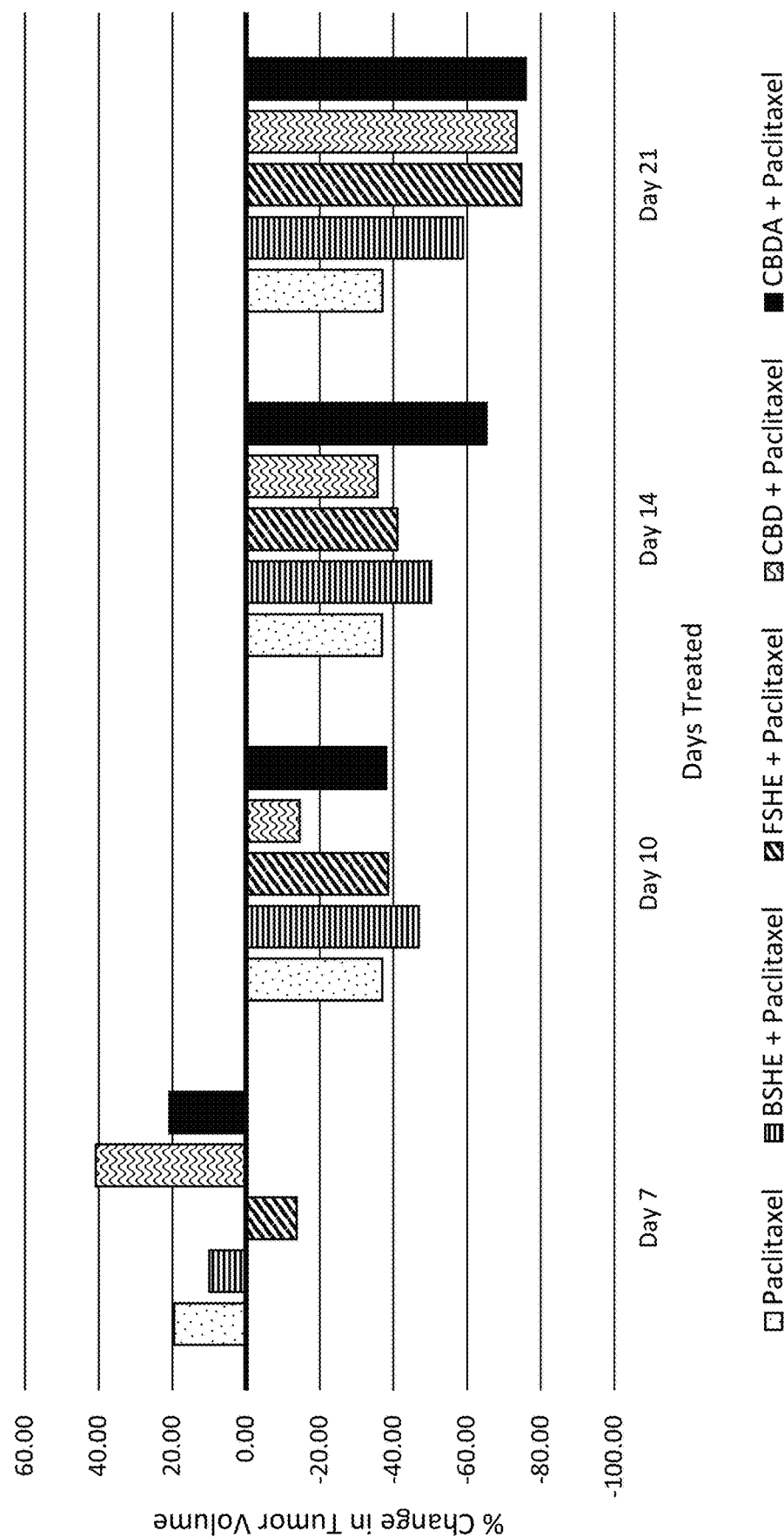
FIG. 8 depicts tumor volume data for mice administered paclitaxel and a *Cannabis* extract, which depicts the synergy related to the combined impact of chemotherapy being combined with the *Cannabis* extract.

FIG. 8 details the results of mice tumor volume comparing paclitaxel alone to those treated with a combined paclitaxel and a *Cannabis* extract. The control, or no treatment is not shown in FIG. 8, but results in more than 100% growth over the 21 days, as compared to the initial tumor volume. Combining a low dose of paclitaxel with an effective dose of any of the *Cannabis* extracts yields dramatically greater reduction in tumor volume as compared to the paclitaxel alone or even the *Cannabis* extracts alone at the given dose. Thus, co-administration of the *Cannabis* extract comprising a known amount of CBD with the carboplatin or with the paclitaxel was surprisingly more effective than their administration alone.

After the mice were treated, mice were sacrificed and histopathology taken to show that treating the mice with *Cannabis* extracts does not damage the cells of the ovary and fallopian tube, the uterus, vagina, or the liver. This is critically important, as treatment with high doses of chemotherapy are indiscriminate and damage these cells, when given over time. Thus, reduction in the quantity of chemotherapy drugs, whether at lower doses or none, in combination with the *Cannabis* extract can improve the outcome for patients by decreasing tumor volume at a greater rate, reducing the tumor volume to a greater total percentage than chemotherapy alone, and does not otherwise cause damage to the corresponding, healthy tissues of the reproductive tract and the liver as would occur from chemotherapy use.

A further interesting observation was determined by the impacts of pH on the efficacy of the *Cannabis* extract on organoid data. FIG. 9 shows that the native pH of the *Cannabis* extracts provided for an approximately 2 or 12% viability for the ovarian cancer derived organoids. However, increasing the pH led to substantial improvements in efficacy. However, pH of 12, and certainly of 14 are highly corrosive, alkaline concentrations and are not suitable for therapeutic use. Indeed, such a pH would not be isotonic, nor would it be appropriate for intravaginal application. The vagina has an acidic pH, which is necessary to maintain the balance of bacteria. However, strong modifications of the pH may lead to denaturing of the proteins or other problems. What was immediately evident is that the first attempts to buffer, even slightly, the pH to be more acidic, yielded worse results. Indeed, each of the two *Cannabis* extract materials had less efficacy by decreasing pH from 10.5 to pH of about 10. Furthermore, reducing the pH further to 8, again made the BSHE almost twice as weak at killing the organoids as the native pH, while the CBD isolate shows virtually no change. Even at pH of 7, a neutral pH, the changes are minimal at best.

In such a situation, decreasing the pH further would not likely lead to any further gains for therapeutic efficacy, as the changes were typically worse or virtually no change as compared to native pH. Instead, by further decreasing the pH to 4, a dramatic improvement in the % viability was seen for each of the BSHE and the CBD isolate, such that each were under a 1% viability, such result was unexpected based on the prior data trending towards a worse response or virtually unchanged response. Accordingly, when providing the *Cannabis* extract, especially where the *Cannabis* extract is provided orally, intravaingally or oral mucosally, to utilize a buffer to modify pH to between 2 and 6, yields a superior response, than giving the *Cannabis* extract at its native pH. Preferably, the *Cannabis* extract is provided in a carrier with a pH of between 3.5 and 5.5, and more preferably at between a pH of between 4 and 5.

Because of the unique property identified by the modification in pH, this was further tested against cells derived from head and neck cancer, deep endometriosis, as well as endometrial cancer. In each case, the unexpected improvement of reducing the pH was found, showing that the potential benefits of lowering the pH exist across treatment of all cell types.

Figure 10A:
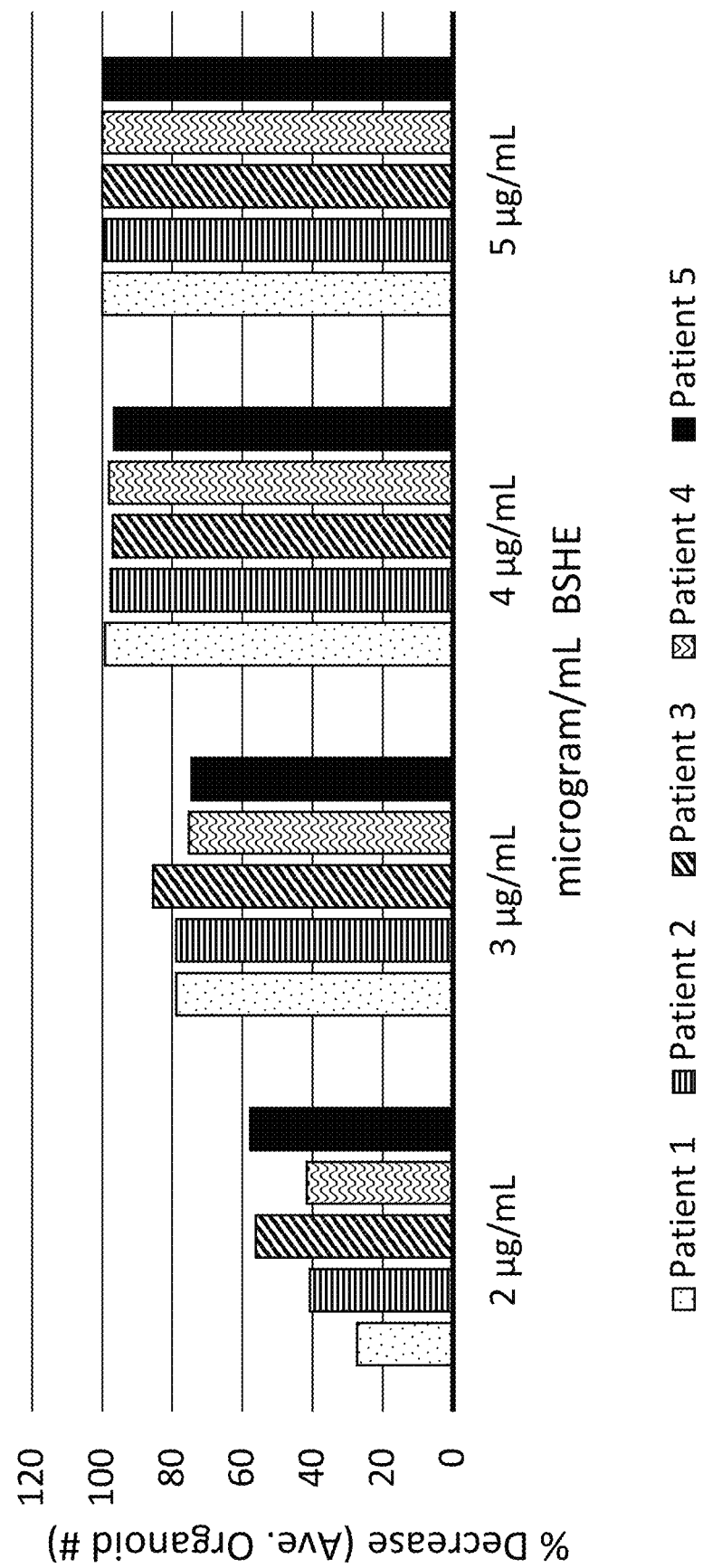
FIGS. 10A and 10B depict a graphical overview of the response of high grade ovarian cancer organoids to low doses (FIG. 10A) of 2, 3, 4, and 5 µg/mL of CBD, and FIG. 10B depicting higher doses at 3, 5, 7, and 10 µg/mL doses.
Figure 10B:
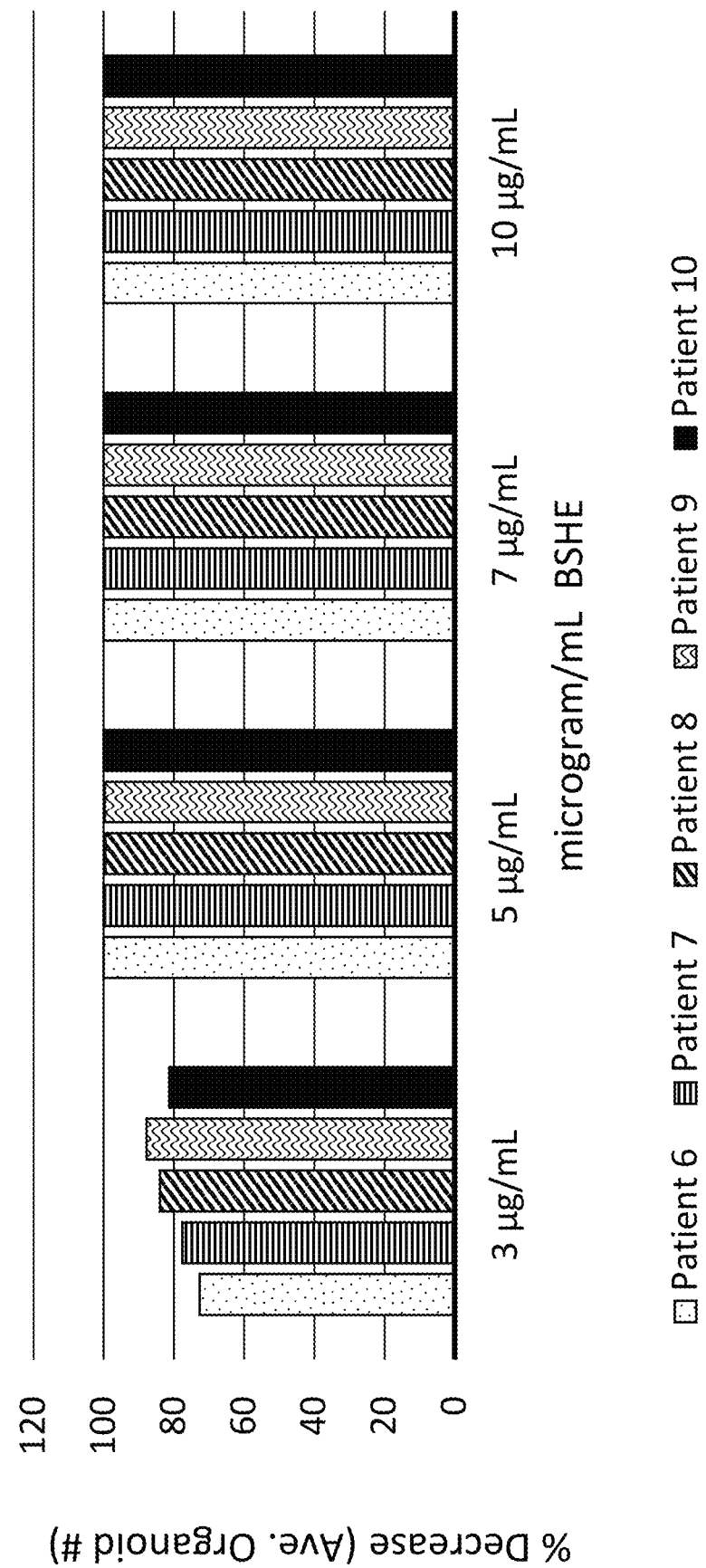
Figure 11A:
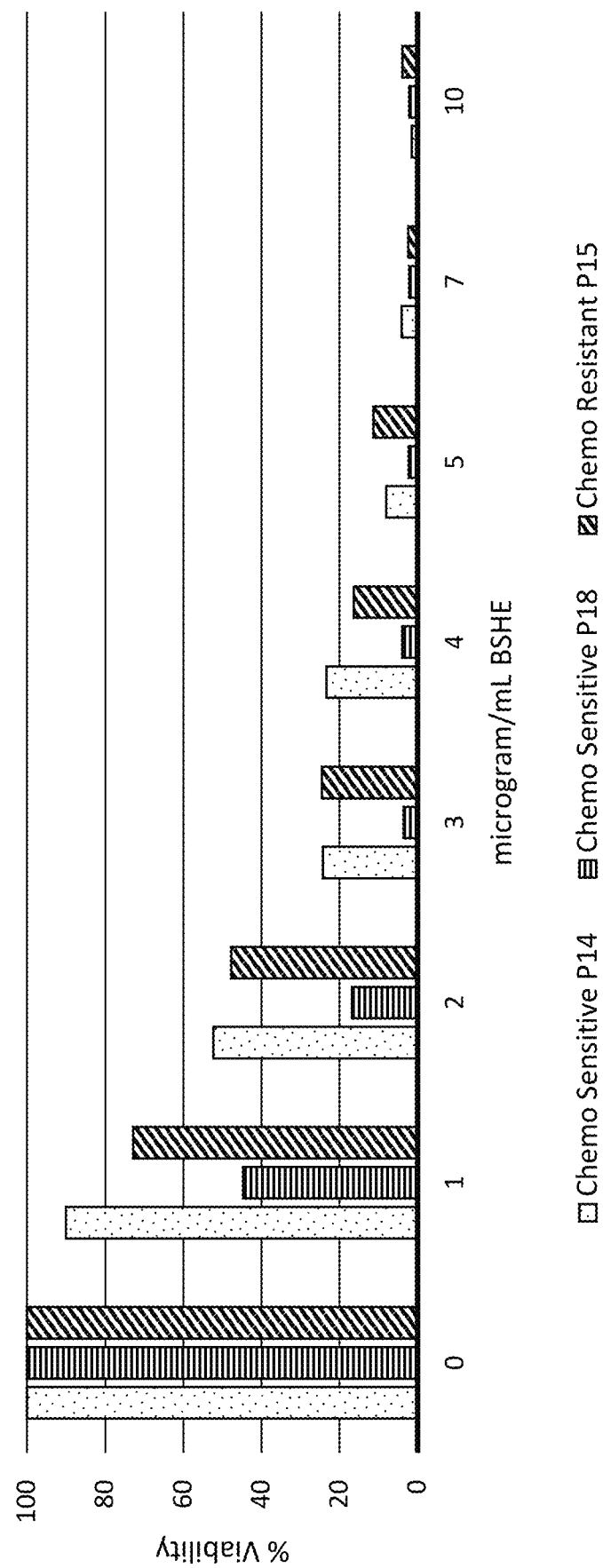

FIGS. 10A and 10B show that ovarian cancer, like endometrial cancer is treated effectively with doses of CE comprising CBD, wherein the CE is a BSHE.

FIGS. 11A, 11B, 11C, and 11D show individual patient data for BSHE, FSHE, CBD isolate, and CBDA isolate. Again, the results for ovarian cancer replicate the prior surprising finds for endometrial cancer. Here, with the ovarian cancer, both chemo sensitive cancer based cells and chemo resistant based organoids were tested. In each case, the results were analogous in that the different CEs were able to effectively treat these cancers and dramatically reduce cell viability in all cases. However, in some of the cases, higher doses were needed to achieve nearly total eradication.

Figure 12A:
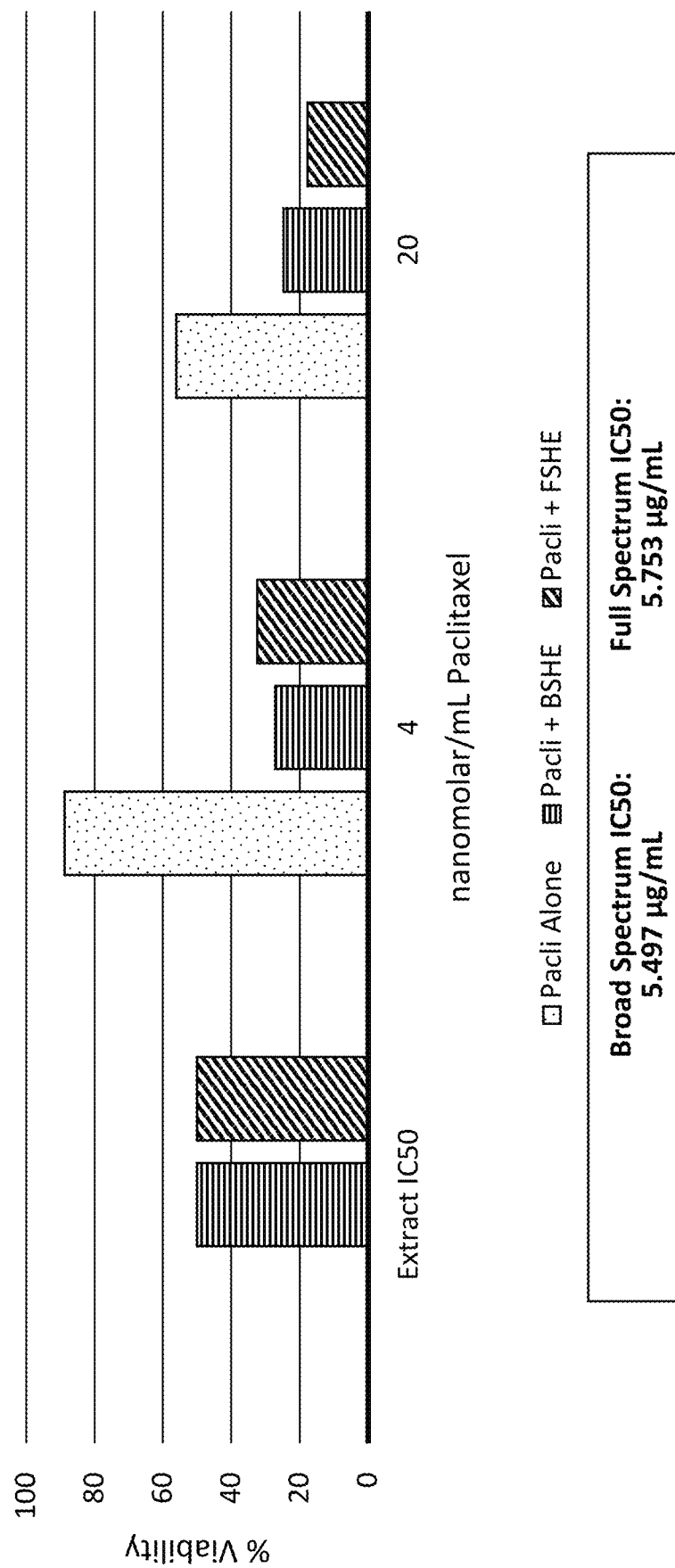
FIGS. 12A and 12B depict ovarian cancer organoid cells and their response to paclitaxel and a combined treatment of paclitaxel and *Cannabis* extract.
Figure 12B:
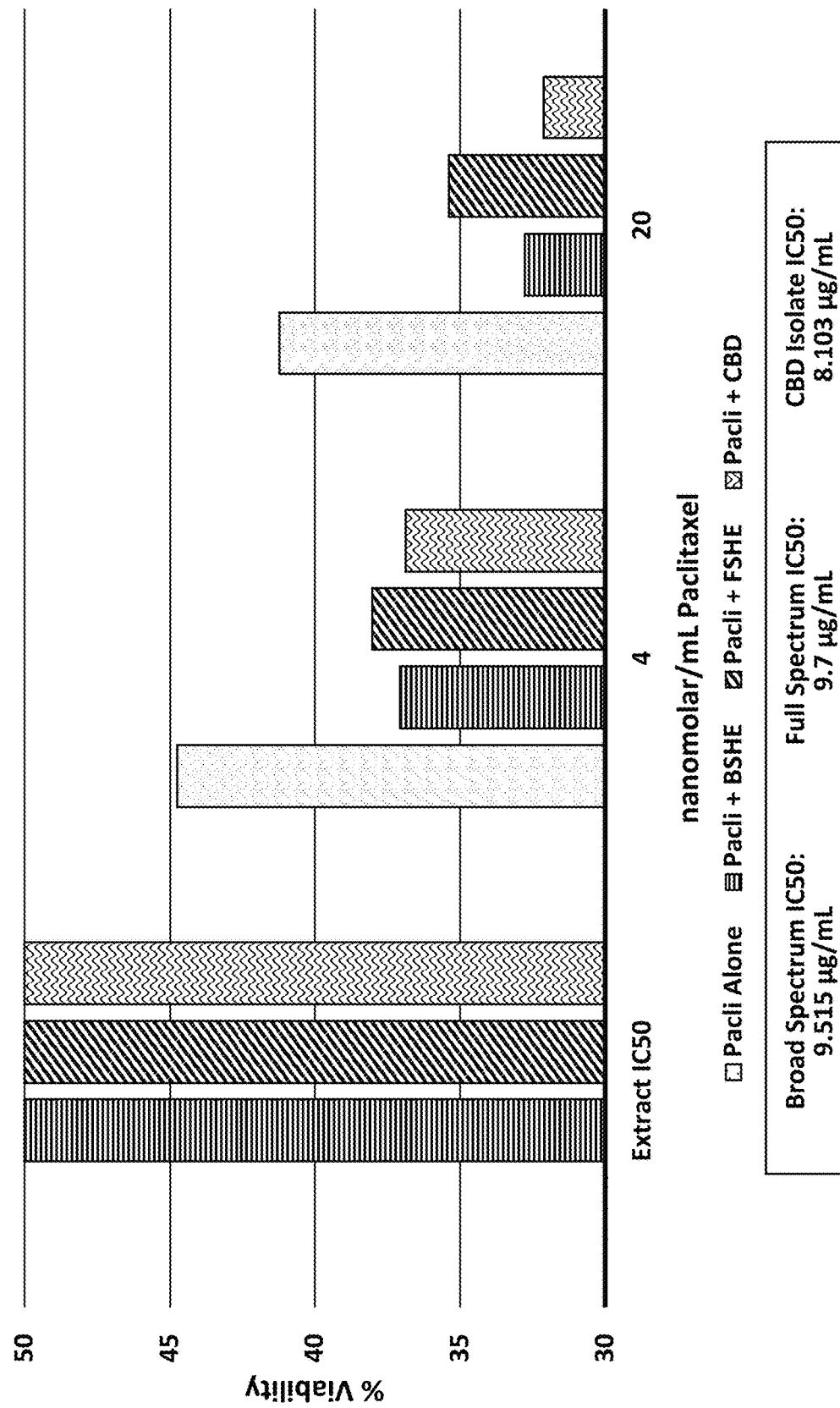

FIGS. 12A and 12B depict combination of paclitaxel and CE on ovarian cancer organoids. The results replicate the findings for endometrial cancer. Here, both the chemo resistant and the chemo sensitive cancer derived organoids were more effectively treated with the combination therapy of the paclitaxel and the CE, than either alone.

Figure 13A:
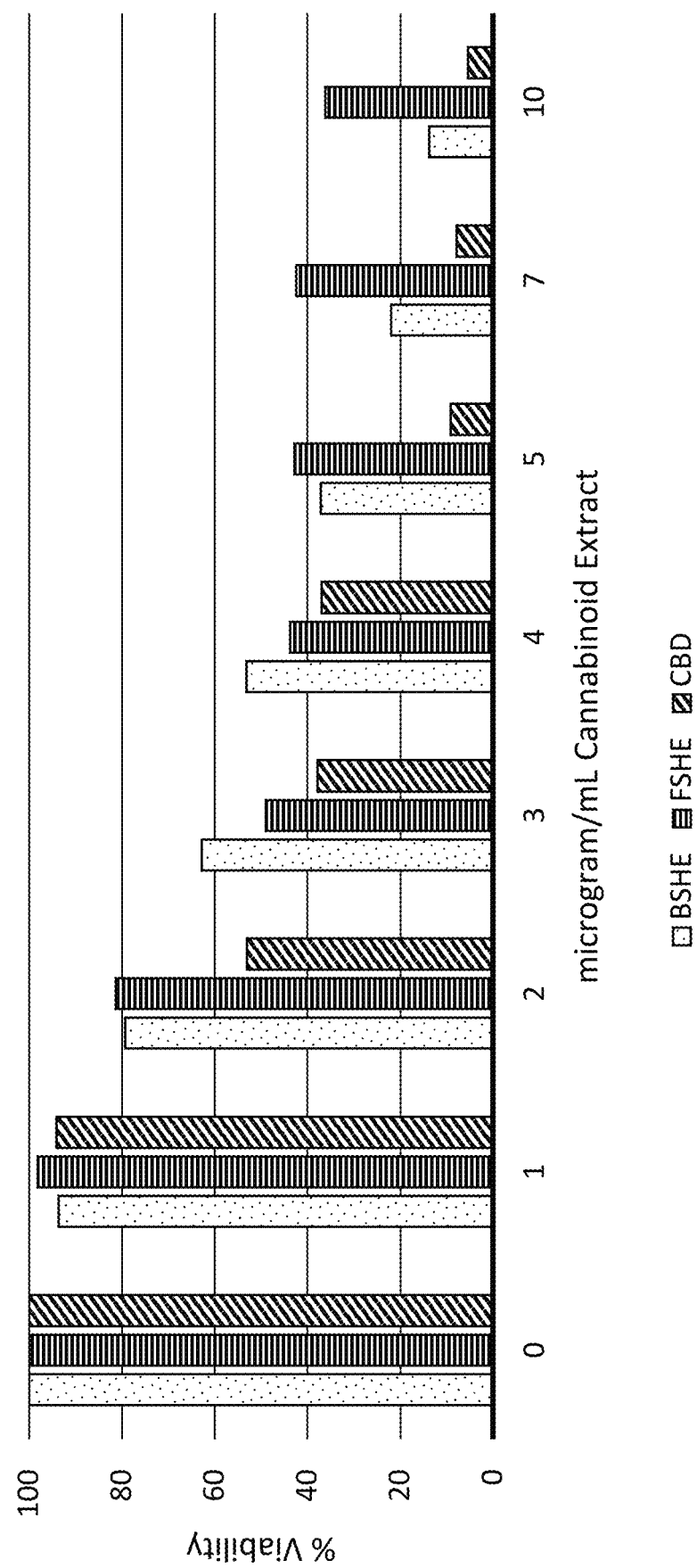
FIGS. 13A and 13B depict human head and neck cancer organoids being treated with three different *Cannabis* extracts, namely, broad spectrum hemp extract (BSHE), full spectrum hemp extract (FSHE), and CBD isolate.
Figure 13B:
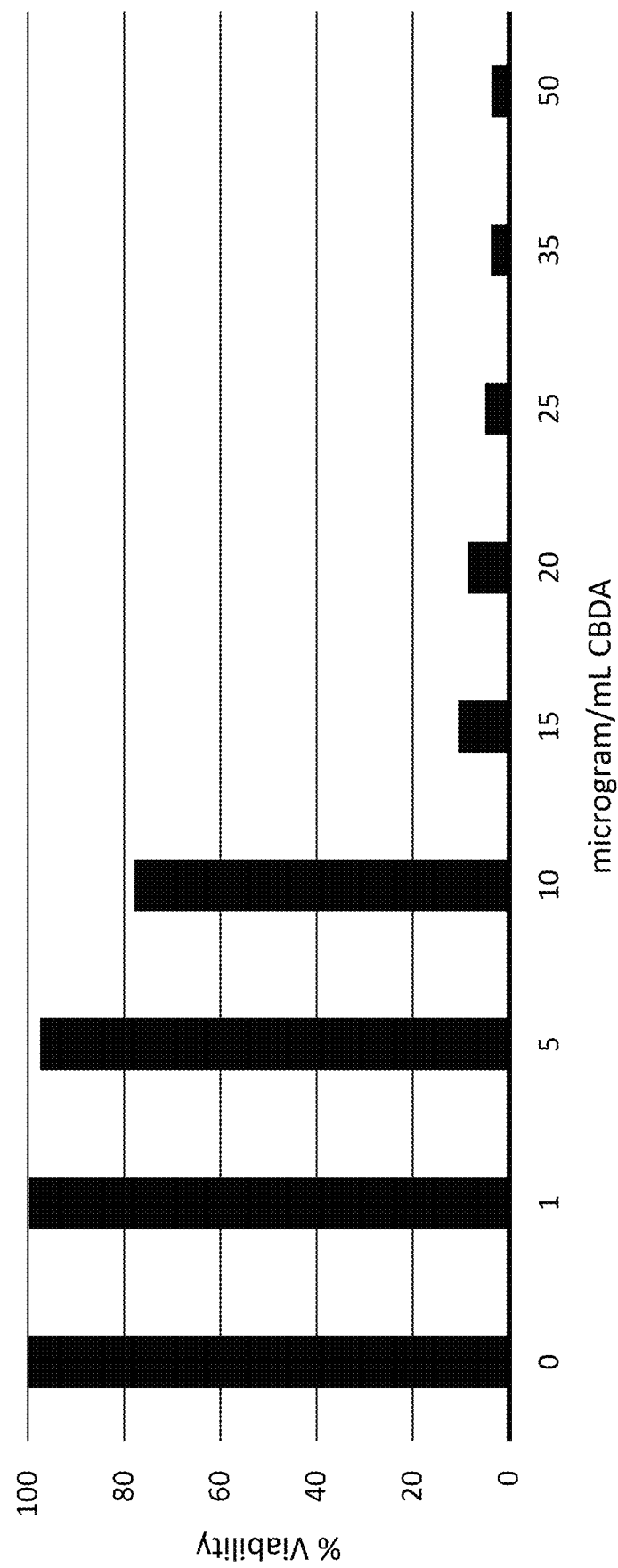

FIGS. 13A and 13B depict head and neck cancer organoids response to CE. The findings replicate the prior endometrial and ovarian cancer results across each of BSHE, FSHE, CBD isolate, and CBDA.

FIG. 14 depicts head and neck cancer organoids response to a combination of paclitaxel and CE. The results confirm the prior results with endometrial cancer and ovarian cancer.

Figure 15A:
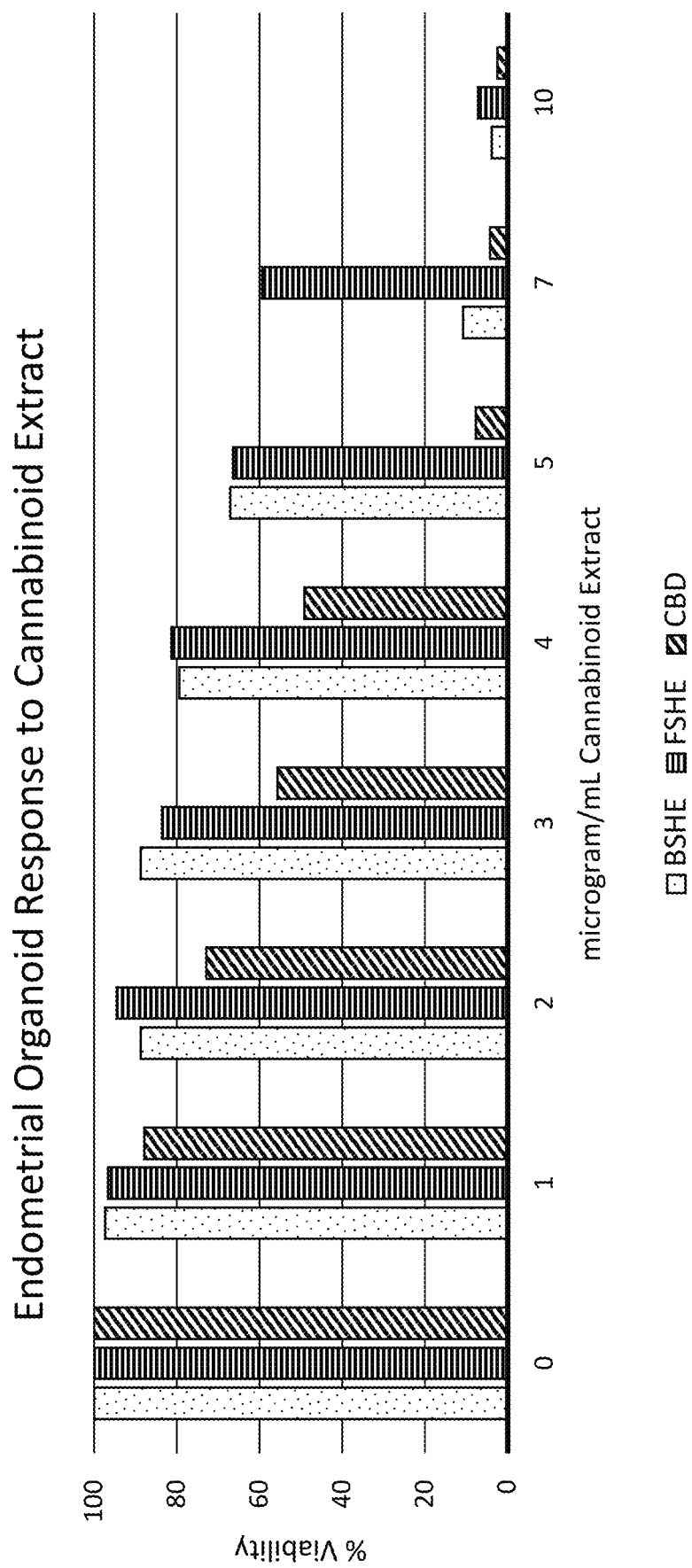
FIGS. 15A and 15B depict further graphs of BSHE, FSHE, and CBD isolate for 1, 2, 3, 4, 5, 7, and 10 µg/mL concentration on endometrial organoids.
Figure 15B:
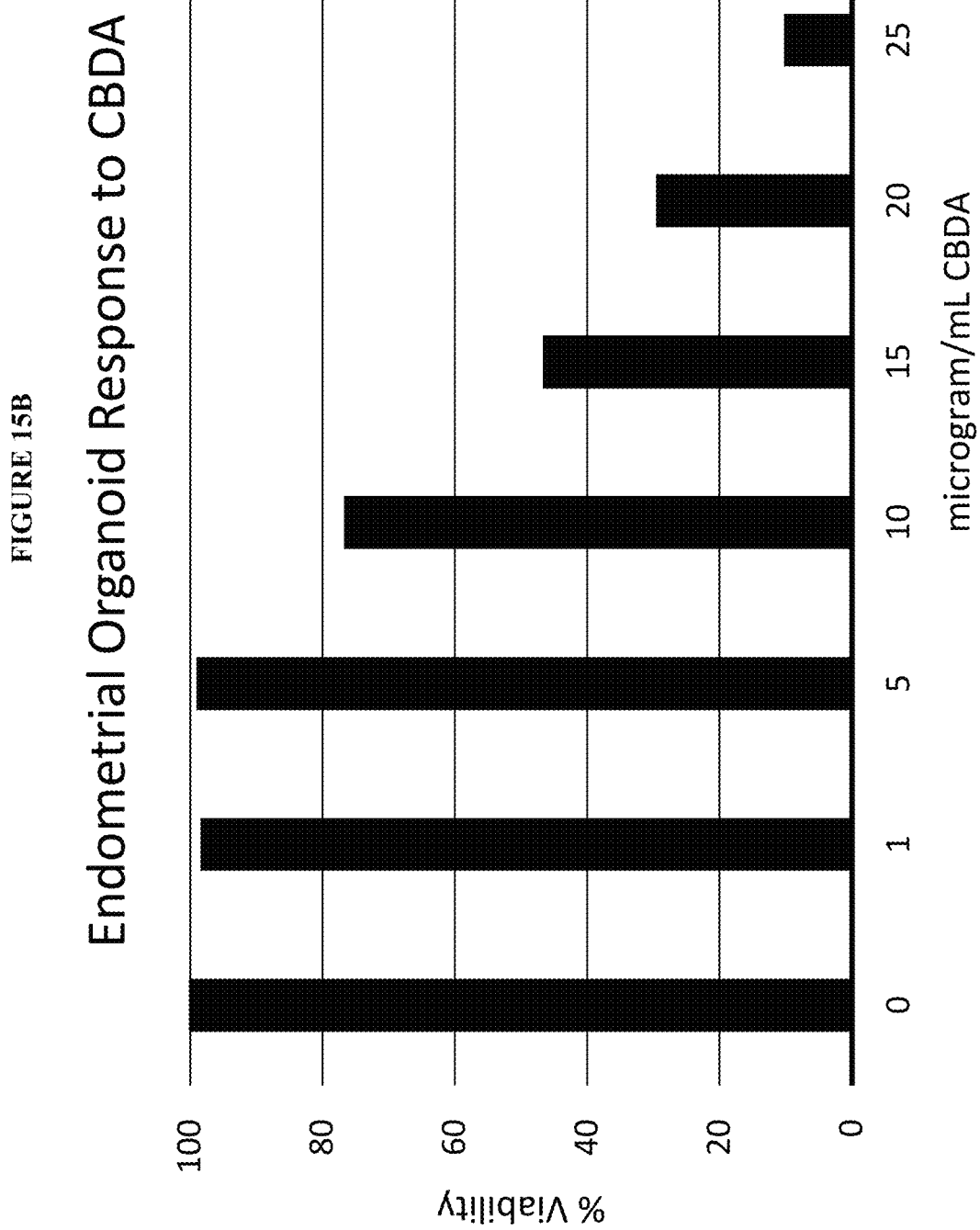

FIGS. 15A and 15B depict the response of BSHE, FSHE, CBD isolate, and CBDA on endometrial organoids. The results confirm the prior results for other cases for endometrial cancer, ovarian cancer and head and neck cancer. Because of the common origin of endometrial tissue for endometriosis and endometrial cancer, Applicant has noted that response to the carious CEs among the various studies, shows that these tissues, though being different disease states, react in an analogous manner. Therefore, as detailed herein, the compositions comprising the CE and a flavonoid have therapeutic overlap with those with endometrial cancer.

In each of the above test cases, while CBD was effective, and surprisingly more effective in combination with a chemotherapeutic agent, or by adjusting pH of the CE to be acidic, variations in treatment were evident in nearly each group of patients. While some variation is expected, Applicant wanted to improve efficacy, so as to further improve the monotherapy with CBD, or in combination with any of the chemotherapeutic drugs.

As CBD is relatively insoluble in water, it is most frequently provided in an oil, such as an edible vegetable oil. One of the most common of these is olive oil. Olive oil is rich in tocopherol, a known antioxidant. Applicant therefore wanted to test whether dissolving the CE into an oil carrier would support the increased efficacy as described in the prior art. As an initial test, the primary antioxidant, tocopherol, was tested for its efficacy on endometrial cancer organoids.

At the outset, the tocopherol was administered in DMSO as the carrier to the endometrial cancer cells. Despite its widespread use in the prior art, the tocopherol had virtually no impact on cell viability when used alone in the carrier. Indeed, if anything, it was responsible for cell proliferation, as depicted in FIG. 16, as compared to the carrier alone.

In view of the result, Applicant wanted to see if this was conserved among other antioxidants. Applicant obtained beta-caryophyllene, another potent antioxidant with a significantly different structure than the tocopherol, as well as three other molecules, each of which are closely related flavonoids, these being myricetin, taxifolin, and chrysin. Flavonols are a class of compounds having a 3-hydroxyflavone backbone, and which additional members of the genus differ based upon the different positions of the phenolic hydroxyl groups. Each were tested at concentrations equivalent to those tested above for tocopherol. The flavonol class of compounds are inhibitors of CYP2C9 and CYP3A4, which are known to metabolize drugs in the body, including cannabidiol. Thus, Applicant wanted to see if their impact, both as an antioxidant and towards inhibition of certain pathways would modify the efficacy of the combination composition.

Figure 16:
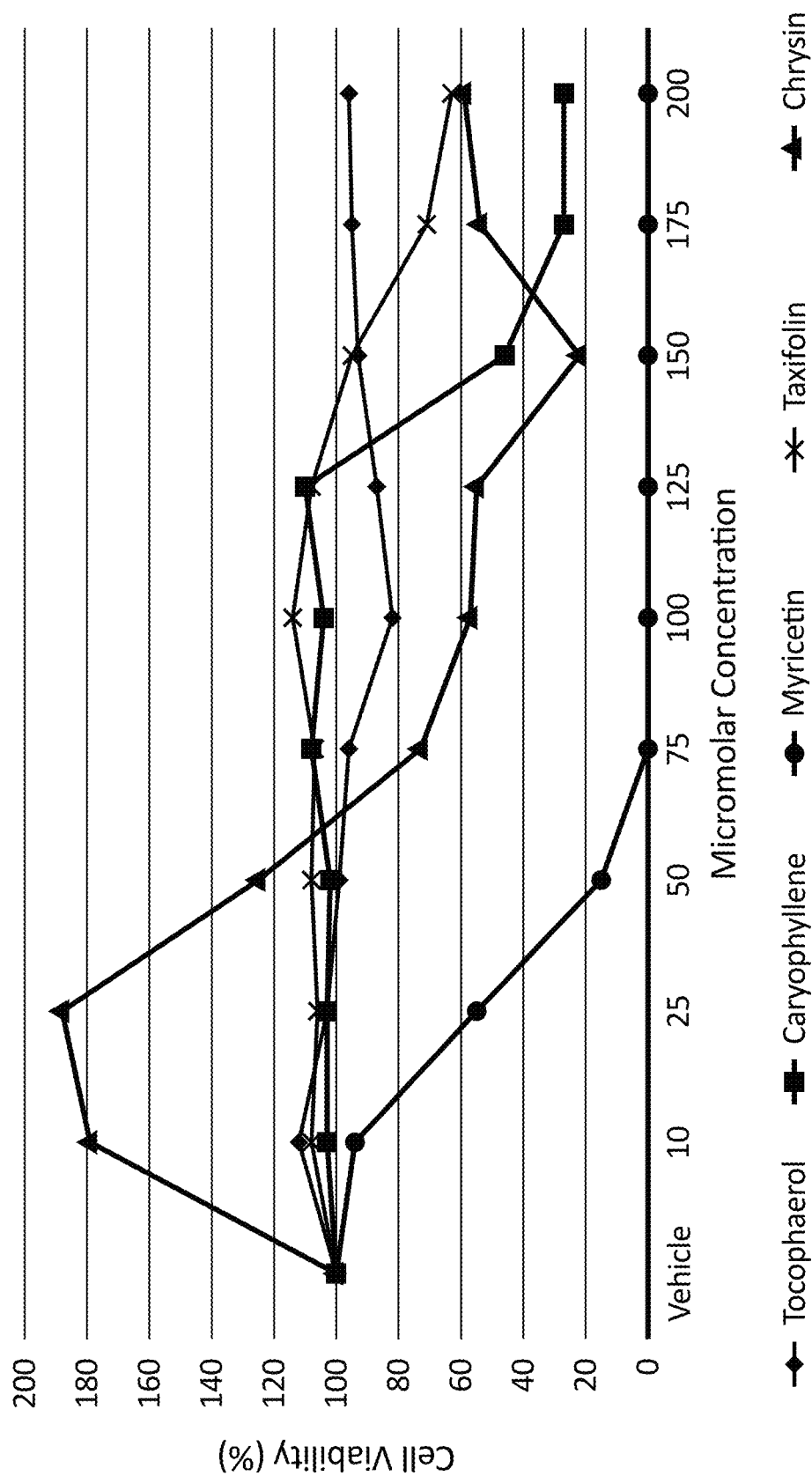
FIG. 16 depicts a graphical representation of the kill rate of flavonoids tested on endometrial cancer derived organoids, as compared to a control.

As FIG. 16 depicts, the results were varied, with some of the molecules clearly increasing the growth of the cancer cells, even a concentrations as high as 125 µM. Meaning, that in some concentrations, growth occurred, while in other's some anti-cancer effects were seen. However, one of the drugs, myricetin, was strongly anti-cancer, and significantly reduced cell viability as a monotherapy. The purpose of these tests was to provide a baseline and evaluation of how such molecules might work on their own. It shows that in many cases, having quantities of certain molecules actually increased the growth rate of endometrial cancer cells as compared to the vehicle alone control.

While chrysin, myricetin, and taxifolin share a similar structure, their structure is significantly different from Tocopherol or Beta-Caryophyllene. However, these three molecules all possessed different profiles towards cell proliferation or cell death when used as a monotherapy. Thus, their use alone would likely be seen as generally ineffective, except for myricetin.

A further set of flavonols and one additional flavone were also studied to see if these results were conserved across these class of compounds, their responses are detailed in Table 2 below.

TABLE 2

FLAVONOIDS SCREENING ON ENDOMETRIAL CANCER CELL ORGANOIDS

| Concentration (µM) | Quercetin Average | Luteolin Average | 3-hydroxyflavone Average | Galangin Average |
|---|---|---|---|---|
| 0 (Vehicle) | 100.00 | 100.00 | 100.00 | 100.00 |
| 10 | 95.16 | 90.54 | 61.62 | 98.74 |
| 20 | 89.43 | 56.75 | 48.26 | 98.58 |
| 30 | 85.33 | 33.96 | 51.28 | 96.96 |
| 40 | 58.16 | 1.39 | 41.00 | 69.20 |
| 50 | 34.67 | 0.00 | 37.88 | 49.62 |
| 60 | 25.59 | 0.00 | 35.89 | 33.55 |
| 80 | 7.88 | 0.00 | 34.31 | 25.66 |
| 100 | 0.00 | 0.00 | 34.65 | 29.73 |

Of these four additional compounds, luteolin had the highest response rate, but all of them yielded therapeutic responses, which is consistent with the prior compounds tested. Notably, the luteolin and the chrysin are flavones, which do not have the hydroxyl group adjacent to the carbonyl, as compared to the class of flavonols. This can be seen in the structure below at the R3 carbon, which is a hydrogen in the flavone compounds instead of a hydroxyl group for the flavonols.

Figure 17A:
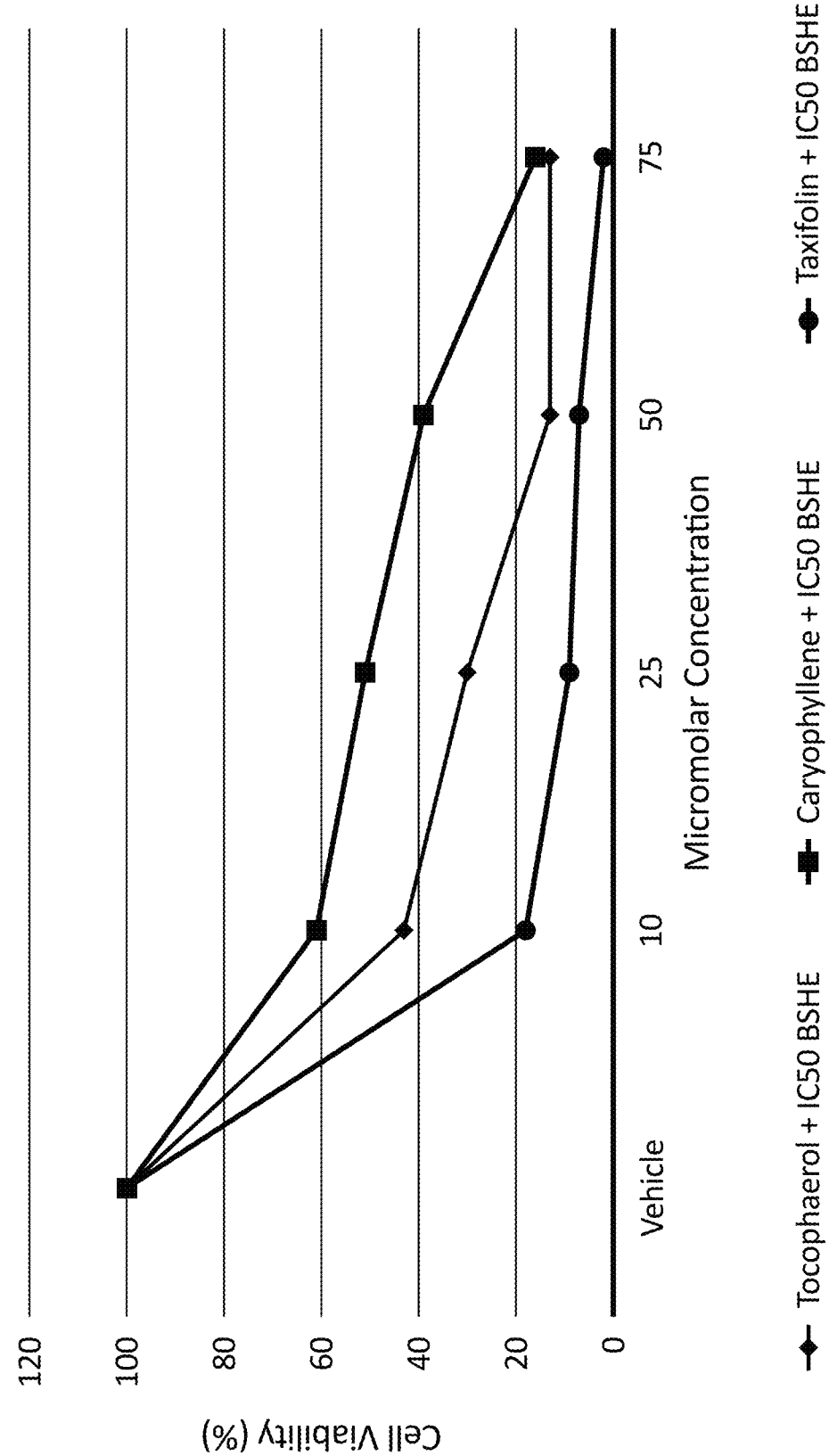
FIGS. 17A and 17B depict a graphical representation of the kill rate of certain flavonoids being combined with BSHE.
Figure 17B:
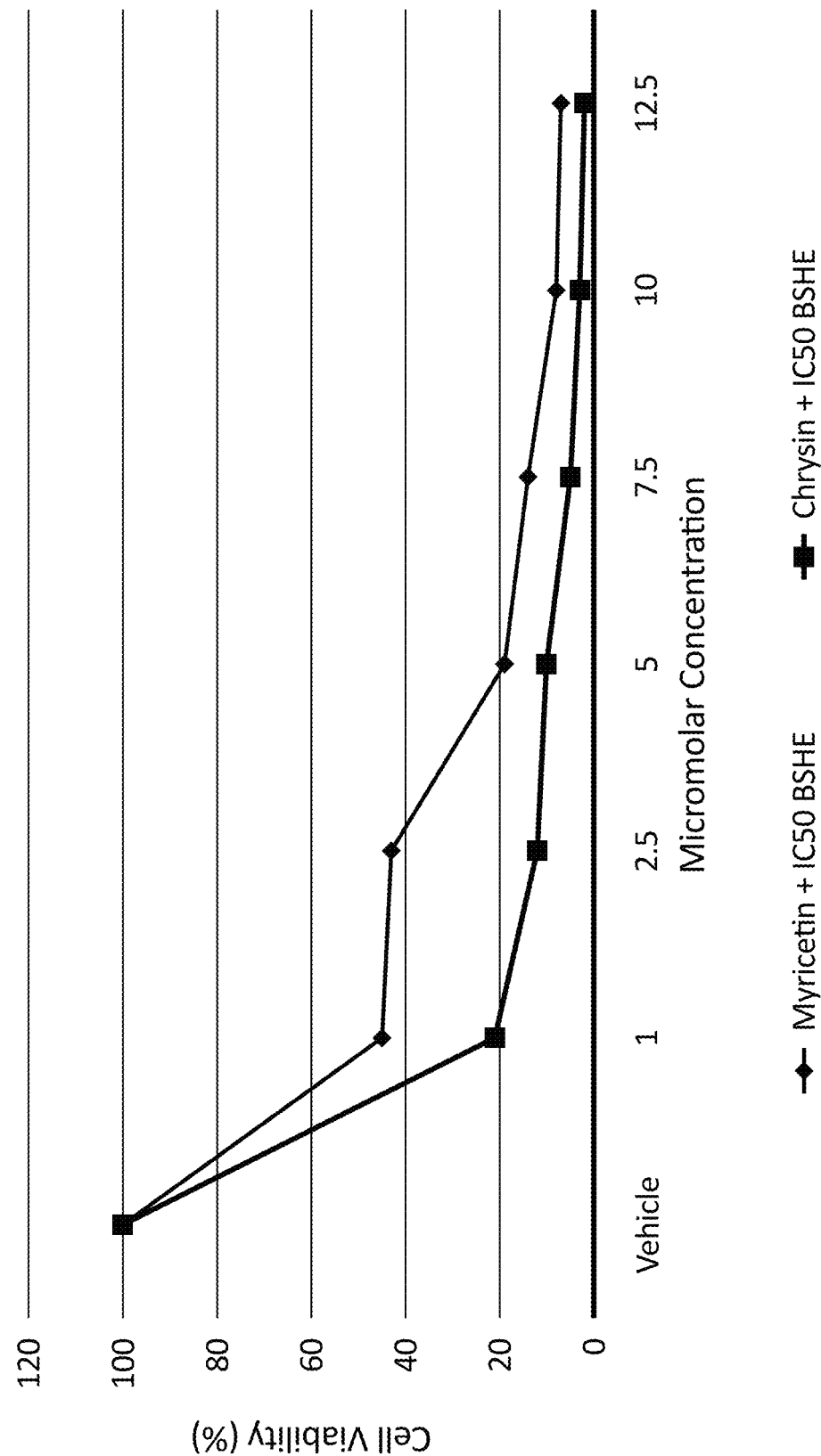

A representative sample of these compounds was then tested in combination with CEs to determine how they would react as a synergistic composition. Combining these molecules with a CE, either a FSHE or a BSHE, yielded further interesting results. FIGS. 17A and 17B compare several of the selected antioxidants in combination with BSHE. FIG. 17A first compares tocopherol, beta-caryophyllene, and taxifolin in combination with BSHE at an IC50. Notably, in direct contrast to the monotherapy, the combination with a BSHE showed some promise for each of these molecules, however, their concentrations typically requiring at least a 25 micromolar or higher concentration, when combined with the IC50 of the BSHE to show significant variance from the IC50 value. However, by at least a concentration of 75 µM, each of the materials showed an unexpected potential for its combined efficacy with the BSHE. As referring back to FIG. 16, each of those three materials, at a concentration of 50 µM. and virtually at 75 µM were inducing cell proliferation. Thus, there would be no expected synergy with the CBD and it would be expected that the combination would still yield cell proliferation, or at most, a modest reduction in cell viability. Yet, at a concentration of 75 µM, in combination with BSHE, a synergistic response was found and yielded a significant reduction cell viability as compared to the IC50 value. Of these three, taxifolin created the greatest reduction in viability, which was especially surprising based on its cell proliferation as a monotherapy.

FIG. 17B depicts the response of myrecetin and chrysin, when combined with the IC50 of the BSHE, each of which are most similar in structure to taxifolin. Note that at a concentration as low as 12.5 µM, each of the materials showed nearly 0% cell viability. While myricetin showed the greatest response as a monotherapy, chrysin was a weak performer, and actually inducing cell growth at lower concentrations, and only showing any sign of efficacy at above about 75 µM in concentration. In FIG. 16 chrysin was most effective at a range of between about 75 and 150 µM, and actually performed worse at a concentration above 150 µM, and showing at 10 µM a growth of 178.99, at 25 µM a growth of 188.45, and at 50 µM a growth of 125.21%. At 100 M, however, it had reduced viability to 56.74, about at in IC50 amount. However, in combination, as detailed in FIG. 17B, at 10 µM it has only a 3.04% cell viability—showing about a 175% change in viability. Myricetin, already being superior as a monotherapy, was even more effective in combination with an IC50, and showing at 10 µM a viability of only 8.55, a nearly 86% reduction from its monotherapy. When combined with the CE, these two molecules essentially reduced the cell viability to nearly zero at low concentrations. In sum, the three molecules that were flavonols or a flavone, (myricetin, taxifolin, and chrysin) and each showed dramatic and unexpected synergy when combined with a BSHE in inducing cell apoptosis. No other molecule tested was able to generate a virtually complete response with an IC50 amount of CBD, as compared to this class of molecules.

Figure 18:
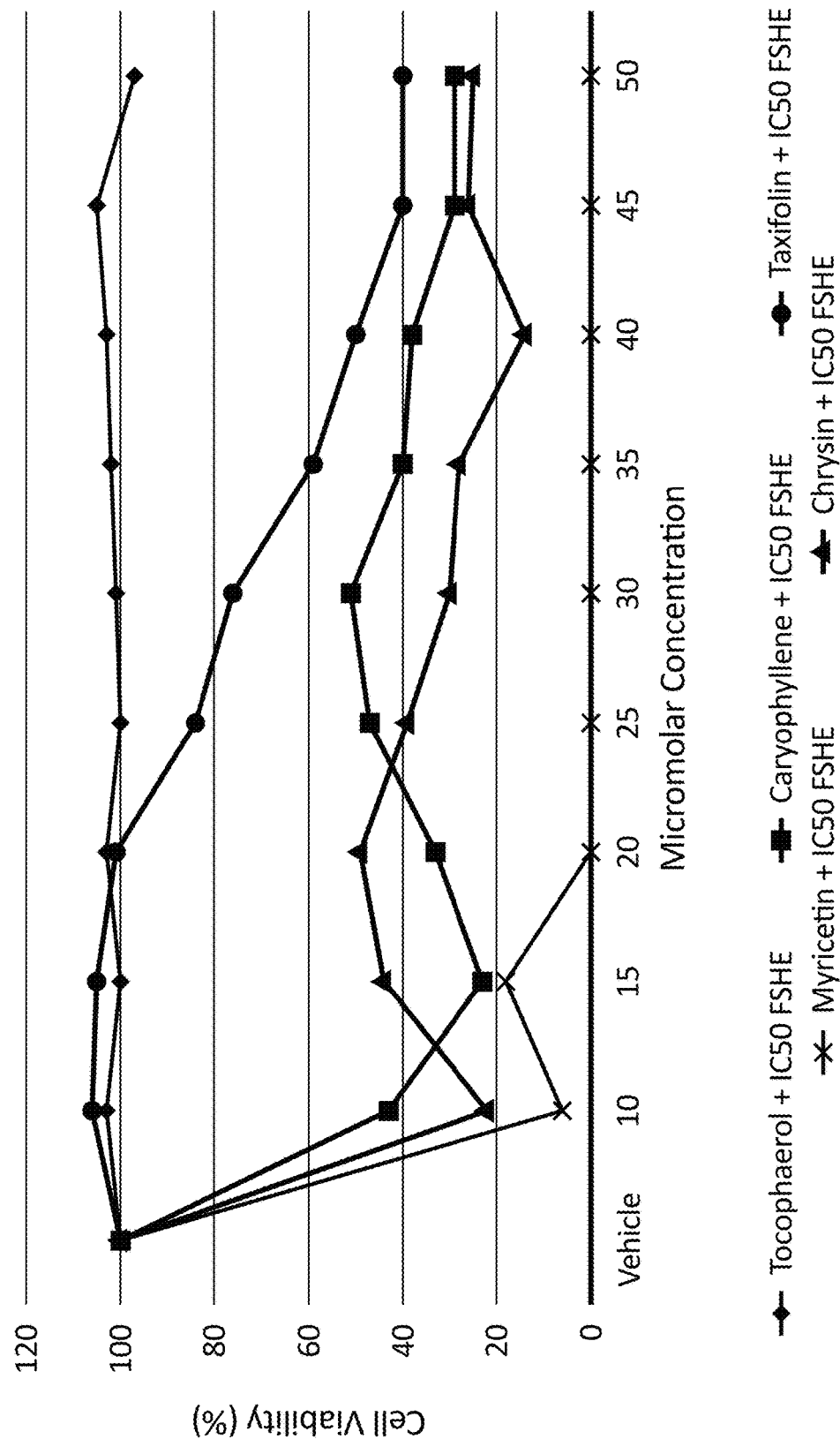
FIG. 18 depicts a graphical representation of the kill rate of certain flavonoids being combined with FSHE.
Figure 19A:
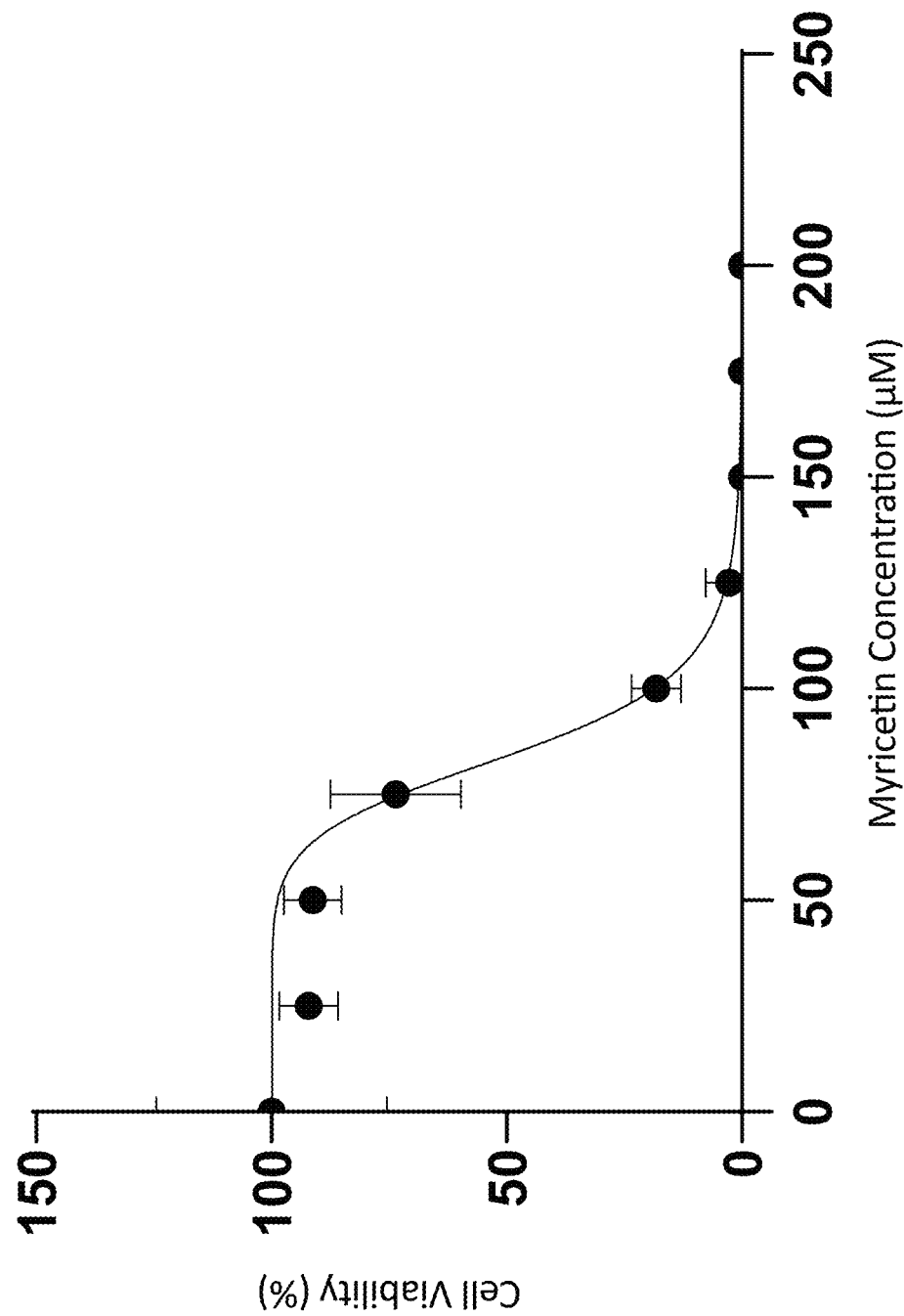
FIGS. 19A, 19B and 19C depict a comparison of one flavanol across different cell types.
Figure 19B:
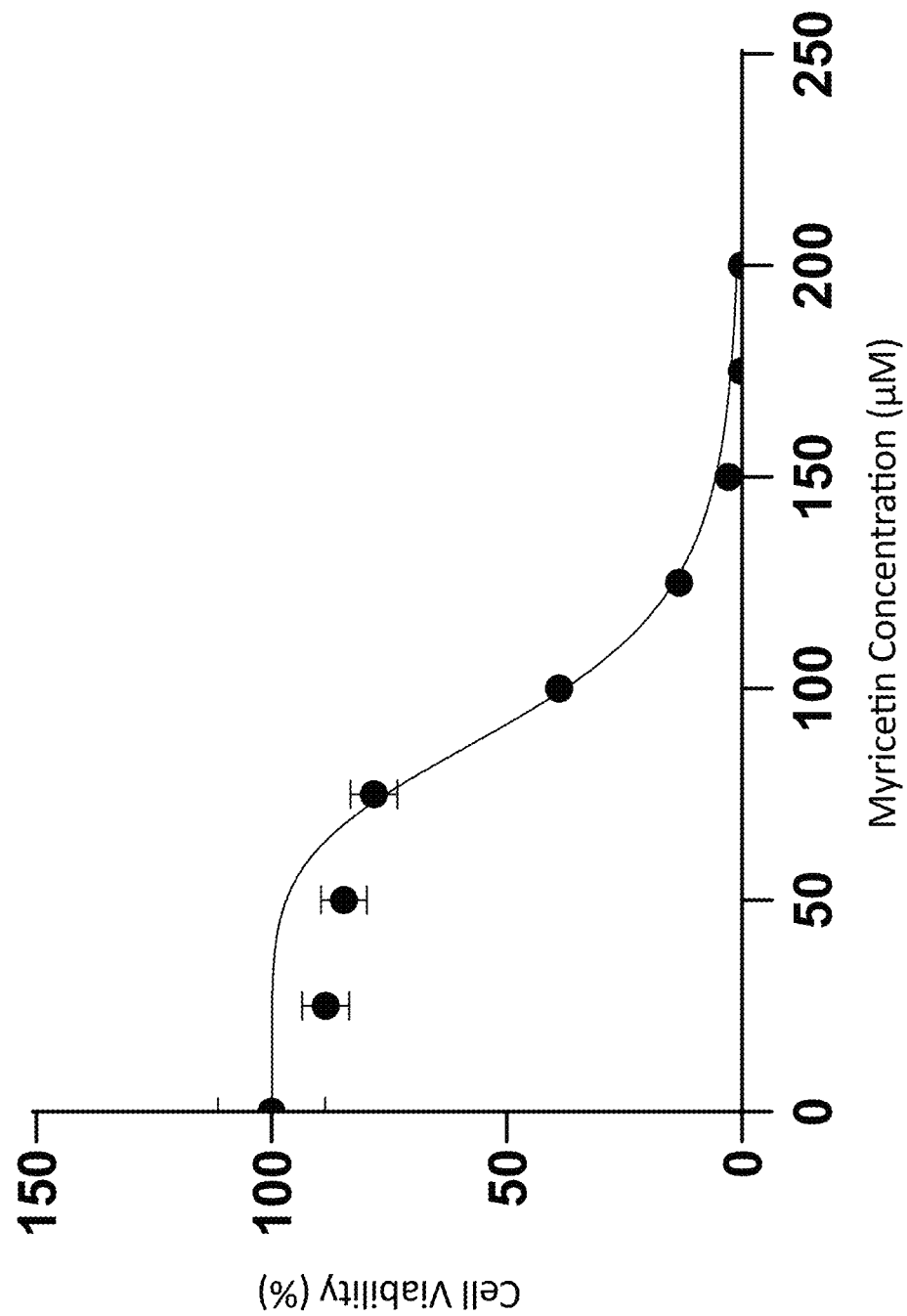
Figure 19C:
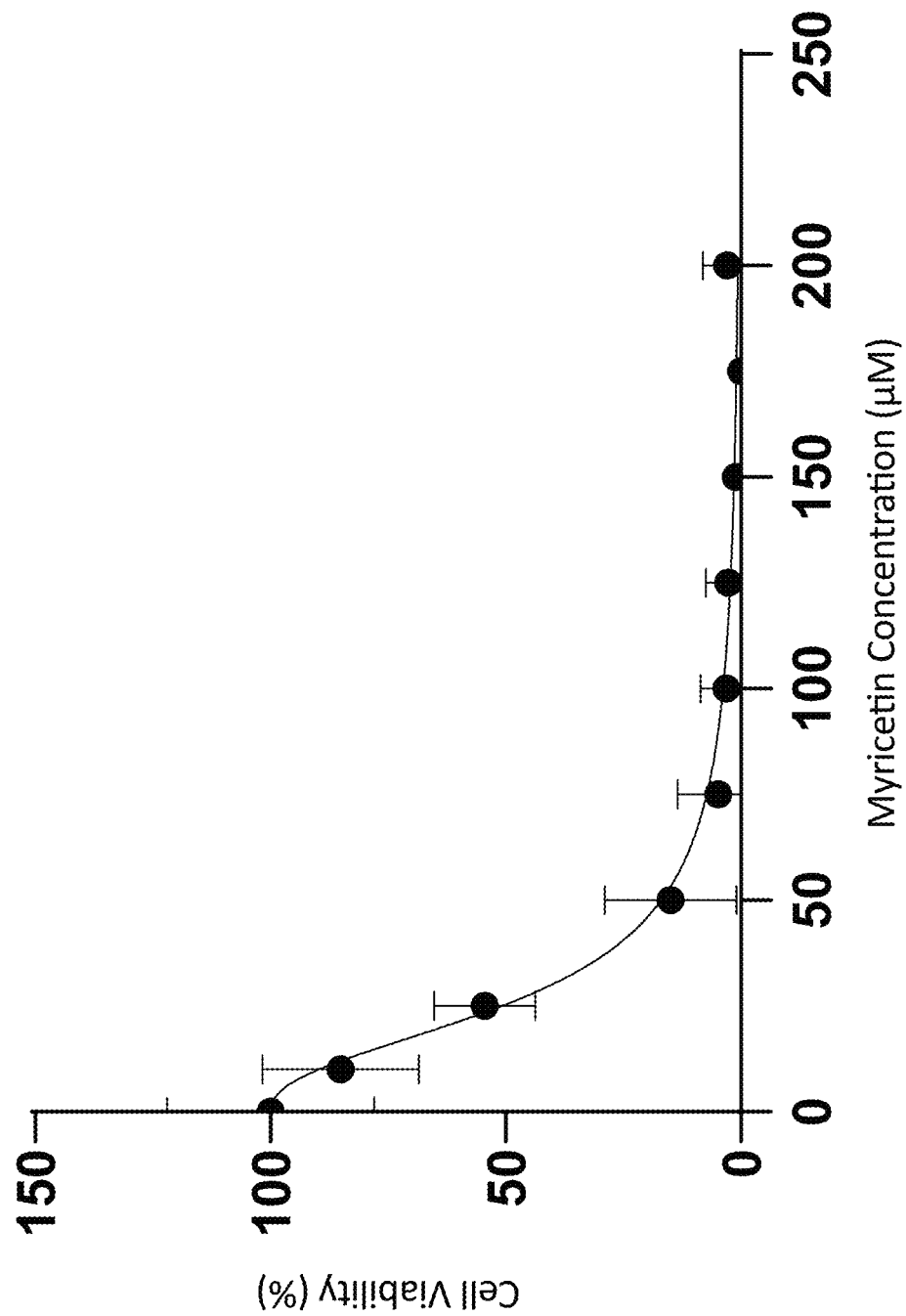

FIG. 18 then performs the same test as in FIGS. 17A and 17B just with a FSHE, to see if the results were conserved. Generally, myricetin showed a similar efficacy, while tocopherol essentially made the IC50 FSHE ineffective, and confirming that it should be avoided in combination with a *Cannabis* extract. Taxifolin was ineffective until at a higher concentration of about 45 µM, while others were somewhat more effective at concentrations below 20 and remained fairly stable through higher concentrations. Chrysin, maintained its efficacy improvements as seen with the BSHE test, and was generally the $2^{nd}$ most effective combination after the myricetin.

Thus, myricetin showed a significant synergy when used with either a BSHE or a FSHE, while other flavanols, flavononol, or flavone also showed unexpected synergy at slightly higher levels, but each of these flavonoids showed a greatly unexpected synergy in combination with either of the *Cannabis* extracts, which was wholly unexpected based on their monotherapy response. Accordingly, looking at the structure of myricetin, it has a higher number of hydroxyl groups on the phenol ring, as compared to either chrysin or taxifolin. Indeed, chrysin has no hydroxyl groups on the phenol ring, while taxifolin is a flavanonol, having the phenolic ring as a chiral center. Except for the chiral nature, taxifolin differs from myricetin only as to omitting one hydroxyl group attached at the 3' position on the Phenol ring (also called R3') herein as provided in the generic structure below.

Preferably, the composition is a flavonol, which has the following structure:

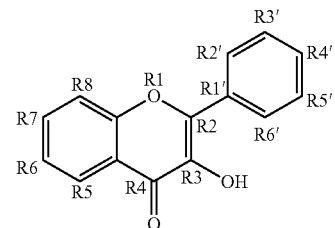

Notably, the R3 position for the flavonol differs from the prior structure in the substitution of the hydroxyl group at this position. The following flavonols and their structures at the various R groups detailed in Table 4:

TABLE 3

| | | | | FLAVONOLS | | | | | |
|---|---|---|---|---|---|---|---|---|---|
| Name | R5 | R6 | R7 | R8 | R2' | R3' | R4' | R5' | R6' |
| 3-Hydroxy-flavone | H | H | H | H | H | H | H | H | H |
| Azaleatin | OCH₃ | H | OH | H | H | H | OH | OH | H |
| Fisetin | H | H | OH | H | H | OH | OH | H | H |
| Galangin | OH | H | OH | H | H | H | H | H | H |
| Gossypetin | OH | H | OH | OH | H | OH | OH | H | H |
| Kaempferide | OH | H | OH | H | H | H | OCH₃ | H | H |
| Kaempferol | OH | H | OH | H | H | H | OH | H | H |
| Isorhamnetin | OH | H | OH | H | H | OCH₃ | OH | H | H |
| Morin | OH | H | OH | H | OH | H | OH | H | H |
| Myricetin | OH | H | OH | H | H | OH | OH | OH | H |
| Natsudaidain | OCH₃ | OCH₃ | OCH₃ | OCH₃ | H | H | OCH₃ | OCH₃ | H |
| Pachypodol | OH | H | OCH₃ | H | H | OCH₃ | OH | H | H |
| Quercetin | OH | H | OH | H | H | OH | OH | H | H |
| Rhamnazin | OH | H | OCH₃ | H | H | OCH₃ | OH | H | H |
| Rhamnetin | OH | H | OCH₃ | H | H | OH | OH | H | H |

Preferably, the flavonol comprises at least one hydroxyl group attached at one of R5, R6, R7, R8, R2', R3', R4', or R5'. Most preferably, there are at least two hydroxyl groups. And most preferably, at least one hydroxyl group is attached at least one of R5, R6, R7, or R8, and at least one hydroxyl group being attached at one of R2', R3', R4', or R5'.

Most preferably, the flavonol has a hydroxyl group attached at R5 and R7, and at least two of R2', R3', R4', R5', and R6', with the remaining being a hydrogen.

In addition to the flavonols tested, at two flavone molecules, luteolin and chrysin both showed therapeutic efficacy. The structure of these molecules being highly analogous to the flavonols, but simply replacing at R3 the —OH with a H. Otherwise, the position of the relative hydroxyl groups or hydrogens is analogous. Indeed, luteolin possesses hydroxyl groups attached at R5 and R7, and R3' and R4'. Chrysin, like luteoline has hydroxyl groups attached at R5 and R7, but no hydroxyl groups on the B benzene ring. The structure below represents a generic flavone:

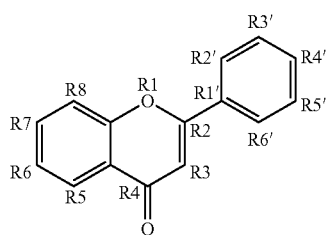

Finally, the taxifolin is a flavononol, having a chiral phenolic ring. However, it too generally conserves the hydroxyl groups and a hydrogen groups at each of the relevant carbon positions in the general structure. Each of these compounds, unexpectedly show that a unique and synergistic composition is identified that is able to induce apoptosis over endometrial cancer cells.

In addition to the therapeutic effect on the endometrial cancer lines, the response of a flavonol was further conserved when these were applied to a noncancerous organoid, as well as an ovarian cancer cell organoid. The relevant data is provided below in Table 4.

TABLE 4

CONCENTRATION OF MYRICETIN ON VARIOUS DISEASE STATES

| Concentration (µM) | Endometriosis Average | Ovarian Cancer Average | Endometrial Cancer Average |
|---|---|---|---|
| 0 | 100.00 | 100.00 | 100 |
| 10 | — | — | 85.01 |
| 25 | 92.10 | 88.60 | 54.50 |
| 50 | 91.37 | 84.68 | 15.11 |
| 75 | 73.66 | 78.36 | 4.98 |
| 100 | 18.33 | 38.95 | 0.00 |
| 125 | 2.85 | 13.49 | 0.00 |
| 150 | 0.00 | 2.97 | 0.00 |
| 175 | 0.00 | 0.00 | 0.00 |
| 200 | 0.00 | 0.00 | 0.00 |

This conservation of therapeutic efficacy has been conserved throughout all of Applicant's data and confirms that this particular model works in these varied disease states. In particular, treatment of endometriosis organoids confirms that treatment shall be effective in not only the endometrial cancer and ovarian cancer, but also to these noncancerous gynecological disease states such as: ovarian endometrioma, a deep endometriosis, dysmenorrhea, and fibroids. Indeed, it is postulated that the synergy may be implicated in part based on the estrogen dominance of most of these cancers and would support that other such estrogen sensitive or dominant diseases would also be effectively treated by these unexpected compositions.

Thus, the data shows an unexpected synergy towards the inclusion of one or more of certain classes of flavonoid antioxidants, while simultaneously, showing that certain molecules should be avoided. Most notably of these is that tocopherol should be excluded from formulations. This finding is profoundly unexpected, as the literature includes numerous citations in which carriers which are known to be high in tocopherol (for example, olive oil) are suggested to be used as the carrier, or as part of an oil in water emulsion. See US patent pub No. 2023/0090094 Hemp extract for treatment of pain, cancer and epilepsy in animals (Kjaer, et al.) or CA3020798A1 Ingestible films having substances from hemp or *Cannabis* (Schaneville).

Applicant's results show something that is otherwise completely unexpected. The presence of one or more flavonoids, in combination with CBD yields dramatic synergy towards killing cancerous cells as well as noncancerous disease. Therefore, a composition comprising CBD and one of more flavonoid is effective for treatment of the various gynecological cancers, estrogen mediated diseases, and non-cancerous gynecological disorders. In preferred embodiments, the flavonoid is a flavonol. In further preferred embodiments, the flavonoid is a flavonol, a flavononol, or a flavone.

Thus, the data details on unexpected synergy herein that compositions comprising CBD and a flavonoid, and particularly to flavonol, flavononols, or flavones are effective at treating several gynecological diseases, including estrogen mediated disease, estrogen receptor+disease, and certain nongynecological diseases including ovarian endometrioma, a deep endometriosis, dysmenorrhea, and fibroids. Furthermore, the compositions can be effectively utilized in one or more methods of treatment comprising administering to a patient in need thereof, of an effective amount of the composition to treat one or more of the disease states.

In a further preferred embodiment, the composition can also be provided in combination with a chemotherapeutic agent, wherein the combination of therapy can be utilized for treatment of endometrial cancer, ovarian cancer, and/or one or more estrogen mediated cancers.

In a preferred method, a method of treating a grade 1, 2, or 3 gynecological cancer comprising administering to a patient in need thereof, an effective amount of a composition comprising a *Cannabis* extract comprising CBD, and a flavonol. In preferred embodiments, the *Cannabis* extract comprises total cannabinoids of between 50 and 99.9 of the *Cannabis* extract. When described herein, the percent of the *Cannabis* extract, means that, as in the preceding sentence the total cannabinoids make up between 50 and 99.9% by weight of the *Cannabis* extract. Preferably, of the total cannabinoids, CBD makes up at least 60%, and more preferably, at least 65, 70, 75, 80, 85, 90, 95, and 99% of all cannabinoids within a *Cannabis* extract. In preferred embodiments, a dose is provided as an oromucosal dose, an intravaginal dose, a nasal mucosal dose, a rectal dose, an oral dose, an intramuscular injection, or an intravenous dose.

Currently, Applicant has data for no fewer than 21 patients for various gynecological cancers. Of these, ten received treatment for ovarian cancer, both with ascites recurrent chemoresistant cancer, and several with chemonaïve solid tumors. At least the following patients were determined for disease type and known mutations, including ovarian cystadenocarcinoma, with one patient having BRCA2, and TP53, with a second patient having BRCA2, NF1, and TP53. Two patients had high grade ovarian serous adenocarcinoma, with one patient having TP53 mutation, and the other with PIK3R1 and TP53 mutation. A further patient had high grade serous ovarian cancer, but no mutations noted. Another patient with Stage IIIc, high grade serous ovarian cancer was BRCA Negative. Two additional patients, one with Stage IVc, low grade serous ovarian cancer and one with undefined ovarian cancer did not have mutations noted. Thus, we can see that BRCA2, and TP53 are commonly conserved mutations being susceptible to the ovarian cancer in these patient lines, and whose organoids were then successfully treated with either of the *Cannabis* extract alone or concurrently with one or more chemotherapeutic agent.

Therefore, a preferred embodiment is related to a method of treatment of a gynecological cancer comprising administering to a patient an effective amount of a pharmaceutically acceptably composition comprising a *Cannabis* extract having between 50 and 100% by weight CBD, wherein the composition comprises one of a BSHE, a FSHE, a CBD isolate or CBDA as the CBD source and an antioxidant, which is a flavonol. In preferred embodiments, the composition is substantially free of a tocopherol (having less than 0.1 weight percent of the composition). In further preferred embodiments, the composition is completely free of a tocopherol (being present at a level below the limits of detection). In a further preferred embodiment, an effective dose is between 10 and 2500 mg a day of CBD.

In certain other applications, it may be suitable to co-administer the CBD treatment with an ongoing radiation or chemotherapeutic treatment. Therapeutic coadministration may be suitable for increasing efficacy and/or decreasing the dose and thus toxicity related to chemotherapeutic treatment.

In preferred embodiments it is advantageous to modify the osmolality of the composition for therapeutic administration so as to be gentle for intravaginal bacteria by the addition of one or more common salts. In further preferred embodiments, it may be appropriate to modify the PH of the carrier so as to more appropriately match the pH of the vagina, which is typically acidic. A buffer comprising the appropriate conjungate acid and base pair can be utilized to select and maintain an appropriate pH. Preferably, oral mucosal administration or intravaginal administration of the compositions are provided at a pH of between 2 and 6 and most preferably at between 3.5 and 6.

Methods

Development of patient derived organoids: The patient derived organoids were created as follows: the patient's tissue sample was collected after surgery and bathed in Hank's Balanced Salt Solution (HBSS) (Hyclone, SH30031.02) with 1% Pencillin/Streptomycin (P/S) (Life Technologies, 15070-063) on ice. Then the sample was washed three times with Dulbecco's phosphate-buffered saline (DPBS) and 1% P/S on a shaker (70 rpm) for 15 minutes each. The tissue was then transferred into a pre-sterilized cell-culture hood to mince it finely with a sterile blade. All minced parts were then digested in an enzyme named Accumax (Innovative Cell Technologies Inc., AM105-500) for 2.5 hours at room temperature. After 2.5-hour incubation, the whole digested tissue mince was transferred in another enzyme, TrypLE express, (Gibco, 12604-021) for another 45 minutes in a 37° C. water bath. During this time the solution was continuously agitated in every 5 minutes interval. After 45 minutes of incubation, the solutions were passed through 70 μm filter on a 50 mL falcon tube. The filter was removed, and the flow-through with the cells was collected in 5% FBS AD+++ medium (comprising 1% ITS, 2% B27, 1% N2, 25% WRN, hegf-50 ng/ml, hfgf-10-100 ng/mL, Nicotinamide-1 mM, N-acetyl cysteine-1.25 mM, Primocin-0.2%, Estrogen-2 nm, A8301-0.5 μM, and Y27632). This cell suspension was centrifuged at 1000 rpm for 5 minutes at room temperature to get the cell pellet for counting. Upon checking under hemocytometer cell number was calculated and processed for organoid culture. After checking under a microscope if we found RBC contamination in the final cell suspension, then we used Red Blood Cell Lysis Buffer (Roche Diagnostics, 11814389001) to get rid of the excess RBC. Human patient cells from endometrial cancer were grown and maintained in a humidified chamber at 37° C. with 5% CO2.

For the Ascites samples, we centrifuged the ascites fluid at 1000 rpm for 10 minutes at room temperature to get the cell suspension. The cell suspension was then treated with Red Blood Cell Lysis Buffer (Roche Diagnostics, 11814389001) to remove the RBC from the final cell suspension. Once samples were created, they were ready for testing, which included treating the organoids with *Cannabis* extract. Additional cells were cultured in the same manner as above.

Protocol for all Tests: Patient-Derived Organoid (PDO) Culture and Drug Treatment To culture patient-derived organoids, $2-3 \times 10^3$ cells were plated in a pre-warmed (37° C.) 96-well plate in 10 mL of Matrigel (5% FBS AD+++ medium) per well. Individual patient cell organoid was cultured separately in different plates. Individual patient cells were handled separately to reduce the chance of cross-contamination. After mixing cells with Matrigel, 10 mL droplets were placed in wells and put in a 37° C. incubator with 5% CO2 for 30 minutes. Upon solidification of the Matrigel droplet with cells inside, the plate was placed inside a sterile hood and immersed the Matrigel droplet in 200 μL of organoid growth media. Cells were allowed to grow into mature organoids for 14 days. Treatment with individual CBD agents (Broad Spectrum, Full Spectrum, CBD Isolates, and CBDA) or in combination with chemotherapeutic agents (Paclitaxel, Doxorubicin or Carboplatin) was started from day 1, where the individual drug or drug combinations were added in the growth medium. All treatments were done in triplicate, including vehicle-only controls (Dimethyl sulfoxide in culture medium at the highest concentration used for drug treatments).

Individual patient organoids were treated with all the respective *Cannabis* extracts (Broad Spectrum, Full Spectrum, CBD Isolates, and CBDA) to determine the IC50 by inhibitor vs normalized response-variable slope using least squares regression in Graphpad Prism 9. This IC50 was specific for individual patient and individual CBD agent. Now, the same patient's organoid was further treated with incremental doses of chemotherapeutic agents (Paclitaxel, Doxorubicin or Carboplatin) along with the specific IC50 of individual CBD agents for that specific patient. Notably, these doses all fall under the maximal doses suitable for human administration. This helped us to determine if the presence of specific dose (IC50) of individual CBD agents can reduce the dose of chemotherapeutic agents (Paclitaxel, Doxorubicin or Carboplatin) to get the same amount of cancer cell death as of the standard human dose. Note: IC50 is the 50% inhibitory concentration which is conventionally used to determine drug potency with cell-based cytotoxicity tests. Similarly, all of the antioxidants were tested under the same protocol.

Cell Viability Assay

To assess the cell viability in organoids after treatments, CellTiter-Glo® Luminescent Assay (Promega #G7572) was used. In brief, on day 14 of organoid culture, the matrigel droplet in each well with organoid inside was immersed in 100 μL of fresh growth media and 100 μL of CellTiter-Glo® reagent following the manufacturer's guideline. Blank wells containing only media and CellTiter Glo® reagent (no cells) were also included in each plate. Then the plates were put on a shaker at 110 RPM at room temperature for 5 minutes to induce cell lysis, followed by 25 minutes at room temperature to stabilize the luminescent signal. Each step after adding the CellTiter Glo® reagent was performed in the dark. Luminescence was measured on a FLUOstar OPTIMA plate reader (BMG Lab technologies, Offenburg, Germany).

Analysis was performed by normalizing treatment values to the vehicle control and plotting them as a percentage of the vehicle control. Drug IC50 values were determined by inhibitor vs normalized response-variable slope using least squares regression in Graphpad Prism 9.

Mouse Model: Patient-Derived Xenograft (PDX) Mouse Generation

Human patient cells from endometrial cancer were injected subcutaneously into female NOD/SCID gamma mice after resuspending in 100 μL solution. Once the tumor grows to a visible size all mice were intraperitoneally injected with CBD single agents (all 10-30 mg/kg body wt) and/or CBD+chemotherapeutics (CBD (10-30 mg/kg body wt), Paclitaxel (up to 20 mg/kg body wt)/Carboplatin (up to 60 mg/kg body wt), Doxorubicin (up to 15 mg/kg body wt)) or Vehicle thrice per week for up to 5 weeks. Tumor size measured before treatment, followed by twice a week measurement. All treatment group mice were kept alive for up to 10 weeks after drug injection or until the tumor volume grows bigger than 2500 mm$^3$.

Tumor size was measured along with body weight at the time of tissue collection. All tumor tissues were removed carefully from the euthanized mouse body. Tumor tissue samples were kept for histology, proteomics, genomics, and other downstream processing. All downstream processing was completed following NCI Patient-Derived Models Repository SOPs. Tumor volume graph will be plotted using GraphPad Prism 9.

Translating the organoid doses to an equivalent human dose was determined by a standard formula. (M=m/MW*1/V where m=mass in grams, MW=molecular weight of the substance and V=volume of the diluent in liters). Thus, for example, if CE has an organoid dosage of 54.35 μM it would be calculated as follows: That means we need 0.0032 mg of CE in 100 μL or 0.0001 L (V) that will be equivalent to 0.00005435 M or 54.35 μM concentration, where MW of CE=588.72 g/mol and m=0.0000032 g.

When performing additional tests, samples tested in 96 well plates can use a different formula for translating to human dosage. When testing with the 96 well plates, the surface area of a single well in 96 well plates is 0.32 cm$^2$. That means the clinical dose equivalent (mg/m$^2$) will be 100 mg/m$^2$ by following the formula below, Clinical Dosage (mg/m$^2$)=(PDO dosage in mg/culture plate surface area cm$^2$)×100$^2$. When comparing the two different methods of translating the organoid dose to the human dose, the two calculations show a very similar human equivalent dose, for example of approximately 200 mg/day for the organoid equivalent of 10 μg/mL.

Mouse PDX to Human Dose Conversion

The Food and Drug Administration (FDA) has suggested that the extrapolation of animal dose to human dose is correctly performed only through normalization to body surface area (BSA), which often is represented in mg/m2. The human equivalent doses (HEDs) can be more appropriately calculated by using the formula: Human Equivalent Dosage in mg/kg=Mice Dosage (mg/kg)×(Mice Km/Human Km). The correction factor (Km) is estimated by dividing the average body weight (kg) of species to its body surface area (m2). For example, the average human body weight is 60 kg, and the body surface area is 1.62 m2. Therefore, the Km factor for human is calculated by dividing 60 by 1.62, which is 37 and same way the mouse Km factor was calculated, which is 3. Now to interchange of unit (mg/kg to mg/m2) of dose of animals or human is carried out using the Km factor as per BSA: Dosage for mg/m2=Km×dosage in mg/kg.

The mouse studies utilized intraperitoneal dosing of various formulations of Cannabis extracts comprising a known quantity of CBD. For each of the various Cannabis extracts, BSHE, FSHE, CBD isolate, and CBDA, 2 to 3 mice were tested against each of a vehicle alone (control), with the results being compared to the volume at T=0 for each of the mice. Dosing was 30 mg/kg of each of the Cannabis extracts, the results of the CBD only study is defined in FIG. 5.

Notably, the concentration of CBD used in each case remains on the low end of the therapeutic dose suitable for administering to a human patient, or to a mouse. The low doses were utilized in order to show impact of the Cannabis extracts, instead of each of the data going to zero, by using double, triple, or higher of the dose as administered to the mice, all of which would be appropriate human equivalent doses. Even with the lower dosing, at time of 21 days, virtually all of the samples are progressing tumor volume toward zero, and in one case, the tumor volume has reached zero at day 21. Therefore, when comparing these quantities to those from the organoid data, we see that each sample retains the efficacy from the organoid data. Thus, administering higher doses of CBD, will yield a greater reduction in tumor volume in the mouse model. Thus, administering Cannabis extracts is effective in greatly slowing the growth of endometrial cancer tumors, and ultimately reduces the tumor size, which may result in the eradication of tumor cells, by administering the Cannabis extracts to the mice.

Delivery of therapeutic compositions and materials

The compositions detailed herein, namely comprising a Cannabis extract and a flavonoid is identified to produce an unexpected synergistic response towards destruction of diseased cells, specifically towards certain noncancerous gynecological cells or lesions, as well as towards cancerous lesions, solid tumor cancers, and specifically those of endometrial cancer and ovarian cancer.

Delivery mechanisms are provided for delivering the active therapeutic ingredients to a patient. When treating gynecological diseases, specifically in female patients, Applicant identified that gynecological tissues can be targeted by certain applications, whether through oral, oral mucosal, vaginal mucosal, or other administration to treat gynecological tumors, and reduce tumor size through treatment with Cannabis extracts comprising CBD. Because of the targeted approach towards gynecological tissues, those of ordinary skill in the art will recognize that certain therapeutics are able to pass through the vaginal mucosa and contact tissues both on the vaginal wall, but also tissues adjacent to the vaginal wall, including the entirety of the gynecological tract, including the uterus, cervix, ovaries, etc., as nonlimiting tissues. Indeed, while these tissues are generally connected, application into the vagina does not always ensure that a therapeutic will also travel to and impact the uterus or ovaries. However, there is an abundance of endocannabinoid receptors in the female reproductive tract to allow for possible binding of administered cannabinoids to such tissues, as is depicted in FIGS. 1E and 1F. Furthermore, there may be uptake via the inguinal lymphnodes, leading to addition systemic uptake from the reproductive tract.

Intravaginal delivery is well studied and considered safe, effective and well tolerated. Intravaginal delivery avoids gastrointestinal absorption and bypasses first pass metabolism, while facilitating a localized effect and a steady, sustained therapeutic response. Absorption and systemic delivery via vaginal epithelium occurs rapidly with similar lipophilic compounds. Variances in thickness of the vaginal epithelium and vagina fluid characteristics, including pH, presence of cervical mucous, and microbiota, may influence absorption rates and bioavailability.

Accordingly, mucosal dosing, particularly intravaginal dosing has a therapeutic efficacy that can allow for targeted treatment of EC cells, which will treat both localized tumors as well as metastasized tumors. These data were confirmed by further testing within human patients, which showed that treatment with CBD was effective in reducing chemoresistant EC, which had metastasized, in the body. Full spectrum hemp extract, broad spectrum hemp extract, CBD isolate, and CBDA isolate are forms of *Cannabis* extract utilized herein, as nonlimiting examples of the CE. Throughout the application, the term CBD is often used interchangeably with CE, to mean the CE product containing the particular amount of CBD. while in other instances, which are obvious to the reader, the CBD refers to a CBD isolate, which means the CE was processed to remove and isolate CBD, removing virtually all other components of the CE.

Whether through oral, oral mucosal, vaginal mucosal, or other routes of administration to treat NCGD, gynecological cancers, such as endometrial or ovarian cancer, CEs in combination with a flavonoid, as detailed herein, was unexpectedly synergistic and provides for a new therapeutic opportunity for treatment of these and other disease and disorders.

Mucosal dosing may be easily administered through the oral mucosa. Data on oral-mucosal or sublingual delivery, demonstrates that CBD has a maximum plasma concentration of 1.6 hours, but this can be delayed in some individuals. Orally delivered CBD has a maximum plasma concentration of about 2.5-5 hours but can be delayed up to 6 hours for some individuals. Coadministration with high fat food has been shown to increase Cmax by up to 5-fold concentration. Furthermore, the prevalence of lymph nodes in the back of the mouth then allows for more rapid onset and uptake of the CBD systemically.

In certain situations, administration may be desirable within the sinus cavity, and thus delivery of CBD via highly vascularized nasal mucosa may be desirable. Studies have shown that CBD delivery via the nasal mucosa results in rapid uptake and a Tmax of approximately 10 minutes. Furthermore, as the material passes to the rear of the sinuses, it will pass through the throat and may serve as one of the best ways to reach certain metastases from the cancer, as well as the significant lymph system within the sinus and throat.

Finally, rectal application may also be suitable in certain applications. Rectal suppository delivery results in an increased bioavailability (51-60%) versus oral routes for CBD. Accordingly, mucosal dosing, can allow for targeted administration of *Cannabis* extracts to treat both local and also metastatic tumors. Additional dosing may still be accomplished via traditional dosing routes, including but not limited to oral dosage forms, such as a soft gel comprising a *Cannabis* extract. Furthermore, administration may be injected, intramuscularly, or into other suitable tissues for uptake.

Accordingly, mucosal dosing, particularly intravaginal dosing has a therapeutic efficacy that can allow for targeted treatment of NCGD, and gynecological cancer cells. These therapeutic compositions and methods will treat both localized lesions or tumors as well as metastasized tumors in diseases such as ovarian cancer and endometrial cancer. These data were confirmed by further testing within human patients, which showed that treatment with CBD was effective in reducing chemoresistant EC, which had metastasized, in the body.

Preferably, as detailed in the experiments and embodiments herein, a composition comprises a CE and at least one flavonoid. Preferably, the flavonoid is a flavonol, a flavone or a flavononol, and most preferably comprising at least one hydroxyl group, and most preferably at least two hydroxyl groups at R5, R6, R7, R8, and R2', R3', R4', and R5'. Preferably, the composition for mucosal administration comprises a carrier. Preferably, the composition further comprises one or more mucoadhesive compounds. Furthermore, the composition further comprises one or more stabilizers. Furthermore, the composition further comprises one or more flowing agents, bulking agents, and a buffer. Finally, the composition may also comprise a chemotherapeutic agent. Alternatively, the composition may include the CE, and a second composition comprises the flavonoid, and/or a chemotherapeutic agent, or even a third composition comprising the flavonoid and/or the chemotherapeutic agent.

Preferably, the composition is buffered to be acidic, when administered to the mucosal surface. Wherein the acidic pH at between 2 and 6, and preferably between 3.5 and 6, and most preferably between 4 and 5, increases the efficacy of the composition, as compared to buffering at 10.5, or about the native pH of the CE without a carrier or buffer added thereto.

In preferred embodiments, the CE comprises a FSHE or a BSHE. Most preferably, the FSHE or the BSHE are purified extracts comprising two or more cannabinoids. However, it is further preferred that the composition is formulated with at least 1% to 10% CBDA. CBDA is reported to increase the bioavailability of CBD. Thus, the CBDA, being in an acid form, also includes a stabilizing agent to prevent the oxidation of the CBDA to CBD. Preferably, the antioxidant, as the flavonol may be included at between 0.1% and 10%. In certain applications the combination of CBD and CBDA allows for an increase in the rate of absorption of both the CBDA and the CBD, thus increasing the efficacy of the composition as a whole.

It will be appreciated that the embodiments and illustrations described herein are provided by way of example and that the present invention is not limited to what has been particularly disclosed. Rather, the scope of the present invention includes both combinations and sub combinations of the various features described above, as well as variations and modifications thereof that would occur to persons skilled in the art upon reading the forgoing description and that are not disclosed in the prior art. Therefore, the various compositions and methods may include one or all of the limitations of an embodiment be performed in any order or may combine limitations from different embodiments, as would be understood by those implementing the various methods and systems detailed herein.

What is claimed is:

1. A composition for treatment of noncancerous gynecological disorders or gynecological cancers comprising cannabidiol (CBD) from an isolate or extract at between 50% and 99.9% by weight of the composition and a flavonoid at between 0.1% and 50% by weight of the composition, said flavonoid selected from the group consisting of: myricetin, chrysin, taxifolin, galangin, luteolin, 3-hydroxyflavone, and combinations thereof.

2. The composition of claim 1 wherein the cannabidiol is provided from a full spectrum hemp extract (FSHE), a broad spectrum hemp extract (BSHE), a CBD isolate, cannabidiolic acid (CBDA), and combinations thereof.

3. The composition of claim 1 wherein the cannabidiol is provided from a BSHE or FSHE and comprises (i) from 50% to 99.9% by weight of CBD and (ii) at least one other cannabinoid selected from Δ-9-tetrahydrocannabinol (Δ9-THC), tetrahydrocannabinolic acid (THCA), tetrahydrocannabivarin (THCV), Δ-8-tetrahydrocannabinol (Δ8-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

4. The composition of claim 3 wherein at least a portion of the CBD is synthetic.

5. The composition of claim 1 wherein the flavonoid has a concentration of at least 50 μM.

6. The composition of claim 1 wherein the composition is substantially free of tocopherol.

7. The composition of claim 1 which is suitable for administration orally, rectally, via an oral mucosa, via a vaginal mucosa, via a nasal mucosa, dermally, subcutaneously, or intravenously.

8. The composition of claim 1 wherein the ratio of the cannabidiol to the flavonoid is 5 μg/mL: 1 μM to 5 μg/mL: 200 μM and all ratios in between.

9. The composition of claim 1 wherein the composition comprises a carrier; and the composition has a pH of between 3.5 to 6.

10. A method of treatment of a gynecological disease or disorder comprising administering to a patient in need thereof an effective amount of a composition comprising cannabidiol (CBD) at between 50% and 99.9% by weight of the composition and a flavonoid at between 0.1% and 50% by weight of the composition, the flavonoid selected from the group consisting of: myricetin, chrysin, taxifolin, galangin, luteolin, 3-hydroxyflavone, and combinations thereof.

* * * * *